(12) United States Patent
Gupta et al.

(10) Patent No.: US 9,676,916 B2
(45) Date of Patent: Jun. 13, 2017

(54) MULTIFUNCTIONAL SYNTACTIC FOAMS

(71) Applicant: New York University, New York, NY (US)

(72) Inventors: Nikhil Gupta, Ossining, NY (US); Vasanth Chakravarthy Shunmugasamy, Brooklyn, NY (US)

(73) Assignee: NEW YORK UNIVERSITY, New York, NY (US)

( * ) Notice: Subject to any disclaimer, the term of this patent is extended or adjusted under 35 U.S.C. 154(b) by 151 days.

(21) Appl. No.: 14/444,677

(22) Filed: Jul. 28, 2014

(65) Prior Publication Data

US 2015/0031793 A1    Jan. 29, 2015

Related U.S. Application Data

(60) Provisional application No. 61/859,185, filed on Jul. 27, 2013.

(51) Int. Cl.
| | |
|---|---|
| *C08J 9/32* | (2006.01) |
| *G01N 33/20* | (2006.01) |
| *G01N 33/44* | (2006.01) |
| *G01N 15/08* | (2006.01) |

(52) U.S. Cl.
CPC .............. *C08J 9/32* (2013.01); *G01N 15/088* (2013.01); *G01N 33/20* (2013.01); *G01N 33/44* (2013.01); *C08J 2205/044* (2013.01); *C08J 2331/02* (2013.01); *C08J 2363/00* (2013.01); *G01N 2203/0094* (2013.01)

(58) Field of Classification Search
CPC .......................................... C08J 9/32
USPC ................................. 523/218, 219
See application file for complete search history.

(56) References Cited

U.S. PATENT DOCUMENTS 5,354,611 A * 10/1994 Arthur ..................... C08K 7/28
264/211

OTHER PUBLICATIONS

Porfiri et al., Effect of Volume Fraction and Wall Thickness on the Elastic Properties of Hollow Particle Filled Composites, 2008, 8 pages.
Shunmugasamy et al., Electrical Properties of Hollow Glass Particle Filled Vinyl Ester Matrix Syntactic Foams, 2013, 11 pages.
Shunmugasamy et al., Thermal Expansion Behavior of Hollow Glass Particle/Vinyl Ester Composites, 2012, 9 pages.
Tagliavia et al., Analysis of Hollow Inclusion-Matrix Debonding in Particulate Composites, 2010, 14 pages.

* cited by examiner

*Primary Examiner* — Edward Cain
(74) *Attorney, Agent, or Firm* — Foley & Lardner LLP

(57) ABSTRACT

A multifunctional syntactic foam including a matrix material and hollow particles, where a first and second material property of the syntactic foam are tailored on the basis of the wall thickness and volume fraction of the hollow particles.

18 Claims, 34 Drawing Sheets

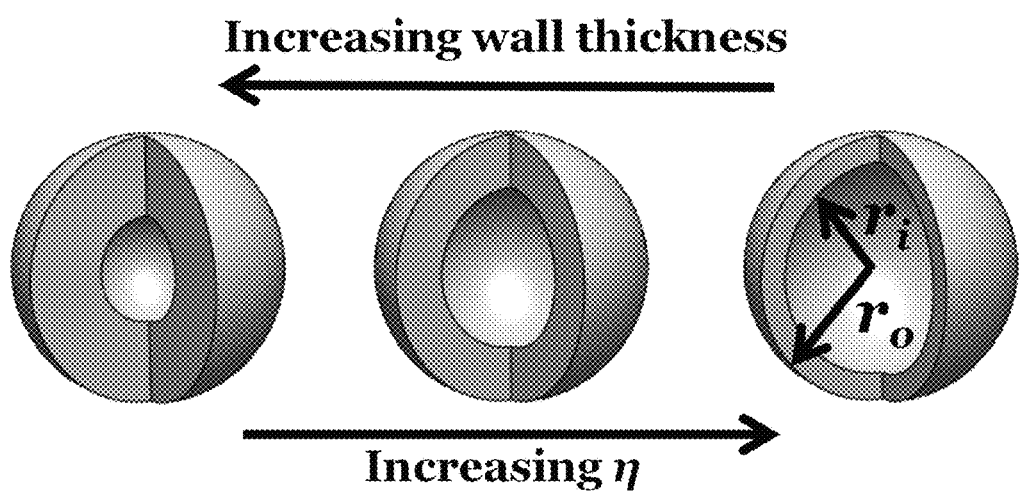
Fig. 1
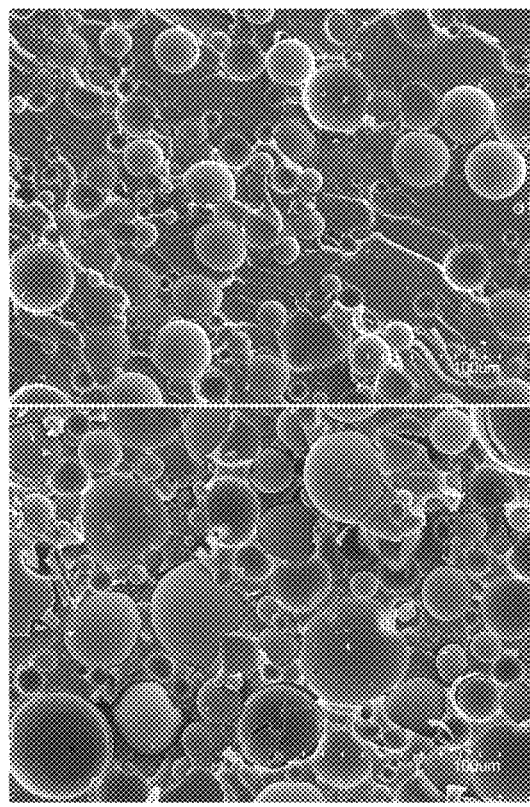
Fig. 2A
Fig. 2B

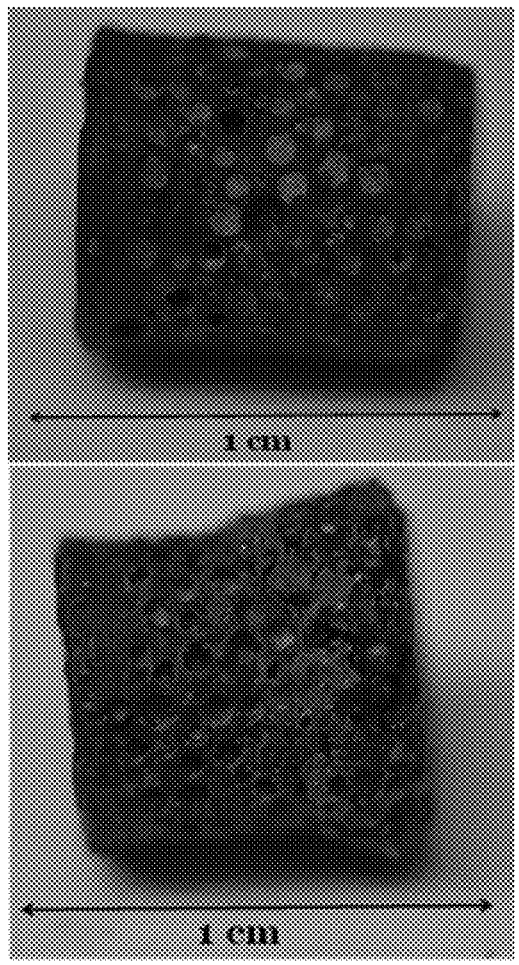
Fig. 41A
Fig. 41B
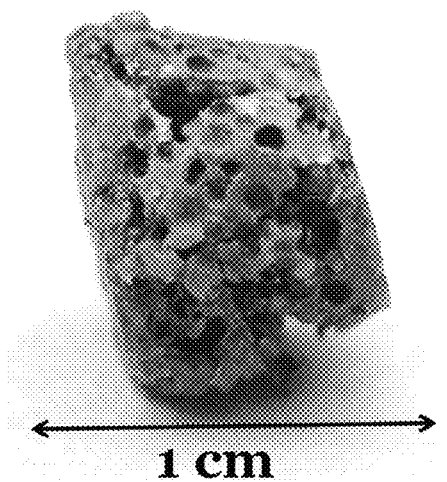
Fig. 41C

MULTIFUNCTIONAL SYNTACTIC FOAMS

CROSS-REFERENCE TO RELATED PATENT APPLICATIONS

This application claims priority from U.S. Provisional Application Ser. No. 61/859,185, filed Jul. 27, 2013, which is incorporated herein by reference in its entirety.

STATEMENT OF GOVERNMENT SUPPORT

The United States Federal Government may have certain rights in this invention. The subject matter of the application was carried out in part under grant number N00014-10-1-0988 from the Office of Naval Research.

BACKGROUND OF THE INVENTION

The present invention is generally related to materials that are used in the field of packaging or structural applications, such as syntactic foams, and is more specifically related to materials that have properties, such as dielectric constants, that may be tailored so as to be useful in such applications.

The dielectric constant is an important property in electronic substrate or packaging applications. Materials that have a possibility of tailoring their dielectric constant may be very useful in such applications. In addition, an increase in temperature during the usage of electronic components may be a challenge that may lead to thermal stresses and failure. Syntactic foam composite materials have been employed in such applications.

Very large scale integration of electronic circuits has drastically reduced the size of circuit boards used in electronic devices. This has created a desire to develop materials with low dielectric constant, high specific strength, low density, low moisture absorption and high durability. Integrated circuit boards, which form the heart of computers, require electrical insulators with low and preferably tunable dielectric properties. Polymers and polymeric composites have found applications in such fields due to their low dielectric properties.

Epoxy resins, which are often used as matrix materials for composites, may also be used in electrical and electronic fields as insulators, dielectrics and as underfills in circuit boards. One of method of decreasing the dielectric constant of the polymer is to introduce porosity in the polymer. Since air has a low dielectric constant of 1, the dielectric constant of polymer foams is low and may also accompany low strength and stiffness, which are undesirable. In addition, irregular size and distribution of gas voids in polymer foams may lead to mechanical property variation within the material.

The instant inventors are not aware of an instance where the dielectric constant and the coefficient of thermal expansion of a syntactic foam have been tailored simultaneously. Accordingly, there is a need for a syntactic foam composite material that may be simultaneously tailored for multiple properties, such as dielectric constant, coefficient of thermal expansion (CTE), and density,

SUMMARY OF THE INVENTION

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

A method is provided including: calculating, utilizing at least one computer, a range of potential values for a first material property of a syntactic foam, the syntactic foam including a matrix material and hollow particles, on the basis of a wall thickness and a volume fraction of the hollow particles; selecting a first material property value from the range of potential values for the first material property; calculating, utilizing at least one computer, a range of potential values for a second material property of the syntactic foam on the basis of the wall thickness and the volume fraction of the hollow particles while maintaining the selected first material property value; selecting a second material property value from the range of potential values for the second material property; and calculating, utilizing at least one computer, the wall thickness and the volume fraction of the hollow particles that will produce a syntactic foam with the selected first material property value and the selected second material property value. The first material property and the second material property may be selected from the dielectric constant, coefficient of thermal expansion (CTE), damping capacity, elastic modulus, storage modulus, loss modulus, and density, and the first material property is different than the second material property.

A method is provided including: calculating, utilizing at least one computer, a range of potential values for a first material property of a syntactic foam, the syntactic foam including a polymer matrix material and hollow glass particles, on the basis of a wall thickness and a volume fraction of the hollow glass particles; selecting a first material property value from the range of potential values for the first material property; calculating, utilizing at least one computer, a range of potential values for a second material property of the syntactic foam on the basis of the wall thickness and the volume fraction of the hollow glass particles while maintaining the selected first material property value; selecting a second material property value from the range of potential values for the second material property; and calculating, utilizing at least one computer, the wall thickness and the volume fraction of the hollow glass particles that will produce a syntactic foam with the selected first material property value and the selected second material property value. The first material property and the second material property may be selected from the dielectric constant and the coefficient of thermal expansion (CTE), and the first material property is different than the second material property.

A syntactic foam is provided. The syntactic foam may have a coefficient of thermal expansion of about $30 \times 10^{-6}$ ° C. to about $70 \times 10^{-6}$ ° C., and a dielectric constant of about 2.6 to about 4.9. The syntactic foam may include a matrix material and hollow particles.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 1 is graphical representation of hollow particles of various wall thicknesses.

FIGS. 2A and 2B are scanning electron micrographs of syntactic foam specimens VE460-30 and VE460-60, respectively.

FIGS. 41A, 41B, and 41C show failure features of the SF1 type SiC$_{HS}$/VE syntactic foams subjected to quasi-static compression testing corresponding to markings a, b, and c in FIG. 40, respectively.

DETAILED DESCRIPTION OF THE PREFERRED EMBODIMENTS

Figure 3A:
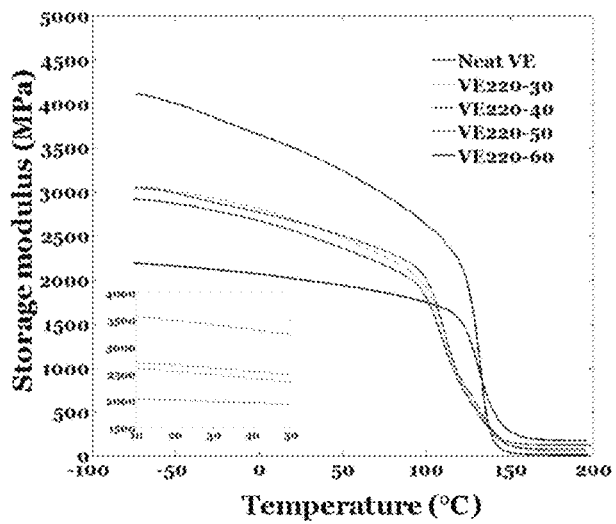
FIGS. 3A, 3B, and 3C depict the storage modulus of VE220, VE320, and VE460 syntactic foams, respectively, for a variety of microballoon volume fractions as a function of temperature, with the inset showing the temperature range of 10° C. to 50° C.

Following below are more detailed descriptions of various concepts related to, and embodiments of, inventive processes for the selection of a volume fraction and wall thickness of hollow particles in a syntactic foam to produce a syntactic foam with two independently tailored material properties. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

The present invention includes a method that may be applied to any combination of hollow particles and a matrix material to produce syntactic foams with two individually tailored properties. For example, a syntactic foam composite material may be simultaneously tailored for a desired dielectric constant and coefficient of thermal expansion (CTE). A range of compositions may be developed for syntactic foams that have the same dielectric constant but have different CTE values, and vice versa. Selection of an appropriate material composition allows the production of syntactic foams with both desired properties, such as dielectric constant and CTE.

As utilized herein, a syntactic foam includes hollow particles distributed in a matrix material. Syntactic foams may be low density composite materials with a significant volume fraction of porosity. The mechanical and thermal properties, such as elastic modulus, loss modulus, density, coefficient of thermal expansion (CTE) and thermal conductivity, of a syntactic foam may be tailored. The variables in designing syntactic foams include: the particle and the matrix materials, the volume fraction of the particles, and the wall thickness of the particles. In many applications, weight is an important consideration in using syntactic foams. A combination of hollow particle wall thickness and volume fraction may be used to independently tailor the CTE and the density of syntactic foams to achieve weight savings in structural applications.

The matrix material may be any suitable material, such as a polymer, metal or ceramic. According to one embodiment, the matrix material may be a vinyl ester resin. According to another embodiment, the matrix material may include aluminum.

The hollow particles may be any suitable particles. The particles may be spherical, cubic, cuboidal, cylindrical or any other appropriate geometry. The particles may include a ceramic, glass, polymer or carbon material—such as alumina, boron carbide, silicon carbide, carbon, phenolic polymers, or epoxy resin. According to one embodiment, the hollow particles may be spherical glass microballoons. According to another embodiment, the hollow particles may be hollow spherical silicon carbide particles. The hollow particles may be any suitable size. According to one embodiment, the hollow particles may be microparticles.

The properties of the syntactic foams may be tailored based on the volume fraction and wall thickness of the hollow particles. According to one embodiment, at least two properties of the syntactic foam may be independently tailored. Theoretical calculations allow the prediction of the volume fraction and wall thickness of the hollow particles that will produce a desired property. The theoretical calculations may be performed on at least one computer. A desired material property may be produced for a range of volume fraction and wall thickness values. Thus, a first desired material property may be selected, and a range of potential values for a second material property may be calculated that may be achieved by altering the volume fraction and wall thickness while also maintaining the desired first material property. The effect of the volume fraction and wall thickness on various material properties of the syntactic foam are described below.

The appropriate volume fraction and wall thickness for achieving a desired first and second material property may be determined by a material property tailoring process. First, a potential range of first material property values may be calculated based on the alteration of the volume fraction and the wall thickness of the hollow particles, and then a desired first material property value may be selected. A potential range of a second material property may then be calculated based on the range of volume fraction and wall thickness of the hollow particles that may produce the desired first material property. The selection of a desired second material property value from the calculated second material property potential range then allows the calculation of the volume fraction and wall thickness of the hollow particles that may produce a syntactic foam that exhibits both the first and the second selected material properties. The first and the second material properties may be any material property of the syntactic foam that exhibits a relationship to the volume fraction and wall thickness of the hollow particles, such as those properties described below. The first and second properties be selected from the dielectric constant, coefficient of thermal expansion, density, stiffness, thermal conductivity, glass transition temperature, loss modulus, storage modulus, damping parameter, and dynamic properties. The first and second material properties may be different material properties.

In addition to the volume fraction and wall thickness of the hollow particles, other factors may influence the calculated potential material property ranges. These additional factors may include the matrix material selected, the hollow particle material selected, and the type of processing utilized to produce the syntactic foam. For example, a syntactic foam produced by a shear mixing process may include an increased amount of broken hollow particles, adversely impacting the properties of the produced syntactic foam. Additionally, the properties of the raw materials employed in the production of the syntactic foams may impact the material properties of the produced syntactic foams.

The syntactic foams described herein may be especially suited for a variety of applications. The syntactic foams may be utilized in marine applications, including submarine components, ship components, deep sea vehicle components, undersea pipeline components, buoy components, and equipment platform components. Alternatively, the syntactic foams may be utilized in aerospace components, including spacecraft components, aircraft components, and antenna units. The syntactic foams may also be utilized in electronic device components, such as radio equipment and printed circuit board components. Other applications for which the syntactic foams may be suited include sports equipment, furniture, food and beverage containers, composite tooling components, vacuum forming plug assists, blast protection components, fire protection components, furniture, and medical devices.

Viscoelastic Properties

The understanding of the viscoelastic properties of syntactic foams at a wide range of temperatures and loading frequencies may be helpful for developing composites with tailored vibration response, high temperature mechanical properties, and energy absorption capabilities.

Dynamic mechanical analysis (DMA) is a technique for the characterization of viscoelastic material parameters. In this technique a sinusoidal force is applied to a specimen and the phase difference in the stress and strain response due to viscoelasticity is recorded. The in-phase and out-of-phase components of stress are used to calculate the storage modulus (E') and loss modulus (E''), respectively. The storage modulus provides a measure of energy stored in the material, and the loss modulus refers to the amount of energy dissipated in each cycle of the sinusoidal deformation. The ratio of the loss modulus to the storage modulus is the damping parameter, Tan δ. Loss modulus-temperature data may be used to measure the glass transition temperature ($T_g$). Correlations of these properties with the microballoon wall thickness and microballoon volume fraction (Φ) of syntactic foams may allow the production of syntactic foams with selected properties. Such correlations between the fundamental microstructural features and dynamic properties of syntactic foams may allow the engineering of syntactic foams to various requirements despite the wide variety of matrix and microballoon materials employed.

Twelve compositions of syntactic foams were fabricated with a systematic variation in microballoon wall thickness and volume fraction to enable the establishment of a correlation between these parameters with the measured properties of the composites. The combined effect of frequency and temperature on the dynamic mechanical properties was analyzed. The William-Landel-Ferry (WLF) equation may be employed for the time-temperature superposition (TTS) to obtain the variation of viscoelastic properties such as storage modulus, loss modulus, and damping parameter over a wide frequency range.

Vinyl ester resin was used as the matrix material for preparing the syntactic foams. Methyl ethyl ketone peroxide was used as the catalyst to polymerize the vinyl ester resin. Hollow glass microballoons of three nominal true particle densities, namely 220 kg/m³, 320 kg/m³ and 460 kg/m³, were used in volume fractions of 0.3 to 0.6. Since the density of the microballoons is less than half the density of the resin system, flotation of the microballoons may occur and the quality of the composite may not be uniform at microballoon volume fractions lower than 0.3. The properties of the glass microballoons employed are presented in Table 1.

TABLE 1

| Specimen type | Mean particle diameter (μm) | Nominal true particle density (kg/m³) | Particle wall thickness (μm) | Particle radius ratio |
|---|---|---|---|---|
| S22 | 35 | 220 | 0.52 | 0.970 |
| S32 | 40 | 320 | 0.88 | 0.956 |
| K46 | 40 | 460 | 1.29 | 0.949 |

Since the particles have nearly the same outer diameters, the main varying parameter is the wall thickness (w), as illustrated in FIG. 1. The radius ratio, η, defines the geometric properties of hollow particles as $$\eta = r_i/r_o \qquad (1)$$

where $r_i$ and $r_o$ are the internal and the outer radii of the microballoon. The particle wall thickness may be defined in terms of radius ratio as $w = r_o(1-\eta)$. Thus, η is lower for a thicker walled hollow particle of the same radius. The outer diameter of the particles and the wall thickness may be varied independently.

FIGS. 2A and 2B show the microstructures of syntactic foams containing Φ of 0.3 and 0.6, respectively. The measured and the theoretical densities of the composites are shown in Table 2. The theoretical density may be obtained using the rule of mixtures. Some undesired voids, termed matrix porosity, may be present in the matrix. The volume fraction of the matrix porosity $\Phi_p$ may be given by $$\Phi_p = \left(\frac{\rho_{th} - \rho_{exp}}{\rho_{th}}\right) \times 100 \qquad (2)$$

where $\rho_{th}$ and $\rho_{em}$, are the theoretical and the experimental densities, respectively, of syntactic foams. The calculated matrix porosity content is given in Table 2, which is of similar level and below 5 vol. % for all the produced syntactic foams, except for VE220-60. The specimens in Table 2 are named according to the following nomenclature: VE for vinyl ester, followed by the true particle density and the particle vol. %.

TABLE 2

| Specimen type | Theoretical density (kg/m³) | Experimental density (kg/m³) | Matrix porosity (vol %) |
|---|---|---|---|
| VE220-30 | 878 | 852 | 3.0 |
| VE220-40 | 784 | 765 | 2.4 |
| VE220-50 | 690 | 683 | 1.0 |
| VE220-60 | 596 | 538 | 9.7 |
| VE320-30 | 908 | 877 | 3.4 |
| VE320-40 | 824 | 786 | 4.6 |
| VE320-50 | 740 | 704 | 4.9 |
| VE320-60 | 656 | 632 | 3.7 |
| VE460-30 | 950 | 918 | 3.3 |
| VE460-40 | 880 | 850 | 3.4 |
| VE460-50 | 810 | 772 | 4.6 |
| VE460-60 | 740 | 703 | 4.9 |

Specimens of nominal dimensions 30×11×1.75 mm (length×width×thickness) were prepared for all experiments. The specimen width and thickness were controlled within ±1% accuracy. The specimens were cut using a low speed precision diamond blade saw and then dried in a convection oven for 3 h at 70° C. prior to testing. A Dynamic Mechanical Analyzer was utilized to conduct the experiments. The experiments were performed in single cantilever mode with a span length to thickness ratio of 10. A frequency of 1 Hz was employed for studying the effect of temperature on dynamic properties. The temperature range used in the study was from −75° C. to 195° C., at a heating rate of 5° C./min and an isothermal soak time of 1 minute. The specimens were tightened in the cantilever clamp using a torque of 0.8 Nm.

A TTS study was also performed under the single cantilever mode on specimens of the same geometry. The experiments were conducted in a frequency range of 1-100 Hz, divided linearly into 20 divisions. The testing temperature range was 30° C. to 140° C., with an isothermal soak time of 1 minute and the frequency sweep at every 5° C.

Figure 3B:
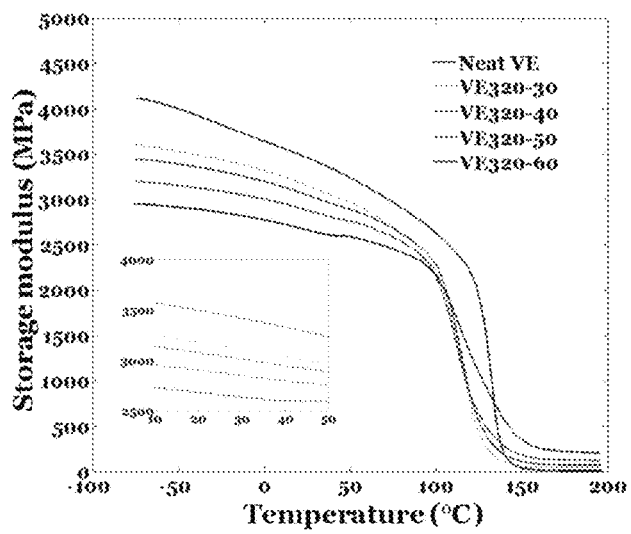
Figure 3C:
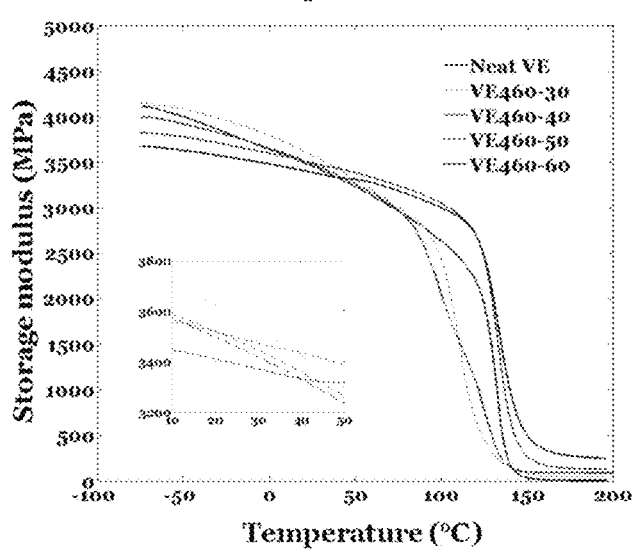
Figure 4:
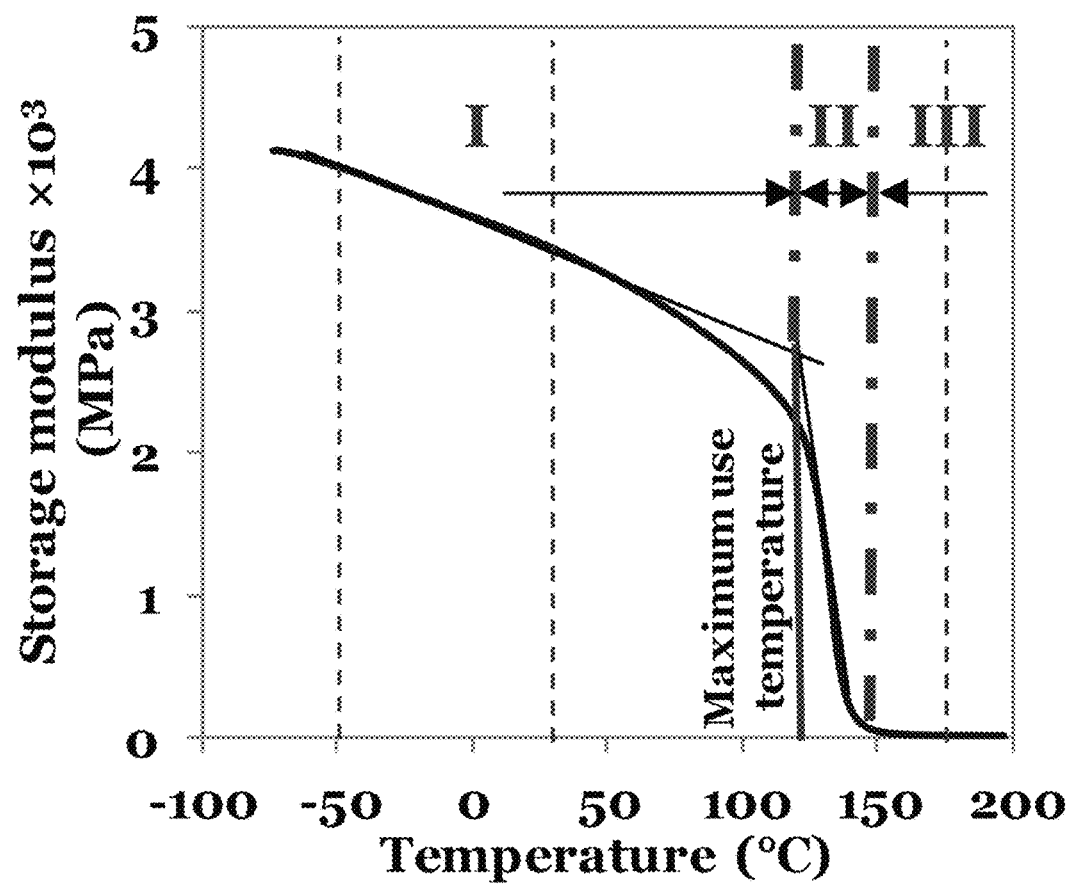
FIG. 4 depicts the variation of the storage modulus (E') as a function of temperature for a neat vinyl ester resin, with the dashed lines corresponding to −50° C., 30° C., and 175° C.

FIGS. 3A, 3B, and 3C depict representative graphs for storage modulus (E') variation with respect to temperature in the range −75° C. to 195° C. for VE220, VE320, and VE460 syntactic foams, respectively. Neat resin results are also plotted in each figure for the purposes of comparison. As a general characteristic, the graphs have three distinct regions as illustrated in FIG. 4. In Region I, E' slowly decreases with an increase in temperature. In Region II, the rate of E' reduction increases drastically. This region appears around $T_g$. In Region III, E' stabilizes to a very low value compared to that in Region I. The Region III defines the flow region where E' variation is negligible. The E' values at three representative temperatures, −50° C., 30° C. and 175° C. (marked in FIG. 4), are presented in Table 3 to demonstrate the extent of change with respect to temperature.

TABLE 3

| Specimen type | E' at −50° C. (MPa) | E' at 30° C. (MPa) | E' at 175° C. (MPa) |
| --- | --- | --- | --- |
| Neat VE | 4041 ± 44 | 3457 ± 42 | 11 ± 1 |
| VE220-30 | 2916 ± 76 | 2548 ± 66 | 50 ± 2 |
| VE220-40 | 2841 ± 54 | 2467 ± 34 | 72 ± 0 |
| VE220-50 | 3015 ± 42 | 2640 ± 44 | 124 ± 3 |
| VE220-60 | 2186 ± 65 | 1998 ± 37 | 178 ± 2 |
| VE320-30 | 3554 ± 45 | 3065 ± 53 | 46 ± 2 |
| VE320-40 | 3369 ± 49 | 2949 ± 55 | 71 ± 2 |
| VE320-50 | 3139 ± 73 | 2810 ± 98 | 126 ± 3 |
| VE320-60 | 2935 ± 55 | 2628 ± 63 | 213 ± 7 |
| VE460-30 | 4082 ± 24 | 3523 ± 36 | 51 ± 1 |
| VE460-40 | 3755 ± 143 | 3311 ± 120 | 85 ± 9 |
| VE460-50 | 3557 ± 206 | 3264 ± 186 | 137 ± 7 |
| VE460-60 | 3712 ± 94 | 3410 ± 36 | 248 ± 25 |

The E' for neat resin was higher than any measured composition of VE220 and VE320 syntactic foams at low temperatures (in Region I). However, VE460 syntactic foams exhibit E' comparable to that of neat resin. These trends are similar to the room temperature tensile and compressive modulus values previously reported for the corresponding syntactic foam compositions. An increase in Φ produced a decrease in E' for all types of microballoons. FIGS. 3A, 3B, and 3C show that the curves for different Φ of the same microballoon type cross over. The storage modulus of neat resin becomes the least after the cross over point. The cross over points shift to lower temperature as η increases. In Region III, E' was lowest for the neat resin, which was measured to be 76-96% lower than any produced syntactic foam.

The maximum use temperature is the temperature at which the storage modulus starts to decrease drastically. The intersection point of the tangents drawn to the Region I and Region II curves is defined as the maximum use temperature ($T_{max}$), as shown in FIG. 4. The values of the maximum use temperature are presented in Table 4. The $T_{max}$ was higher for the neat resin compared to any of the produced syntactic foams. Compared to the $T_{max}$ of the neat resin (122° C.), many syntactic foams have a $T_{max}$ below 96° C. The difference between E' calculated at room temperature and at maximum use temperature was found to be higher for neat resin (38%) than that of any of the produced syntactic foams, with a maximum reduction of 27% for VE460-30.

TABLE 4

| Specimen type | $T_{max}$ (° C.) | $T_g$ (° C.) |
| --- | --- | --- |
| Neat VE | 122 ± 1 | 132 ± 0 |
| VE220-30 | 96 ± 1 | 120 ± 0 |
| VE220-40 | 81 ± 10 | 123 ± 3 |
| VE220-50 | 89 ± 1 | 117 ± 2 |
| VE220-60 | 119 ± 0 | 133 ± 0 |
| VE320-30 | 90 ± 11 | 116 ± 5 |
| VE320-40 | 90 ± 9 | 120 ± 5 |
| VE320-50 | 89 ± 7 | 119 ± 2 |
| VE320-60 | 94 ± 3 | 126 ± 0 |
| VE460-30 | 96 ± 5 | 114 ± 4 |
| VE460-40 | 93 ± 3 | 115 ± 1 |
| VE460-50 | 120 ± 4 | 133 ± 2 |
| VE460-60 | 116 ± 9 | 130 ± 8 |

Figure 5A:
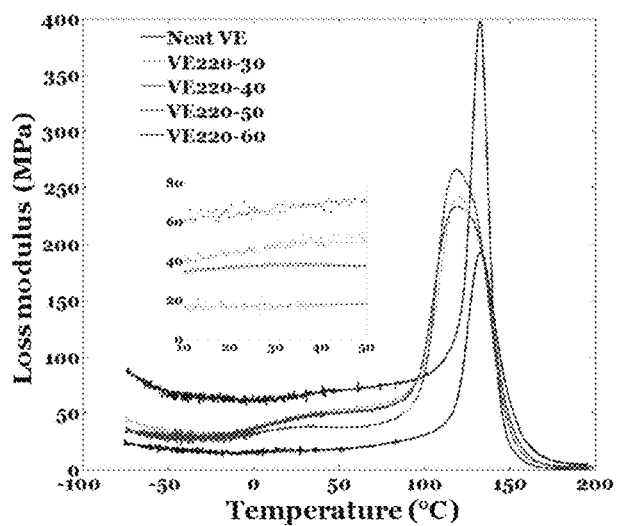
FIGS. 5A, 5B, and 5C depict the loss modulus of VE220, VE320, and VE460 syntactic foams, respectively, for a variety of microballoon volume fractions as a function of temperature, with the inset showing the temperature range of 10° C. to 50° C.
Figure 5B:
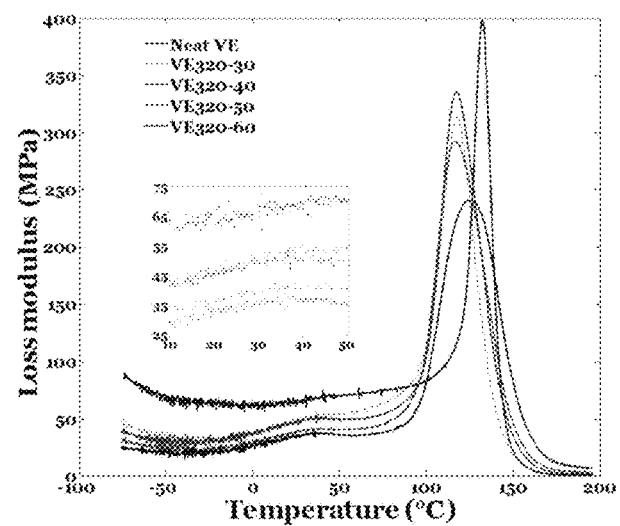
Figure 5C:
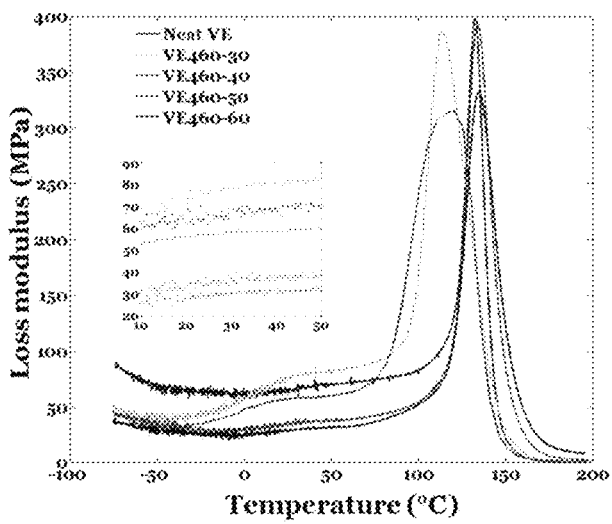

FIGS. 5A, 5B, and 5C depict representative sets of graphs for loss modulus (E") variation with respect to temperature in the range −75° C. to 195° C. for VE220, VE320, and VE460 syntactic foams, respectively. Neat resin results are also plotted in each figure for comparison. The glass transition temperature ($T_g$) may be obtained as the temperature corresponding to the maximum of the loss modulus curve and is presented in Table 4. $T_g$ for the neat resin was higher than many of the syntactic foams. $T_g$ of the syntactic foams increased with Φ and became nearly equal to that of the neat resin at Φ=0.6. The values of the maximum loss modulus for the neat resin and syntactic foams are presented in Table 5.

TABLE 5

| Specimen type | E" at 30° C. (MPa) | Maximum loss modulus ($E"_{max}$) (MPa) | Temperature at $E"_{max}$ (° C.) |
| --- | --- | --- | --- |
| Neat VE | 66 ± 2 | 402 ± 4 | 132 ± 0 |
| VE220-30 | 47 ± 1 | 235 ± 5 | 121 ± 1 |
| VE220-40 | 47 ± 2 | 234 ± 4 | 122 ± 2 |
| VE220-50 | 38 ± 1 | 262 ± 16 | 121 ± 1 |
| VE220-60 | 18 ± 1 | 187 ± 2 | 135 ± 1 |
| VE320-30 | 59 ± 6 | 288 ± 22 | 117 ± 3 |
| VE320-40 | 52 ± 4 | 292 ± 35 | 120 ± 2 |
| VE320-50 | 41 ± 1 | 271 ± 20 | 120 ± 2 |
| VE320-60 | 37 ± 2 | 231 ± 13 | 125 ± 2 |
| VE460-30 | 71 ± 10 | 371 ± 28 | 116 ± 3 |
| VE460-40 | 56 ± 3 | 335 ± 17 | 117 ± 3 |
| VE460-50 | 34 ± 3 | 350 ± 18 | 134 ± 2 |
| VE460-60 | 35 ± 9 | 328 ± 6 | 131 ± 8 |

At room temperature E" was lower for the produced syntactic foams than the neat resin. The lowest E" was observed for VE220-60 syntactic foams, which is 73% lower than the neat resin. An increase in Φ produced a decrease of E" for all types of microballoons. The $E"_{max}$ was higher for the neat resin when compared to various types of syntactic foams. An increase in Φ produced an increasing trend in $T_g$.

Figure 6A:
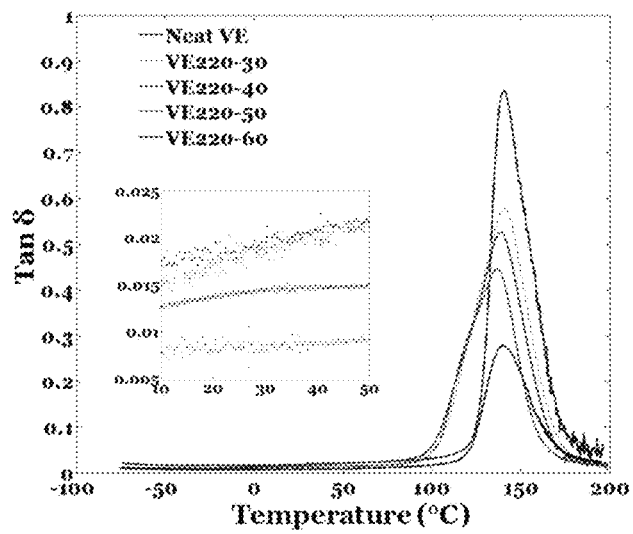
FIGS. 6A, 6B, and 6C depict the damping parameter of VE220, VE320, and VE460 syntactic foams, respectively, for a variety of microballoon volume fractions as a function of temperature, with the inset showing the temperature range of 10° C. to 50° C.
Figure 6B:
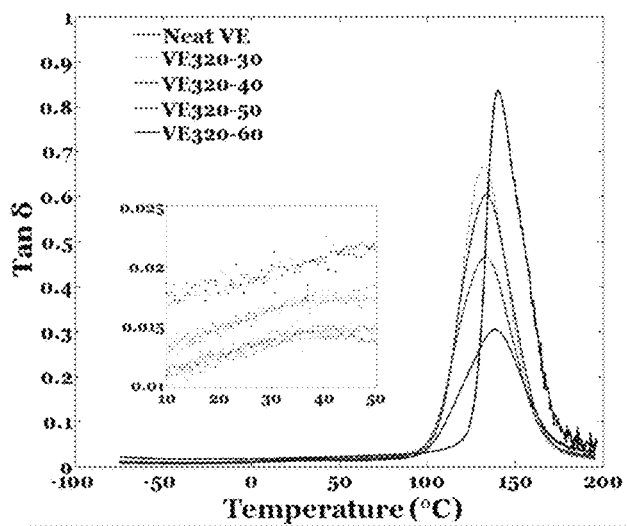
Figure 6C:
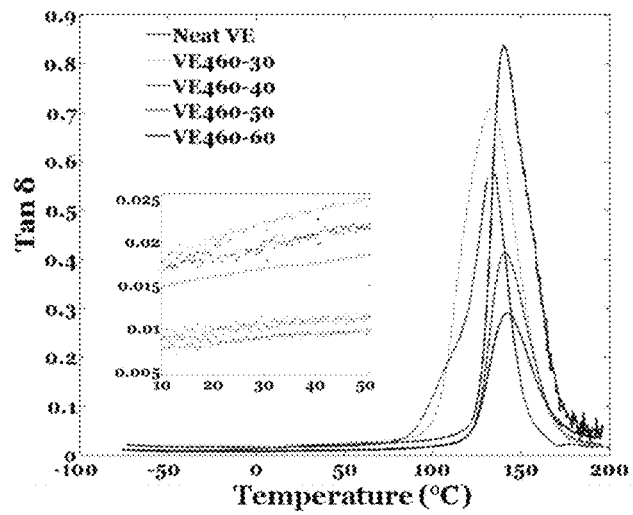

FIGS. 6A, 6B, and 6C depict representative sets of graphs for Tan δ variation for various syntactic foams and neat resin. Tan δ is defined as the ratio of the loss modulus to the storage modulus (E"/E') and is a measure of the damping capability of the material. An increase in Φ produced a decrease of the maximum and the room temperature values of Tan δ, as shown in Table 6. It may be observed from FIG. 6 that with an increase in Φ, the area under the Tan δ curve decreased. This indicates that the mechanical properties, and thus the stability, of the syntactic foams increase with increasing Φ at higher temperatures.

TABLE 6

| Specimen type | Tan δ at 30° C. (×10⁻³) | Maximum Tan δ (×10⁻³) | Temperature at Maximum Tan δ (° C.) |
|---|---|---|---|
| Neat VE | 19 ± 1 | 814 ± 13 | 142 ± 1 |
| VE220-30 | 18 ± 0 | 574 ± 9 | 141 ± 1 |
| VE220-40 | 19 ± 1 | 512 ± 8 | 139 ± 0 |
| VE220-50 | 15 ± 0 | 440 ± 4 | 136 ± 0 |
| VE220-60 | 9 ± 0 | 282 ± 2 | 141 ± 0 |
| VE320-30 | 19 ± 2 | 623 ± 37 | 134 ± 1 |
| VE320-40 | 18 ± 2 | 570 ± 39 | 136 ± 2 |
| VE320-50 | 15 ± 1 | 445 ± 26 | 135 ± 2 |
| VE320-60 | 14 ± 1 | 323 ± 17 | 138 ± 2 |
| VE460-30 | 20 ± 3 | 700 ± 5 | 134 ± 1 |
| VE460-40 | 17 ± 1 | 582 ± 22 | 133 ± 2 |
| VE460-50 | 10 ± 1 | 435 ± 45 | 142 ± 1 |
| VE460-60 | 10 ± 3 | 311 ± 48 | 139 ± 5 |

The combined effect of temperature and frequency on the properties of syntactic foams was characterized. The combined effect was studied for the neat resin and four compositions of syntactic foams: VE220-30, VE220-60, VE460-30 and VE460-60. These compositions were selected to account for the particles of the minimum and maximum density in the two extremities of volume fractions. The experiments were conducted in the frequency range of 1-100 Hz and in the temperature range of 30° C. to 140° C. TTS schemes may be used to develop master curves for the material over a wide range of temperatures and frequencies from a limited set of data.

Figure 7A:
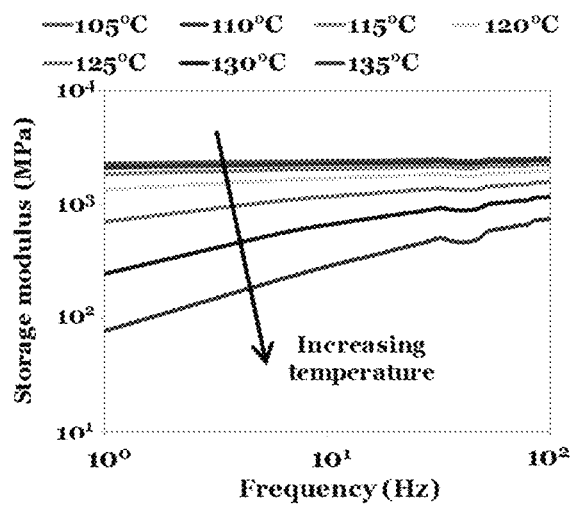
FIGS. 7A, 7B, and 7C depict the storage modulus of a neat vinyl ester resin obtained in the frequency range of 1-100 Hz for various temperatures, a master curve obtained using TTS at a reference temperature of 120° C., and the corresponding shift factors, respectively.
Figure 7B:
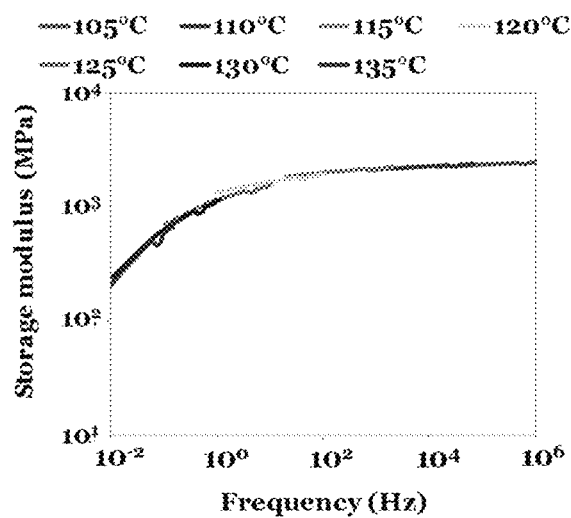
Figure 7C:
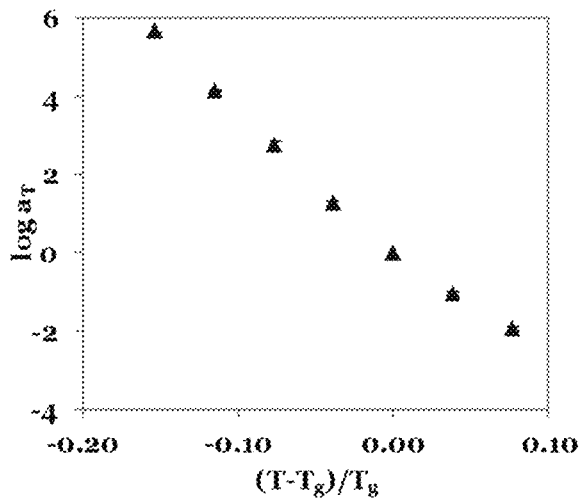
Figure 8A:
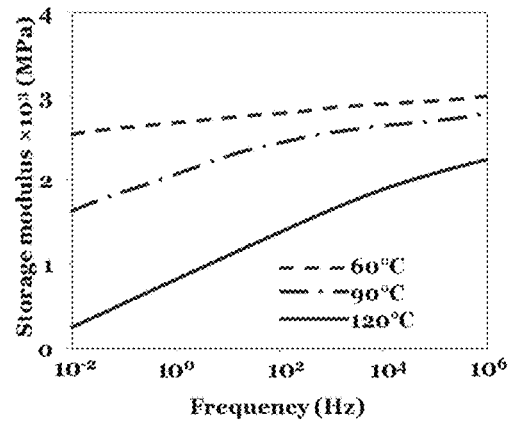
FIGS. 8A, 8B, 8C and 8D depict the master curves for VE220-30, VE220-60, VE460-30, and VE460-60 syntactic foams, respectively, at reference temperatures of 60° C., 90° C. and 120° C.
Figure 8B:
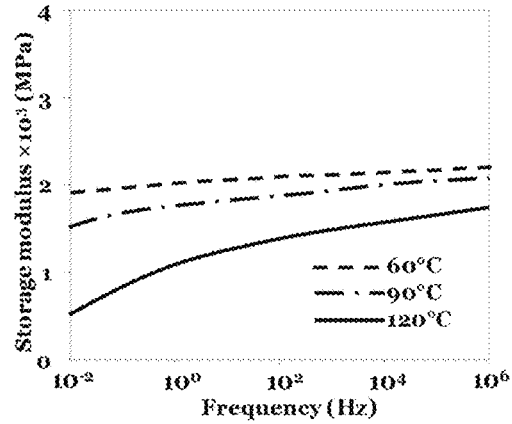
Figure 8C:
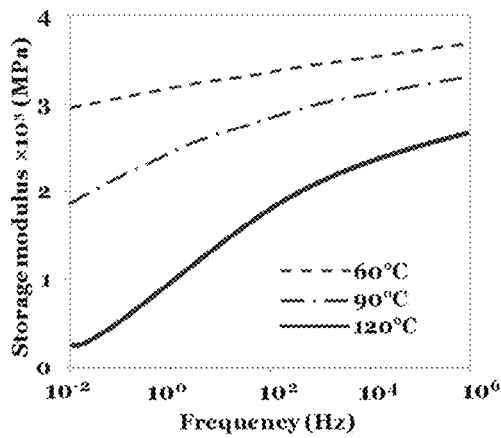
Figure 8D:
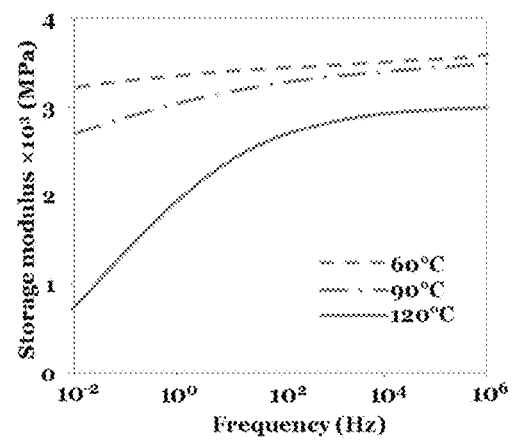

The E' values for the neat resin at different temperatures and frequencies are plotted in FIG. 7A. Two trends may be observed in this figure: (i) with increasing temperature the E' values decrease, which is similar to the trend observed in FIG. 3A, and (ii) the dependence of E' on the test frequency increases with temperature. The TTS principle may be used to construct master curves in frequency regions that are outside of the experimental frequency range (1-100 Hz). To construct a master curve, one of the curves in FIG. 7A is selected as the pivot and the remaining curves are shifted on the frequency axis towards the pivot curve until a continuous plot is obtained, which is the master curve. The reference temperature was selected as 120° C. for the pivot curve and the shift factor $a_T$ for each temperature was determined. FIG. 7B depicts the master curve for the neat resin at 120° C. The master curve is shown in the frequency range $10^{-2}$ to $10^6$ Hz, which is useful for many applications. In general, the master curve may be constructed for a wide range of frequencies using the available data. The corresponding shift factor values are presented in FIG. 7C. The shift factor values for all three specimens matched closely, as shown by the small error bars in FIG. 7C. Similar master curves may be constructed for any desired temperature by selecting an appropriate reference temperature for the pivot curve.

Figure 9A:
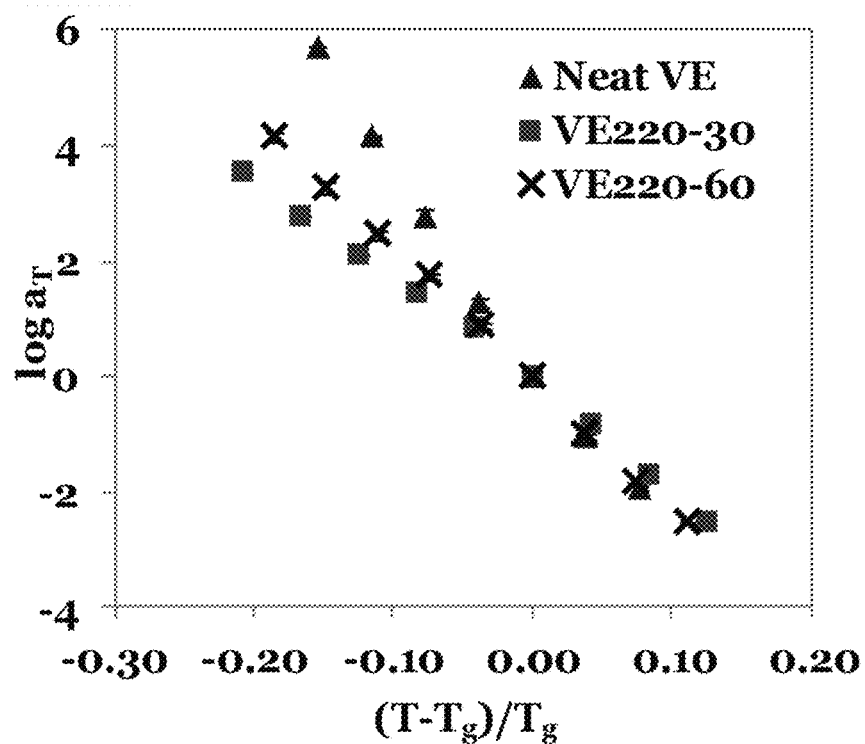
FIGS. 9A and 9B depict the TTS shift factors for VE220 and VE460 syntactic foams, respectively, used to obtain the master curves of FIG. 8.
Figure 9B:
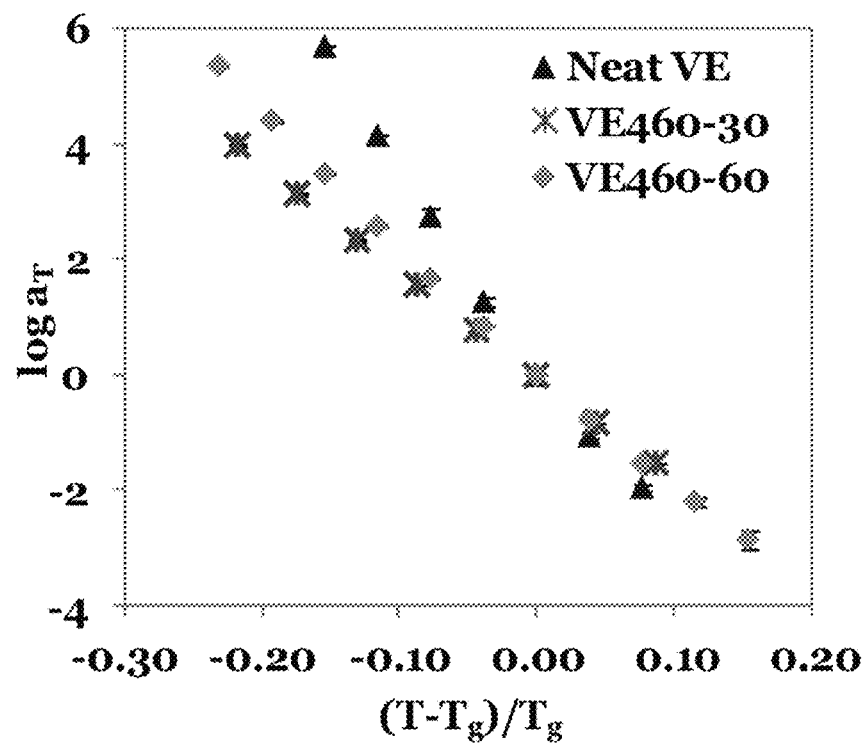

The same procedure was employed to develop master curves for VE220-30, VE220-60, VE460-30 and VE460-60 syntactic foams. Three specimens for each syntactic foam type were tested and the results were consistent. For simplicity, the curves for only one specimen of each type are presented here. The master curves are plotted in FIGS. 8A, 8B, 8C, and 8D for VE220-30, VE220-60, VE460-30 and VE460-60 syntactic foams, respectively, at reference temperatures of 60° C., 90° C. and 120° C. The curves demonstrate that as the frequency is increased the sensitivity of E' for the test frequency reduces. The sensitivity of E' to frequency becomes negligible after 1 MHz frequency for all materials tested. The calculated shift factors for syntactic foams VE220 and VE 460 are plotted in FIGS. 9A and 9B, respectively. The shift factors are independent of the reference temperature of the pivot curve. The shift factors are of the same order for vinyl ester and the produced syntactic foams, as shown in FIGS. 9A and 9B.

The syntactic foam density may decrease with (i) decreasing wall thickness of the microballoons, (ii) increasing microballoon volume fraction, and (iii) increasing matrix porosity. Either the individual effects of these parameters or their combined effects on density may produce an identifiable trend with the viscoelastic properties of syntactic foams. The observed experimental trends are further discussed below.

The E' variation with respect to temperature for various syntactic foams was investigated, as reported in Table 3. E' may increase with the wall thickness of the microballoon for a given Φ. The variation with respect to the Φ is not the same for all the microballoon types. Thin walled microballoons may produce a decrease in E' with an increase in Φ while thicker walled microballoons may produce an increase in E' with an increase in Φ. The E' values at room temperature for the syntactic foams in Table 3 demonstrate a linear trend with respect to the syntactic foam density. Identifying this trend allows a combination of microballoon wall thickness and Φ to be used to obtain a range of syntactic foam compositions with the same density. This provides a flexible approach to tailor the viscoelastic properties of syntactic foams within the available material parameters.

Syntactic foams may be stiffened with the addition of thicker walled particles, with the opposite trend observed in the case of thin walled particle reinforcement. These trends have also been observed for the tensile and the flexural modulus of the syntactic foams tested at room temperature. The stiffening or softening effects with increasing Φ may depend on the ratio of microballoon modulus to matrix modulus. Hollow particles include an air void inside the glass shell. Therefore, the effective modulus of a hollow particle ($\bar{E}$) is lower than the modulus of the glass material. For hollow particles, $\bar{E}$ can be estimated by $$\bar{E} = \frac{E_g(1-2v)(1-\eta^3)}{(1-2v) + \left(\frac{1+v}{2}\right)\eta^3} \qquad (3)$$

where $E_g$ is the modulus of the glass material (60 GPa) and v is the Poisson's ratio of the glass material (0.21). In addition, density of the glass is estimated as 2540 kg/m³. The average η values calculated from Equation (1), based on the nominal true density of particles, are presented in Table 1. The estimates of $\bar{E}$ for S22, S32, and K46 microballoons are 2.7 GPa, 4.0 GPa, and 5.9 GPa, respectively. These theoretical values assume that the particles are defect free. The presence of defects within the particles may further reduce the modulus values. The elastic modulus of the neat vinyl ester is 3.4 GPa. Therefore, it may be predicted that incorporation of the S22 particles will produce a softening effect in the vinyl ester matrix, incorporation of the S32 particles will produce a mild stiffening or no effect in the vinyl ester matrix, and incorporation of the K46 particles will produce a stiffening effect in the vinyl ester resin. These predicted results are confirmed by the experimental results for E'.

Figure 10:
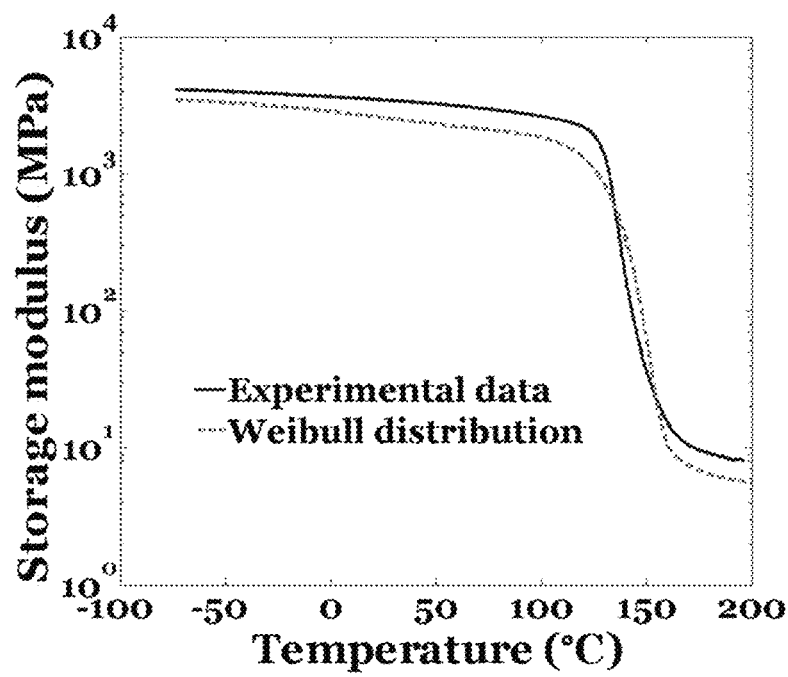
FIG. 10 depicts a comparison of a Weibull distribution with the experimental data for a neat vinyl ester resin.

The storage modulus variation with respect to temperature has been studied for many polymers including amorphous and crystalline thermoplastics and thermosets. The stiffness variation has been modeled with respect to temperature. This model accounts for the relaxation of the polymer by quantifying the breakage of the secondary bonds. The model is governed by a Weibull distribution which estimates the bond rupture based on the parameters ($m_i$) referred to as Weibull moduli corresponding to the statistics of bond breakage. These parameters are dependent on various factors such as degree of cross-linking, molecular weight and crystallinity of the polymer. Based on the material stiffness transitions with respect to temperature, the general equation for the Weibull distribution may be expressed as $$E' = (E'_1 - E'_2)\exp\left(-\left(\frac{T}{T_1}\right)^{m_1}\right) + (E'_2 - E'_3)\exp\left(-\left(\frac{T}{T_2}\right)^{m_2}\right) + E'_3 \exp\left(-\left(\frac{T}{T_3}\right)^{m_3}\right) \quad (4)$$

where T corresponds to the temperature, $T_1$, $T_2$ and $T_3$ correspond to the instantaneous reference temperatures which are well below $T_g$, equal to $T_g$ and in the flow region above $T_g$, respectively. $E'_1$, $E'_2$ and $E'_3$ correspond to the storage modulus values at each of the three reference temperatures and $m_1$, $m_2$ and $m_3$ correspond to the Weibull coefficients that govern the decrease in the modulus due to the secondary bond rupture at the three reference temperatures. In the current study, $T_1$ and $T_3$ are maintained constant at arbitrarily chosen temperatures 27° C. and 170° C., respectively, for all syntactic foams and the neat resin. The Weibull coefficients $m_1$ (corresponding to the low temperature region) and $m_3$ (corresponding to the flow region above $T_g$) are selected as 5 and 1, respectively. Parametric studies were conducted to arrive at the selected values of $m_1$ and $m_3$. Curve fitting was employed to obtain the value for $m_2$ that provides the best fit with the experimental dataset. The best-fit between the Weibull curve and the experimental data for neat resin is obtained at $m_2$=30, as shown in FIG. 10. It may be observed in FIG. 10 that there is some variation between the experimental data and Weibull curve, which may be attributed to the cross-linked structure of thermosetting polymers. Unlike thermoplastic polymers, the molecular chains are more restricted in thermosetting polymers due to the presence of cross-links. Therefore, the estimation of the bond breakage by the Weibull coefficients in thermosetting polymers may be underestimated.

Figure 11:
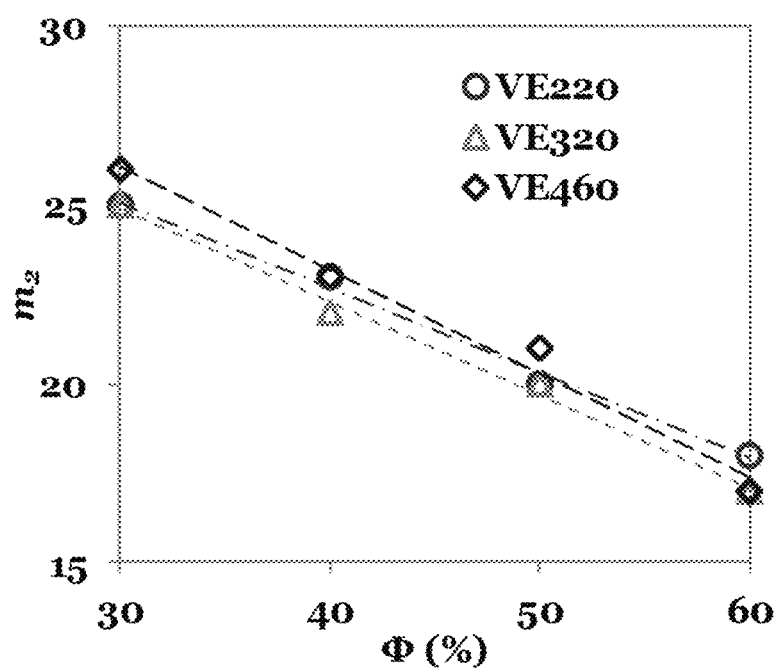
FIG. 11 depicts a variation of the Weibull parameter $m_2$ as a function of microballoon volume fraction $\Phi$ for various syntactic foams.

A similar calculation was conducted to estimate the $m_2$ values for syntactic foams. Table 7 lists the E' values at the three reference temperatures that are used as inputs in equation (4), with $E'_1$ selected at a constant temperature of 27° C., $E'_2$ selected at Tg as provided in Table 4, and $E'_3$ selected at a constant temperature of 170° C. A parametric study was performed to estimate the Weibull coefficient $m_2$, which is plotted in FIG. 11. It may be observed that $m_2$ decreases with increase in Φ. This result corroborates the observed effect of variation of carbon black content on polybutadiene and shows that with an increasing reinforcement content (0-37.5 wt. % range), the Weibull parameter decreased up to 50%. It was observed that Φ has a stronger influence on E' than the microballoon wall thickness. Additionally, if the $m_2$ values are plotted with respect to the syntactic foam density they fit along a straight line. These trends illustrate that with the availability of only a small set of parameters, the behavior of a wide variety of syntactic foam compositions may be determined.

TABLE 7

| Specimen type | $E'_1$ (MPa) | $E'_2$ (MPa) | $E'_3$ (MPa) |
| --- | --- | --- | --- |
| Neat VE | 2936 | 1616 | 8 |
| VE220-30 | 2723 | 941 | 136 |
| VE220-40 | 2451 | 878 | 133 |
| VE220-50 | 2908 | 979 | 127 |
| VE220-60 | 2145 | 973 | 202 |
| VE320-30 | 3085 | 1155 | 48 |
| VE320-40 | 2997 | 1057 | 71 |
| VE320-50 | 2985 | 1117 | 133 |
| VE320-60 | 2785 | 1093 | 232 |
| VE460-30 | 3556 | 1188 | 53 |
| VE460-40 | 3485 | 1028 | 76 |
| VE460-50 | 3285 | 1634 | 148 |
| VE460-60 | 3674 | 2040 | 245 |

Figure 12:
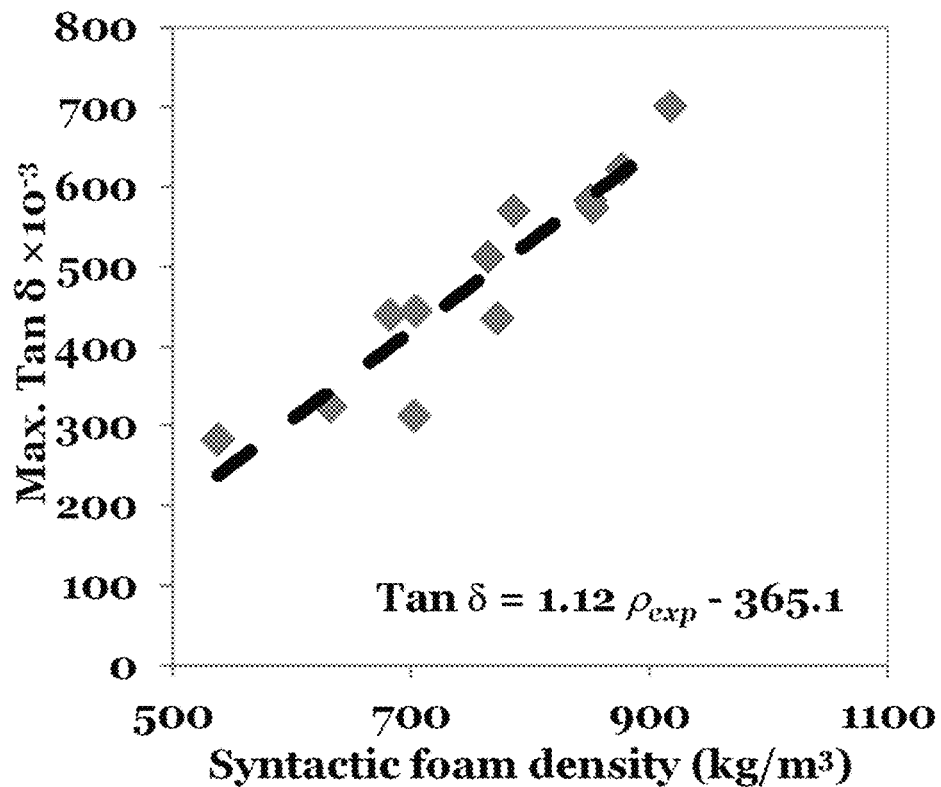
FIG. 12 depicts a variation in maximum Tan δ as a function of syntactic foam density.

The damping parameter Tan δ exhibits a decrease in a maximum with increasing Φ. This effect may be related to the brittle nature of the microballoons and the viscoelastic nature of the polymeric matrix material. These effects are similar to those the previously reported on the dynamic mechanical behavior of syntactic foams at room temperature. Since Tan δ presents a relationship between E' and E", it is also analyzed with respect to the syntactic foam density in FIG. 12. The maximum Tan δ values fit along a straight line in this figure for many syntactic foams. This linear relationship may be useful in analyzing the weight saving potential through the use of syntactic foams in applications that are based on the damping characteristics, which contribute to increased $T_g$.

$T_g$ of the neat resin was higher than the syntactic foams analyzed herein. This may be related to the lower specific heat capacity of glass compared to the neat resin. An increase in $T_g$ may be observed with increasing Φ, as reported in Table 4. A similar trend has been observed in the $T_g$ of epoxy matrix syntactic foams. The increase in $T_g$ with increasing Φ may be attributed to the reduction in the mobility of polymer chains due to the interfacial bonding between microballoons and resin. The microballoon-matrix interfacial area increases with increasing Φ. A similar trend has been observed in other particle reinforced composites. For example, a silica filled polymeric matrix composite exhibited a stiffening effect adjacent to the filler particle-matrix interface, which may be responsible for an increased $T_g$.

Figure 13:
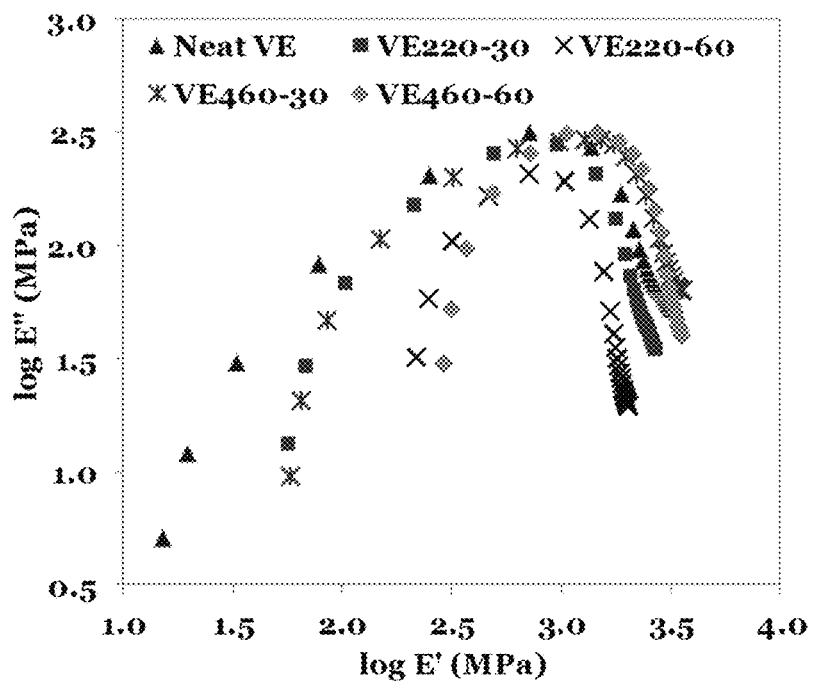
FIG. 13 depicts the Cole-Cole plot of syntactic foams and a neat vinyl ester resin.

A Cole-Cole plot may be used to interpret trends observed in TTS curves. This plot between log E" and log E' may show a semi-circular curve for homogeneous materials. FIG. 13 depicts the Cole-Cole plot for the neat vinyl ester resin and syntactic foams. The curves for the neat resin and syntactic foams exhibit similar trends, and demonstrate the applicability of TTS for syntactic foams. The imperfect semi-circle observed in FIG. 13 indicates a good interfacial bonding between particles and the matrix. Strong interfacial bonding may be attributed to similar deviations from the semi-circular shape of Cole-Cole plots in composites.

Figure 14:
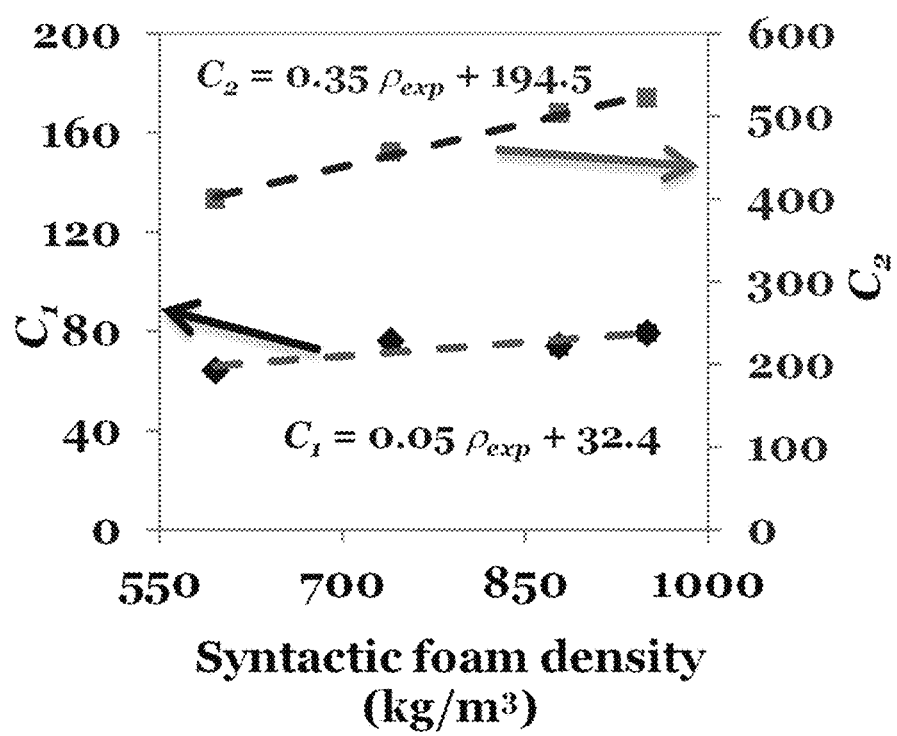
FIG. 14 depicts constants $c_1$ and $c_2$ of equation (5) plotted against syntactic foam density.

Further analysis of TTS results may be conducted by the William-Landel-Ferry (WLF) equation $$\log a_T = \frac{-c_1(T - T_0)}{c_2 + (T - T_0)} \quad (5)$$

where $T_0$ is the reference temperature for which the master curve is constructed (60° C.) and $c_1$ and $c_2$ are constants calculated from the slope and the y-intercept of the $(T-T_0)/\log a_T$ versus $(T-T_0)$ plot. The values of $c_1$ and $c_2$ are calculated as 96.8 and 357.7, respectively, for the neat vinyl ester resin. The values of $c_1$ and $c_2$ for various syntactic foams are plotted in FIG. 14. Although microballoons of different wall thickness and Φ are used in the four syntactic foams, both constants $c_1$ and $c_2$ exhibit a linearly increasing trend with the increasing syntactic foam density. The linear trend may allow the engineering of properties of syntactic foams to produce desired properties.

Figure 15:
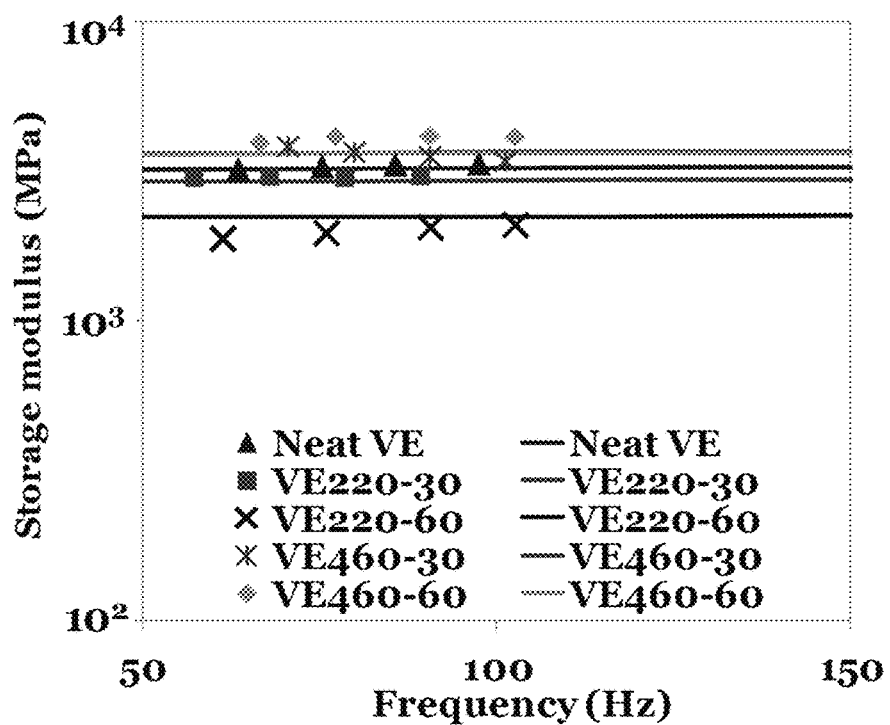
FIG. 15 depicts the storage modulus for syntactic foams and a neat vinyl ester resin matrix as a function of frequency, with the lines extrapolated from the experimental data.

The master curves obtained for the syntactic foams were compared with previously reported data. The room temperature dynamic mechanical properties of syntactic foams were previously investigated by using the vibration response of cantilever beam specimens subjected to impulse excitation using an instrumented hammer. The storage modulus values were calculated from these results at certain frequencies, as plotted in FIG. 15. The figure also contains lines for the E' values obtained herein at 30° C. temperature. The testing herein was conducted within the frequency range of 1-100 Hz, and the values were extrapolated in the 100-150 Hz range to cover the last data point. A maximum variation of ±14% was observed in both sets of results for all four types of syntactic foams and the neat resin.

The experimental results support the following general conclusions. The room temperature (30° C.) storage modulus of syntactic foams may increase with an increase in the wall thickness of the microballoons. A stiffening effect may be observed for an increase in the volume fraction of thick walled microballoons and a decrease in the volume fraction of thin walled microballoons. The room temperature storage modulus and Tan δ may vary linearly with the density of syntactic foams. The presence of glass microballoons may increase the retention of mechanical properties of syntactic foams at temperatures beyond $T_g$. The $T_g$ may increase with an increasing microballoon volume fraction. The addition of microballoons may produce a 14-66% decrease in Tan δ compared to the Tan δ of the neat resin, as well as an increase in the storage modulus of the syntactic foams post $T_g$. Time temperature superposition (TTS) may be employed to develop master curves over wide temperature and frequency ranges from the tests conducted in the frequency range 1-100 Hz. A Cole-Cole plot and the WLF equation may be employed to analyze the data obtained from the temperature and frequency dependent testing.

Electrical Properties

Vinyl ester-glass microballoon (GMB) syntactic foams were characterized for dielectric properties with a specific focus on understanding the relation of the volume fraction of the microballoons, $\Phi_{mb}$, and hollow particle wall thickness to the dielectric constant of the syntactic foams. In addition, theoretical models were developed to predict the dielectric constant of syntactic foams. The Maxwell-Garnett and Jayasundere-Smith (J-S) equations, applicable to solid particle filled composites, were modified to include the hollow particle wall thickness. These theoretical predictions were validated with experimental results. The models are used to conduct parametric studies to understand the weight saving potential of syntactic foams in applications where the dielectric constant is the primary consideration.

Glass microballoons and a vinyl ester resin were employed to fabricate syntactic foam slabs for the purpose of studying electrical properties. According to one embodiment, neat vinyl ester resin and GMBs were measured in appropriate proportions and mixed in a beaker. To the uniform mixture, a hardener was added and continuously stirred. The resulting slurry was poured into aluminum molds coated with a lubricant and allowed to cure at room temperature for at least 24 h.

Figure 16:
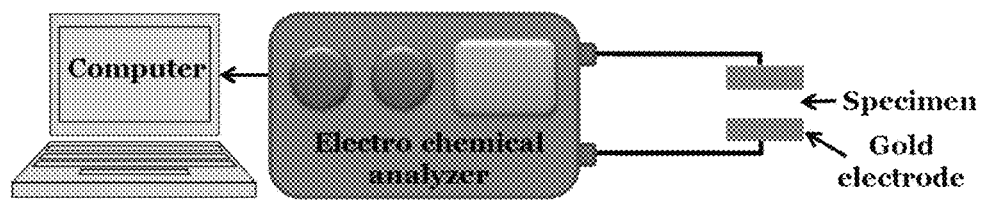
FIG. 16 is a schematic representation of the experimental setup used to measure the impedance of syntactic foams.

The electrical impedance was measured using a CH Instruments 700D potentiostat by the AC impedance method, as schematically represented in FIG. 16. The experiments were conducted in a frequency range of $10^{-2}$-$10^6$ Hz, with an applied AC wave amplitude of 500 mV. According to one embodiment, a specimen size of 18×14×1 mm was used in performing the experiments. The specimens were cut using a low speed precision diamond blade saw to ensure that the surfaces were parallel to each other. Five specimens were tested for each composition type of syntactic foams and the average values along with the standard deviations are reported.

Figure 17A:
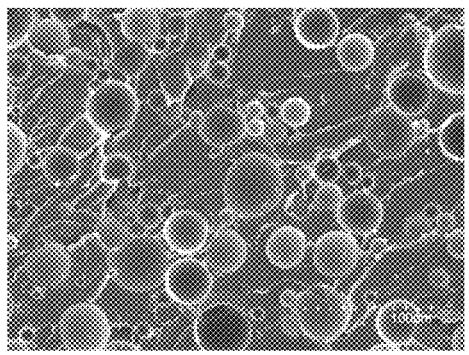
FIGS. 17A and 17B are scanning electron micrographs of vinyl ester syntactic foams containing 460 type microballoons at volume fractions of 0.3 and 0.6, respectively.
Figure 17B:
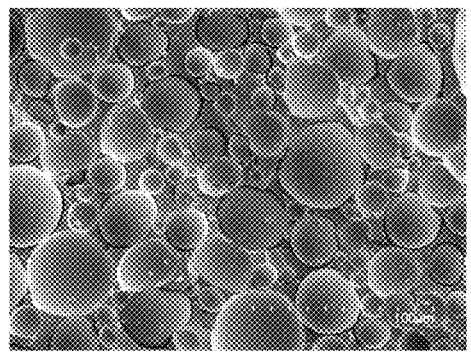

GMBs of three different nominal true particle densities (220 kg/m³, 320 kg/m³ and 460 kg/m³) were used in four different volume fractions (30%, 40%, 50% and 60%) to fabricate twelve types of syntactic foams. The scanning electron micrographs of 460 type microballoon reinforced vinyl ester matrix syntactic foams containing 30% and 60% are shown in FIGS. 17A and 17B. The radius ratio of the microballoons may be calculated using previously described equation (1). Further, the radius ratio may be related to the GMB wall thickness (w) as $$w = r_o(1-\eta) \quad (6)$$

An increasing value of η refers to a decreasing hollow particle wall thickness. The GMB properties, including radius ratio, are provided in Table 8. These GMBs have been extensively characterized in previous studies and information on the measured average diameter, size distribution, and density are widely available. These experimental values are used in herein for determining the GMB parameters.

TABLE 8

| Specimen type | Mean particle diameter (μm) | Wall thickness (μm) | Radius ratio (η) | Theoretical density (kg/m³) | Experimental density (kg/m³) | Matrix porosity (vol. %) |
|---|---|---|---|---|---|---|
| VE220-30 | 35 | 0.52 | 0.970 | 878 | 839 | 4.5 |
| VE220-40 | | | | 784 | 774 | 1.2 |
| VE220-50 | | | | 690 | 676 | 2.0 |
| VE220-60 | | | | 596 | 570 | 4.4 |
| VE320-30 | 40 | 0.88 | 0.956 | 908 | 888 | 2.2 |
| VE320-40 | | | | 824 | 787 | 4.5 |
| VE320-50 | | | | 740 | 712 | 3.8 |
| VE320-60 | | | | 656 | 633 | 3.6 |
| VE460-30 | 40 | 1.29 | 0.936 | 950 | 937 | 1.4 |
| VE460-40 | | | | 880 | 843 | 4.3 |
| VE460-50 | | | | 810 | 782 | 3.4 |
| VE460-60 | | | | 740 | 716 | 3.3 |

The specimen nomenclature starts with VE representing vinyl ester resin, followed by three digit true particle density and two digits of microballoon volume fraction. The entrapped air porosity in the matrix may be calculated by using previously described equation (2). The theoretical density calculated using the rule of mixtures and the experimentally measured density of syntactic foams are reported in Table 8. The estimated matrix porosity is low and is between 1 and 4.5 vol. % for most syntactic foam slabs.

The impedance obtained from the experiment is a complex quantity, containing the real (resistance, R) and the imaginary (reactance, $X_c$) parts and may be defined $$|Z| = \sqrt{R^2 + X_c^2} \quad (7)$$

The potentiostat provides measurements of these quantities. The phase angle may be given as $$\phi = \tan^{-1}\left(\frac{X_c}{R}\right). \quad (8)$$

The phase angle is found to be around −90°, which indicates the capacitive nature of the neat resin. The capacitance may be obtained as $$C = \frac{1}{2\pi f X_c}. \quad (9)$$

The dielectric constant may be obtained from the calculated capacitance as $$\varepsilon = \frac{Ct}{\varepsilon_0 A}. \quad (10)$$

The values of t the thickness of the sample, A the contact area, and the dielectric constant of a vacuum $\varepsilon_0$ are taken as $10^{-3}$ m, $25.2 \times 10^{-5}$ m$^{-2}$ and $8.854 \times 10^{-12}$ F/m, respectively.

Figure 18:
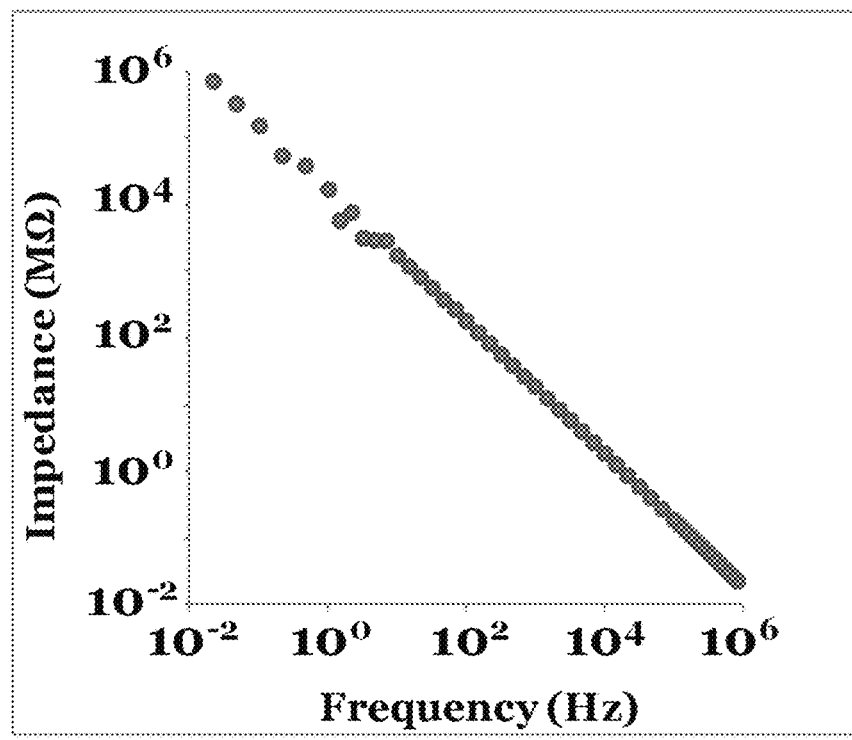
FIG. 18 depicts the variation of the impedance of a neat vinyl ester resin as a function of frequency.

First, the impedance of the neat vinyl ester resin employed as the matrix in the syntactic foams was measured. The variation of impedance with respect to frequency for the vinyl ester resin is depicted in FIG. 18. The impedance was found to decrease with increasing frequency across the selected range. The impedance values were used to calculate the dielectric constant of the neat vinyl ester resin at various frequencies.

Next, syntactic foams were tested in a similar manner and their dielectric constants were calculated from the experimental results. The impedance-frequency plots of the syntactic foams exhibit characteristics similar to the neat resin. These plots may be used to determine the dielectric constant at various frequencies of interest.

Figure 19:
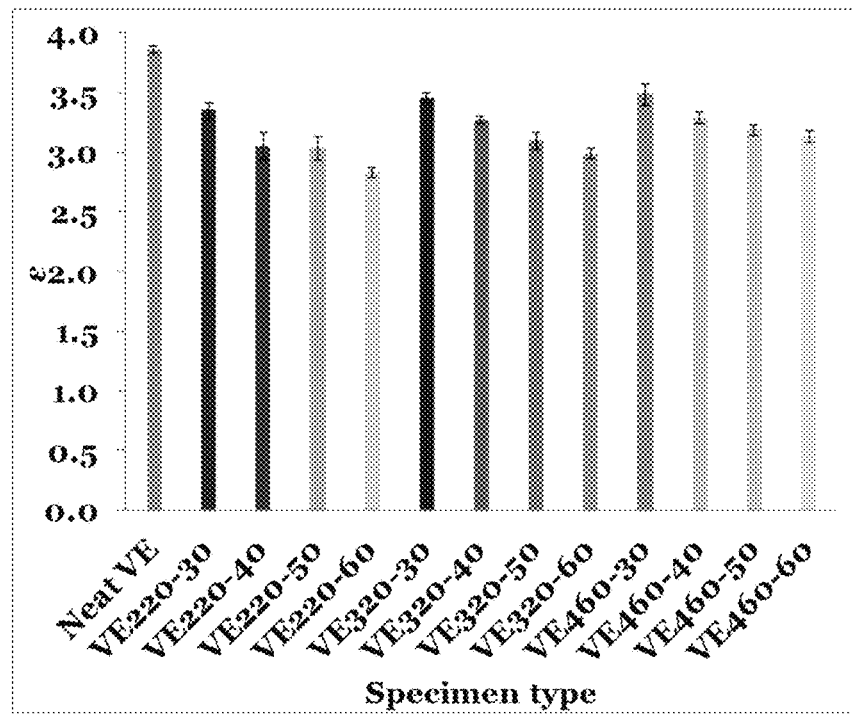
FIG. 19 depicts the experimentally measured dielectric constant for a neat vinyl ester resin and various syntactic foams.
Figure 20:
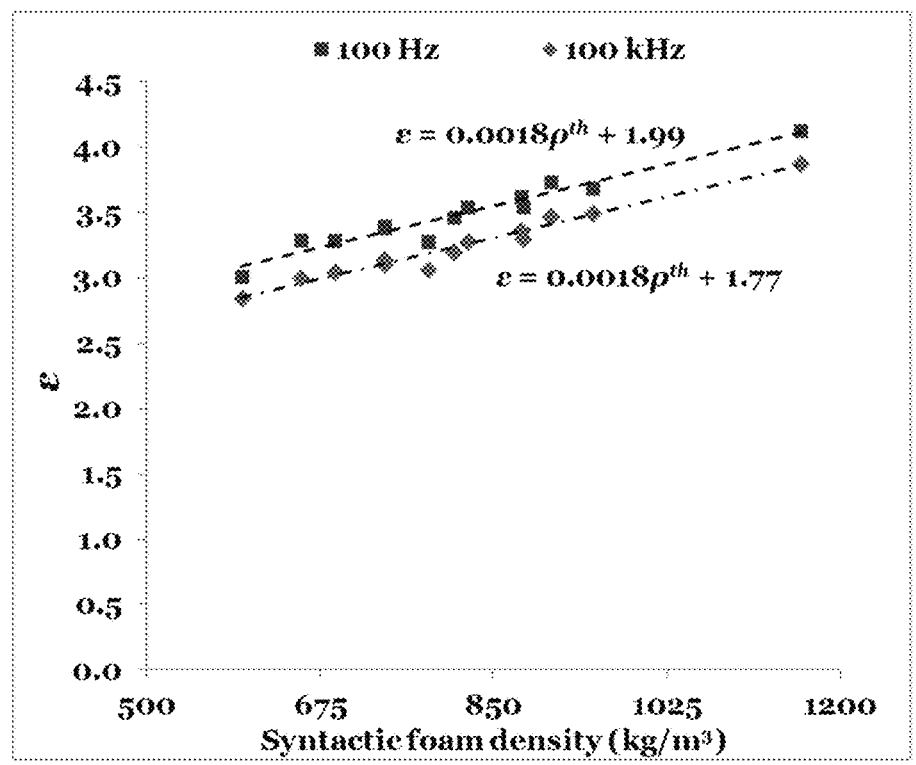
FIG. 20 depicts the variation of the experimentally measured dielectric constant at 100 Hz and 100 kHz as a function of syntactic foam density.

The dielectric constants of the neat resin and the syntactic foams at a representative frequency of 100 kHz are presented in FIG. 19. As a general trend, the dielectric constant of the syntactic foams is lower than that of the neat resin. It is also observed that GMB volume fraction has a prominent effect on the dielectric constant of the syntactic foams. The dielectric constant of the syntactic foams decreases with increasing GMB volume fraction. This relationship may be produced because the air porosity volume fraction increases with GMB volume fraction, and air has a lower dielectric constant than that of the matrix resin and GMB material (glass). The plot of the dielectric constant with respect to syntactic foam density depicted in FIG. 20 demonstrates that both η and GMB volume fraction affect the density of the syntactic foams. The neat resin had the highest density observed in the experimental data set. The dielectric constant varied almost linearly with respect to the syntactic foam density. FIG. 20 includes the dielectric constant at frequencies of 100 Hz and 100 kHz. In both cases the slope of the line is the same.

The syntactic foam density is dependent on both the GMB volume fraction and η. The individual effect of these parameters may be better understood by theoretical analysis. Although the interfacial bonding between GMB and vinyl ester is expected to play a role in the measured dielectric constant, this parameter is not included in the study. The interfacial bonding characteristics may be assumed to be the same for all syntactic foams for the sake of simplicity. In addition, the mean radius may be the same for all types of GMBs used in syntactic foams, indicating that the syntactic foams having the same volume fraction of different types of GMBs will have the same interfacial area and the effect of bonding characteristics will also be the same. Hence, the effect of GMB volume fraction and η is evaluated through theoretical models. In addition, including interfacial bonding as a parameter in mathematical models would require quantitative information, but quantitative information on interfacial bonding is not presently available. The interfacial bonding may include the combined effects of chemical bonding, mechanical interlocking and interfacial friction.

Figure 21:
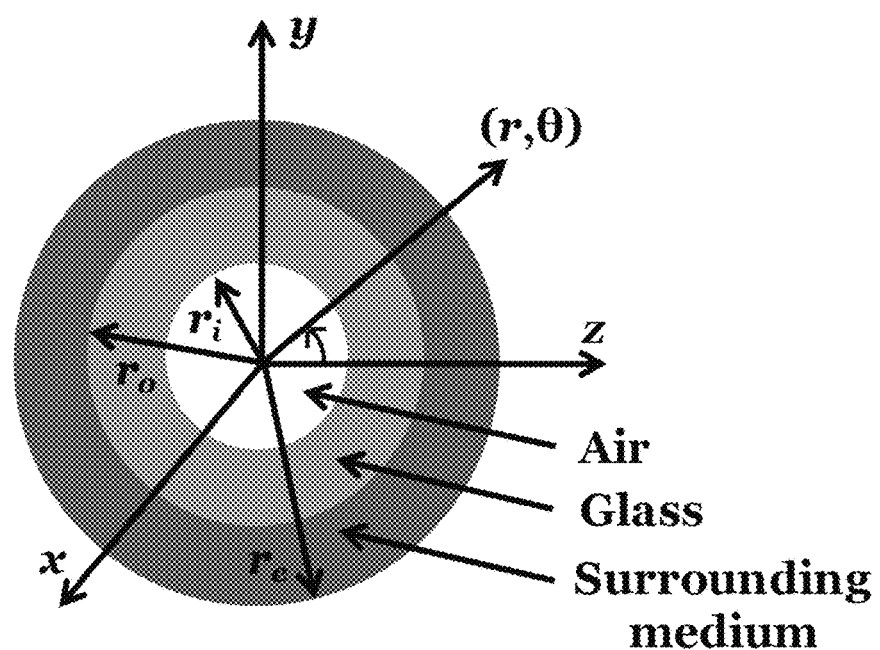
FIG. 21 is a schematic representation of a hollow glass microballoon.

Estimation of the dielectric constant of hollow particles, which comprise a thin shell filled with air, may be the first step in theoretically obtaining the effective dielectric constant of syntactic foams. In order to find a closed form expression for the dielectric constant of GMBs, Maxwell's theory may be utilized. The polarization of GMBs may be equated to the polarization of an equivalent sphere and the dielectric constant of GMB may be obtained as follows. The potential ψ of the GMB may be obtained by solving the Laplace equation in polar coordinates, as depicted in FIG. 21, given by the equation $$\nabla^2 \psi = 0. \quad (11)$$

The solution of the Laplace equation may be obtained in the form $$\psi(r, \theta) = \sum_{n=o}^{\infty} (a_n r^{-(n+1)} + b_n r^n) P_n(\cos \theta). \quad (12)$$

where $P_n(\cos \theta)$ is the $n^{th}$ order Legendre polynomial and $a_n$ and $b_n$ are constants. Taking into account the axial symmetry of the sphere, the potential may be given by $$\psi_1(r, \theta) = \sum_{n=1}^{\infty} (D_n r^n) P_n(\cos \theta) \quad (r \leq r_i) \quad (13)$$

$$\psi_2(r, \theta) = \sum_{n=1}^{\infty} (E_n r^{-(n+1)} + G_n r^n) P_n(\cos \theta) \quad (r_i \leq r \leq r_o) \quad (14)$$

$$\psi_3(r, \theta) = \sum_{n=1}^{\infty} (H_n r^{-(n+1)} + I_n r^n) P_n(\cos \theta) \quad (r_o \leq r \leq r_e) \quad (15)$$

$$\psi_4(r, \theta) = -e_0 r P_1(\cos \theta) + \sum_{n=1}^{\infty} J_n r^{-(n+1)} P_n(\cos \theta) \quad (r_e \leq r). \quad (16)$$

The constants $D_n$, $E_n$, $G_n$, $H_n$, $I_n$, and $J_n$ may be found by applying the following boundary conditions and utilizing the orthogonality property, given by $$\psi_1(r_i, \theta) = \psi_2(r_i, \theta) \quad (17a)$$

$$\psi_2(r_o, \theta) = \psi_3(r_o, \theta) \quad (17b)$$

$$\psi_3(r_e, \theta) = \psi_4(r_e, \theta) \quad (17c)$$

$$\varepsilon_a (\partial_r \psi_1)_{r=r_i} = \varepsilon_g (\partial_r \psi_2)_{r=r_i} \quad (18a)$$

$$\varepsilon_g (\partial_r \psi_2)_{r=r_o} = \varepsilon_e (\partial_r \psi_3)_{r=r_o} \quad (18b)$$

-continued $$\varepsilon_e(\partial_r \psi_3)_{r=r_e} = (\partial_r \psi_4)_{r=r_e} \quad (18c)$$

$$\int_{\theta=0}^{\pi} P_n(\cos\theta) P_m(\cos\theta) \sin\theta d\theta = \frac{2}{(2m+1)} \delta_{m,n} \quad (19)$$

where $\delta_{m,n}$ is the Kronecker delta function. Applying the above boundary conditions the value of the constant $J_1$ may be $$J_1 = \left[ \frac{(\varepsilon_e - 1)}{(\varepsilon_e + 2)} r_e^3 K - \frac{(2\varepsilon_e + 1) r_o^3 L}{(\varepsilon_e + 2)(2\varepsilon_e + \varepsilon_g)} \right] Se_0 \quad (20)$$

where the constants K, L and S are represented by $$K = \left[ 1 + 2 \frac{(\varepsilon_e - \varepsilon_g)(\varepsilon_g - \varepsilon_a)}{(2\varepsilon_e + \varepsilon_g)(2\varepsilon_g + \varepsilon_a)} \frac{r_i^3}{r_o^3} \right]$$

$$L = \left[ (\varepsilon_e - \varepsilon_g) + \frac{(\varepsilon_e + 2\varepsilon_g)(\varepsilon_g - \varepsilon_a)}{(2\varepsilon_g + \varepsilon_a)} \frac{r_i^3}{r_o^3} \right]$$

$$S = \left[ 1 + 2 \frac{(\varepsilon_e - \varepsilon_g)(\varepsilon_g - \varepsilon_a)}{(2\varepsilon_e + \varepsilon_g)(2\varepsilon_g + \varepsilon_a)} \frac{r_i^3}{r_o^3} - \right.$$
$$\left. 2 \frac{(\varepsilon_e - 1)(\varepsilon_e - \varepsilon_g)}{(\varepsilon_e + 2)(2\varepsilon_e + \varepsilon_g)} \frac{r_o^3}{r_e^3} - 2 \frac{(\varepsilon_e - 1)(\varepsilon_e + 2\varepsilon_g)(\varepsilon_g - \varepsilon_a)}{(\varepsilon_e + 2)(2\varepsilon_e + \varepsilon_g)(2\varepsilon_g + \varepsilon_a)} \frac{r_i^3}{r_e^3} \right]^{-1}.$$

The dipole moment induced in the sphere due to the applied external field $e_0$ is $4\pi\varepsilon_0 J_1$. In addition, the polarization of the system, $\alpha$, is the ratio of the induced dipole moment to the external applied field $e_0$. Hence the polarization may be written as $$\alpha = (4\pi\varepsilon_0) r_e^3 \left[ \frac{(\varepsilon_e - 1)}{(\varepsilon_e + 2)} K - \frac{(2\varepsilon_e + 1)L}{(\varepsilon_e + 2)(2\varepsilon_e + \varepsilon_g)} \frac{r_o^3}{r_e^3} \right] S. \quad (21)$$

Figure 22:
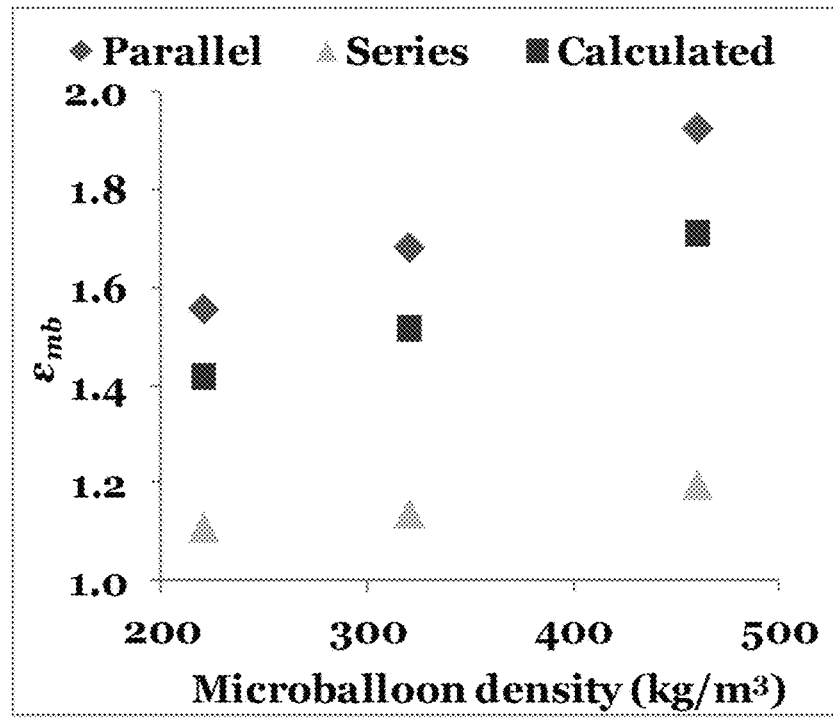
FIG. 22 depicts a dielectric constant calculated for a glass microballoon, along with values obtained from a parallel and a series model.

The effective dielectric constant of GMB may be found by equating the polarization of the system consisting of a hollow glass shell containing the air void to the polarization of an equivalent solid sphere. The dielectric constant of GMBs may be written as $$\varepsilon_{mb} = \left[ \frac{1 - 2\eta^3 \frac{(\varepsilon_g - 1)^2}{(\varepsilon_g + 2)(2\varepsilon_g + 1)} + 2(1 - \eta^3) \frac{(\varepsilon_g - 1)}{(\varepsilon_g + 2)}}{1 - 2\eta^3 \frac{(\varepsilon_g - 1)^2}{(\varepsilon_g + 2)(2\varepsilon_g + 1)} - (1 - \eta^3) \frac{(\varepsilon_g - 1)}{(\varepsilon_g + 2)}} \right] \quad (22)$$

where $\varepsilon_g$ and $\varepsilon_a$ are taken as 5.6 and 1, respectively. The calculated effective dielectric constants of the three types of GMBs used in the experiments are plotted with respect to their density in FIG. 22. The figure also contains upper and lower bounds obtained by the parallel and the series rule of mixtures, respectively. As shown in FIG. 22, the values calculated from the theoretical model were between the two bounds.

Although the syntactic foams are assumed to be filled with GMBs that are identical in all respects, a distribution may exist in their size and radius ratio. Experimental data are available on the size and radius ratio distribution of GMBs used in the present work, and may be used in the models to account for size and radius ratio variability range. The radius ratio values calculated from the experimentally measured density values of GMBs are 0.958, 0.948 and 0.928 for the 220, 320 and 460 type microballoons, respectively.

The effective dielectric constant for GMBs may be used in the Maxwell-Garnett and the J-S equations to predict the dielectric properties of particulate reinforced composites. The Maxwell-Garnett equation may be given by $$\varepsilon = \varepsilon_m \left[ 1 + \frac{3\Phi_{mb} \frac{\varepsilon_{mb} - \varepsilon_m}{\varepsilon_{mb} + 2\varepsilon_m}}{1 - \Phi_{mb} \frac{\varepsilon_{mb} - \varepsilon_m}{\varepsilon_{mb} + 2\varepsilon_m}} \right]. \quad (23)$$

The J-S equation is based on the Kerner's equation, and takes into account the particle-to-particle interaction between GMBs and may be given by $$\varepsilon = \frac{\Phi_m \varepsilon_m + \Phi_{mb} \varepsilon_{mb} \left( \frac{3\varepsilon_m}{\varepsilon_{mb} + 2\varepsilon_m} \right) \left( 1 + \frac{3\Phi_{mb}(\varepsilon_{mb} - \varepsilon_m)}{\varepsilon_{mb} + 2\varepsilon_m} \right)}{\Phi_m + \Phi_{mb} \left( \frac{3\varepsilon_m}{\varepsilon_{mb} + 2\varepsilon_m} \right) \left( 1 + \frac{3\Phi_{mb}(\varepsilon_{mb} - \varepsilon_m)}{\varepsilon_{mb} + 2\varepsilon_m} \right)}. \quad (24)$$

Figure 23:
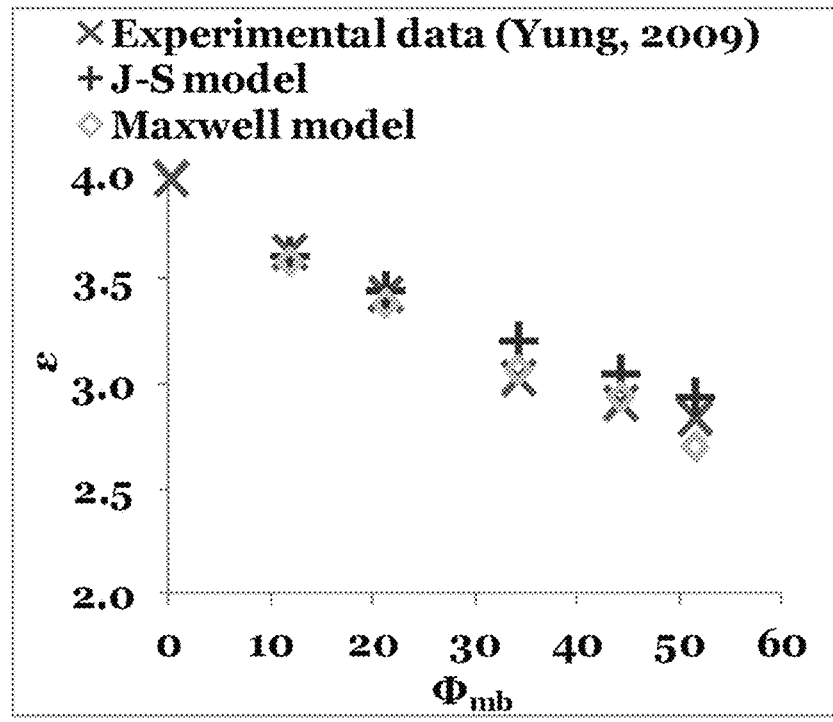
FIG. 23 depicts a comparison of theoretically calculated dielectric constant using the J-S and Maxwell-Garnett models with previously reported experimental values at 1 MHz for epoxy/GMB syntactic foams.

Previously reported data validated the results produced by these theoretical models. FIG. 23 shows that both the J-S and the Maxwell-Garnett model predictions closely match the experimental results, with only ±6% and ±5% deviation, respectively. This experimental data was obtained on syntactic foams containing GMB of 600 kg/m³ density tested at 1 MHz frequency and using $\varepsilon_g$=5.6. The value of $\varepsilon_g$ was not experimentally measured in this study and was assumed based on the general range for the soldalime borosilicate glass.

Figure 24A:
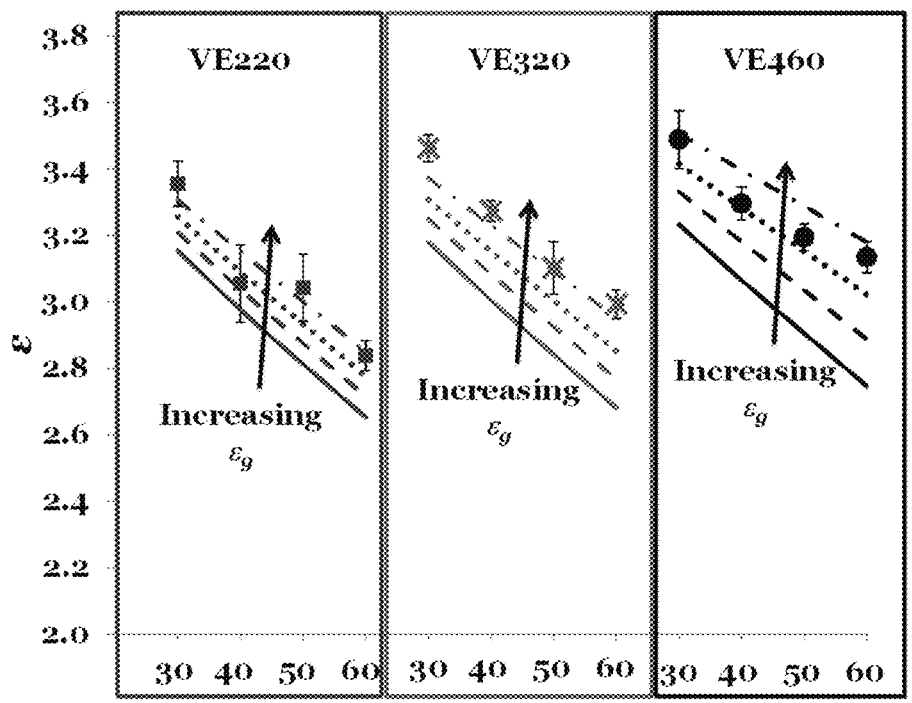
FIGS. 24A and 24B depict a comparison of a theoretically calculated dielectric constant using the J-S model where $\in_g$=5.6, 8, 10, and 12.15 and $\in_m$=3.87, and $\in_m$=3.87, 4, 4.1, and 4.2 and $\in_g$=5.6, respectively.
Figure 24B:
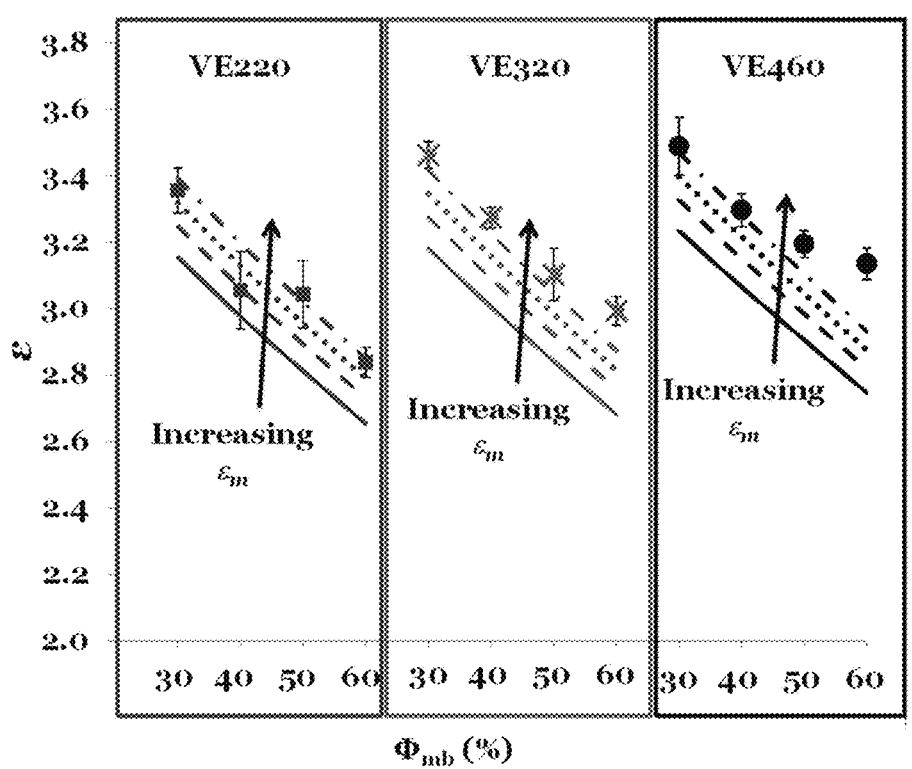

The dielectric constants predicted by the modified Maxwell-Garnett and J-S equations for the syntactic foams characterized are provided in Table 9. These predictions employ the experimentally measured dielectric constant of the neat resin as an input parameter, and $\varepsilon_g$ was taken as 5.6, which is consistent with previously reported values. Since the dielectric constant is dependent on the frequency, selection of $\varepsilon_m$ at appropriate frequency helps in obtaining predictions for syntactic foams at that frequency. The modified Maxwell-Garnett model predictions demonstrates a larger deviation from experimental values (±22%) than those obtained from the J-S model (±12%), as listed in Table 9. Although the modified J-S model predictions are closer to the experimental results, both models consistently underpredict the dielectric constant of the syntactic foams. To better understand this trend, the J-S model may be employed for conducting reverse calculations using the experimentally measured dielectric constant of syntactic foams for calculating the dielectric constant of glass $\varepsilon_g$, while taking $\varepsilon_m$ as 3.87. Experimentally measured values of $\eta$ from previously reported studies were used in the calculation. The calculated $\varepsilon_g$ value is obtained as 12.1±1.8. This value is high compared to the expected range for the sodalime borosilicate glass. Therefore a sensitivity analysis may be conducted on the model with respect to the two important input parameters: $\varepsilon_g$ and $\varepsilon_m$. The results are depicted in FIGS. 24A and 24B, where it is observed that the model is much more sensitive to variation in $\varepsilon_m$ than in $\varepsilon_g$. FIG. 24A utilizes values of $\varepsilon_g$ of 5.6, 8, 10, and 12.15 with $\varepsilon_m$ of 3.87. FIG.

24B utilizes values of $\in_m$ of 3.87, 4, 4.1, and 4.2 with $\in_g$ of 5.6. Changing the value of $\in_g$ from 3.87 to 4.2 shifted the theoretical curves to match with the experimental data. Small variations in a number of parameters such as cure conditions and resin to hardener ratio may affect the measured value of $\in_g$. This analysis demonstrates that the modified J-S model is capable of capturing the trend observed in the dielectric constant of syntactic foams and provides predictions with a reasonable degree of accuracy. The model also has a strong sensitivity to the dielectric constant of the resin, which is the continuous phase of the experimentally produced syntactic foams.

TABLE 9

| Specimen type | Average experimental ϵ | Maxwell-Garnett model ϵ | Error (%) | J-S model ϵ | Error (%) |
|---|---|---|---|---|---|
| VE220-30 | 3.36 | 3.01 | 10.4 | 3.15 | 6.0 |
| VE220-40 | 3.05 | 2.75 | 10.1 | 2.98 | 2.6 |
| VE220-50 | 3.04 | 2.50 | 17.9 | 2.81 | 7.6 |
| VE220-60 | 2.84 | 2.26 | 20.3 | 2.65 | 6.5 |
| VE320-30 | 3.46 | 3.05 | 12.0 | 3.18 | 8.2 |
| VE320-40 | 3.27 | 2.80 | 14.5 | 3.00 | 8.2 |
| VE320-50 | 3.10 | 2.56 | 17.5 | 2.84 | 8.4 |
| VE320-60 | 2.99 | 2.33 | 22.1 | 2.68 | 10.4 |
| VE460-30 | 3.49 | 3.12 | 10.4 | 3.23 | 7.3 |
| VE460-40 | 3.30 | 2.90 | 12.1 | 3.06 | 7.0 |
| VE460-50 | 3.19 | 2.68 | 16.1 | 2.91 | 9.0 |
| VE460-60 | 3.13 | 2.47 | 21.2 | 2.75 | 12.4 |

The modified J-S model was then employed for conducting a parametric study to understand the effect of GMB volume fraction and η on the dielectric constant of syntactic foams. The dielectric constant of the neat resin was taken as 3.87 at 100 kHz frequency in the parametric study.

Figure 25A:
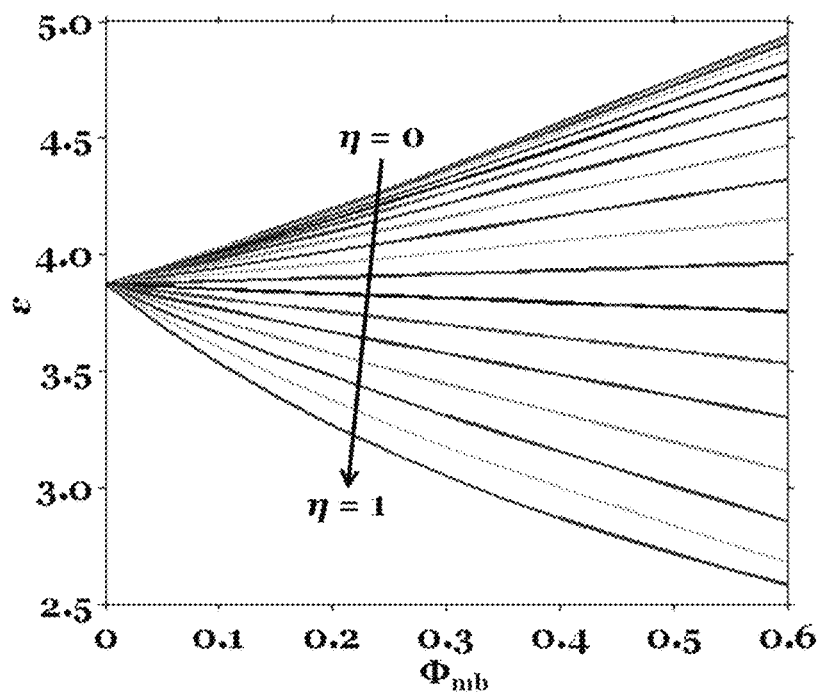
FIGS. 25A and 25B depict the dielectric constant of syntactic foams as a function of volume fraction and radius ratio, respectively.
Figure 25B:
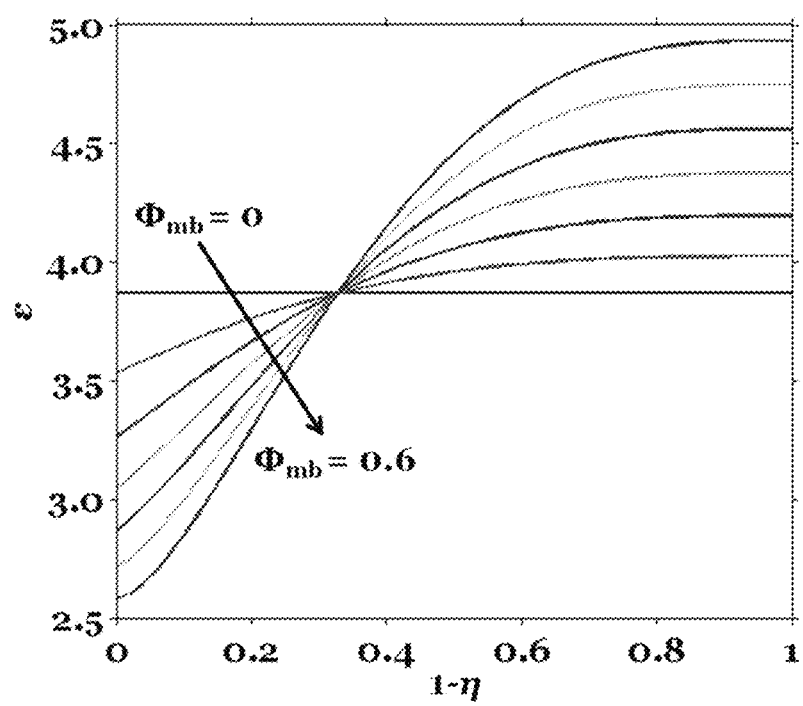

FIGS. 25A and 25B depict the variation of the dielectric constant of syntactic foams with respect to the GMB volume fraction and wall thickness, respectively. It may be observed that with the appropriate selection of GMB volume fraction and η, the dielectric constant of syntactic foams may be tailored over a wide range of 2.6-4.9. Thin walled GMBs, where η>0.7, may produce syntactic foams with a dielectric constant lower than that of the neat resin. This opposite trend is observed for GMBs where η<0.7.

Figure 26A:
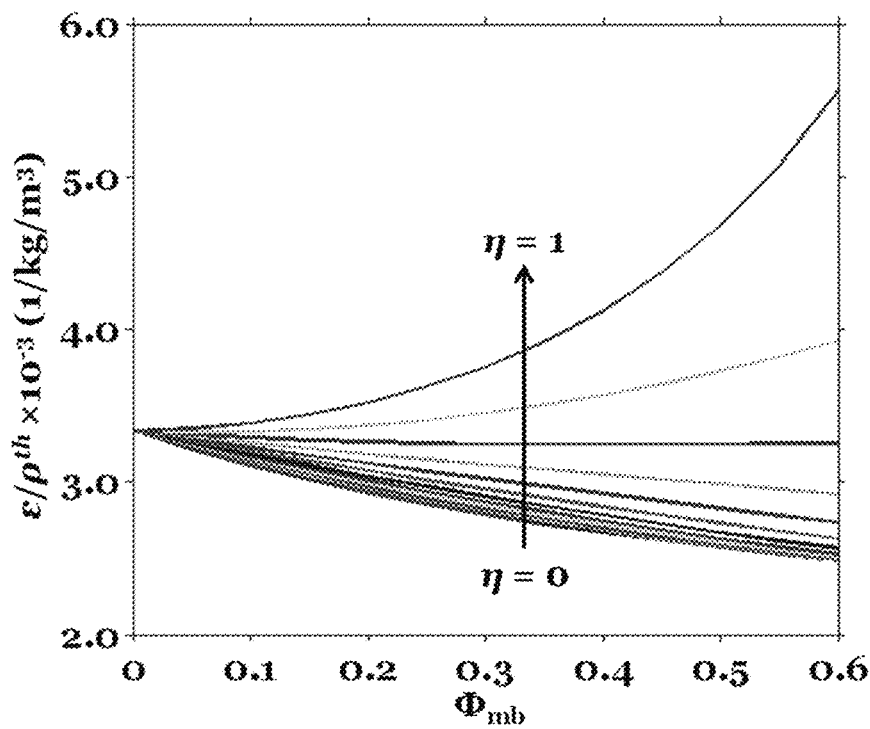
FIGS. 26A and 26B depict the variation of the specific dielectric constant (normalized with respect to the syntactic foam density) as a function of volume fraction and radius ratio, respectively.
Figure 26B:
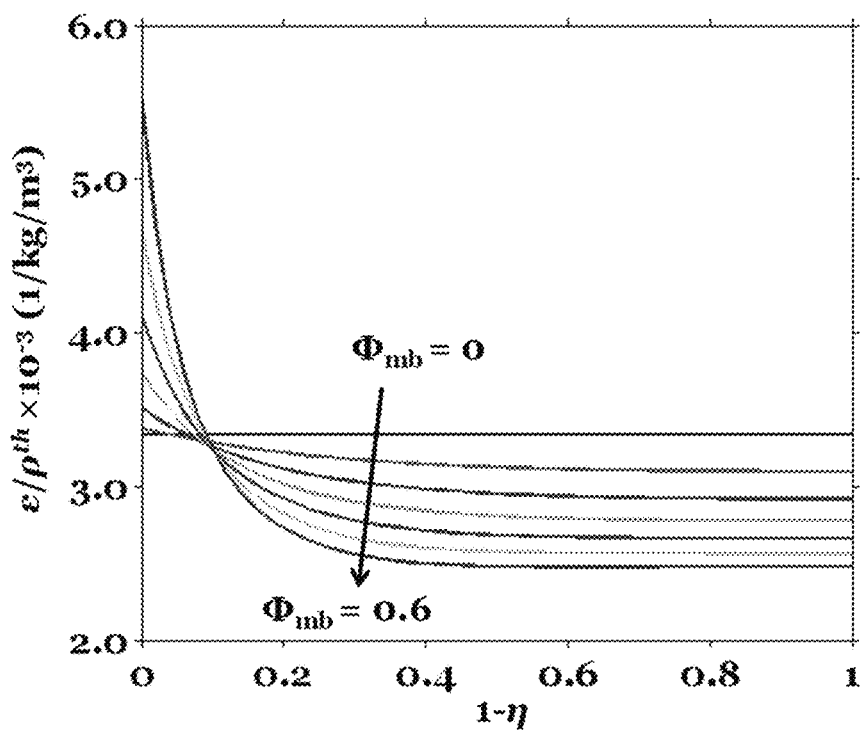

The specific dielectric constant normalized with respect to the syntactic foam density is presented as a function of volume fraction and radius ratio of the GMBs in FIGS. 26A and 26B, respectively. The density is observed to decrease more rapidly than the dielectric constant of the syntactic foams. Therefore, GMBs of lower wall thickness may provide a higher specific dielectric constant. FIG. 26B also shows that the effect of wall thickness variation on the specific dielectric constant may become negligible where η>0.7 for all GMB volume fractions. This observation may be very important in evaluating the weight savings obtained by using certain combinations of GMB volume fraction, $\Phi_{mb}$, and η. In syntactic foams, $\Phi_{mb}$ and η may be independently varied. Several combinations of $\Phi_{mb}$ and η may provide the same syntactic foam density. Therefore, the relationship between the dielectric constant, $\Phi_{mb}$ and η is further evaluated as depicted in FIGS. 27A and 27B.

Figure 27A:
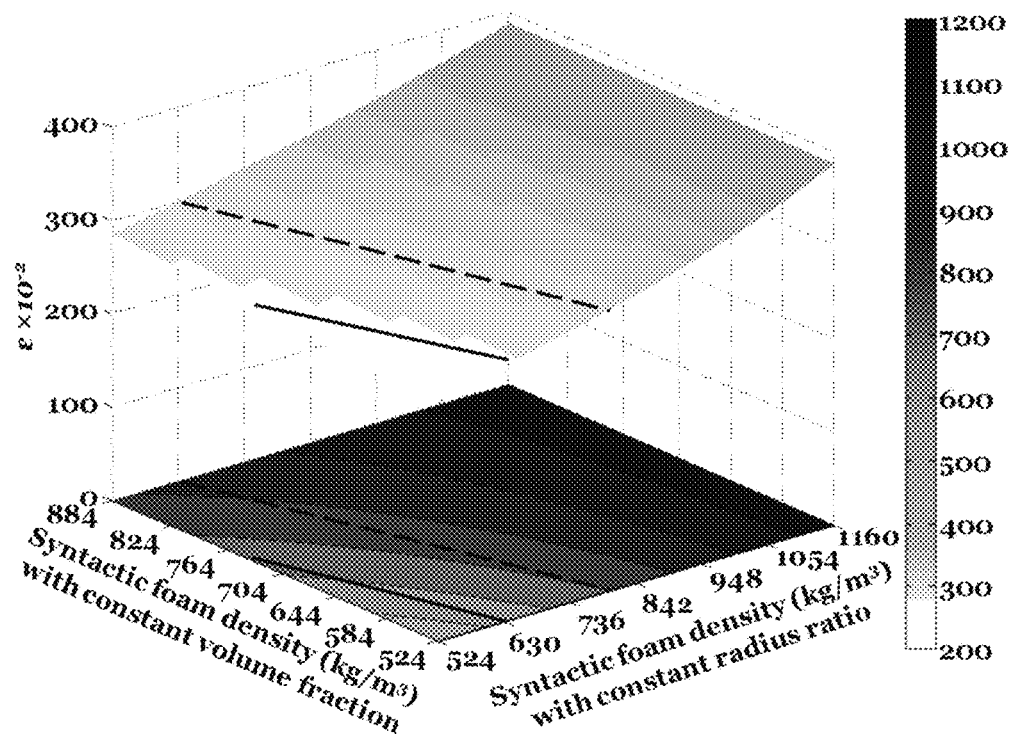
FIGS. 27A and 27B depict a contour plot of the variation of the dielectric constant as a function of syntactic foam density and the syntactic foam density as a function of volume fraction and radius ratio, respectively.
Figure 27B:
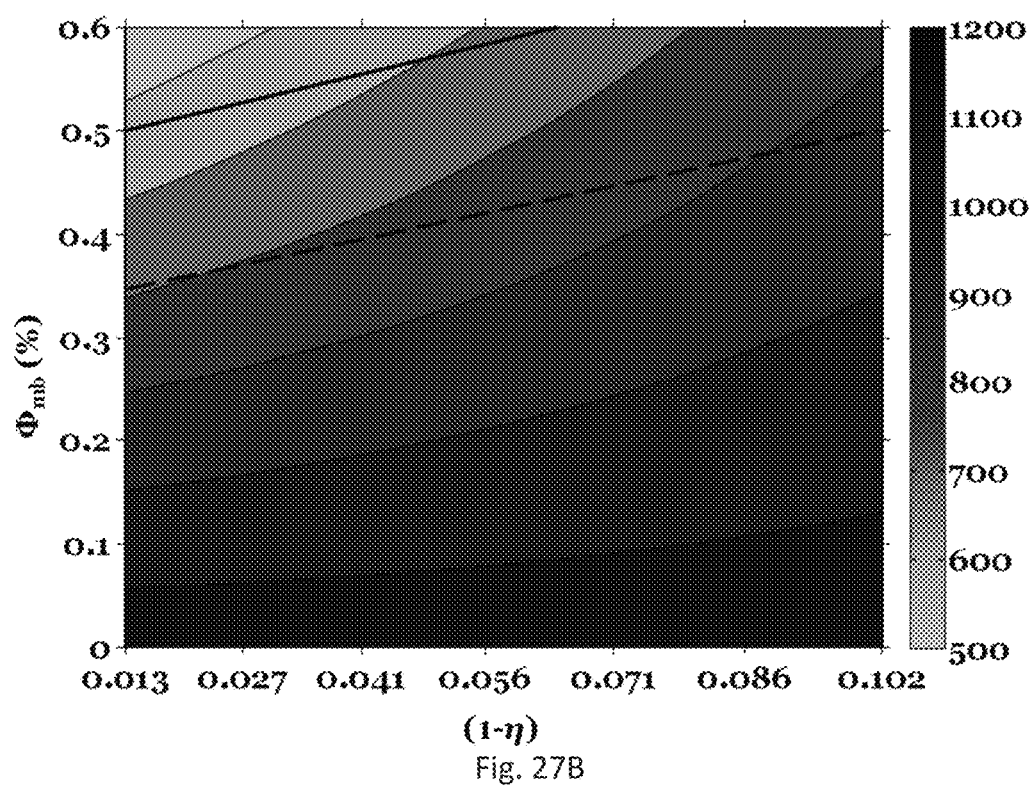

FIG. 27A depicts a 3D contour plot of dielectric constant variation along the vertical axis, whereas the floor of the graph contains a 2D contour plot of syntactic foam density variation with respect to GMB volume fraction and η marked on two different axes. The 2D contour plot is reproduced in FIG. 27B for the sake of clarity, where the axes are marked in terms of $\Phi_{mb}$ and η to illustrate the contribution of these parameters to syntactic foam density. The scale bar in FIG. 27A represents both dielectric constant and density of syntactic foams in their appropriate units.

Two representative values of the dielectric constant, namely $\in$=2.75 and 3, are denoted by a solid and a dashed line, respectively, in FIG. 27A. All the syntactic foam compositions along a given line have the same dielectric constant. These two lines are also projected on the density contour plot. It is noted that syntactic foams having densities in the range of 630-740 kg/m³ may be selected to have the same dielectric constant of 2.75. The syntactic foams having this range of densities have a GMB volume fraction in the range of 0.5-0.6 and η in the range 0.987-0.936. Since the mechanical properties of syntactic foams are also related to $\Phi_{mb}$ and η; the flexibility of selecting these parameters in a range, instead of a fixed value, provides the possibility of independently tailoring the dielectric constant and modulus within the ranges given by such charts. Similar observations can also be made for the second representative value of the dielectric constant of 3, where syntactic foam density may vary in the range of 790-930 kg/m³, which can be obtained by GMB volume fractions of 0.35-0.5 and η of 0.987-0.898. Many widely used GMBs in syntactic foams are within these ranges of $\Phi_{mb}$ and η. Appropriate combinations of $\Phi_{mb}$ and η may be selected to have the same syntactic foam density and dielectric constant, while having the desired mechanical properties.

The dielectric properties of vinyl ester/glass microballoon syntactic foams were found to decrease with an increase in the volume fraction of the microballoons and increase with an increase in the wall thickness of the microballoons. The dependence of the syntactic foam dielectric constant on microballoon volume fraction may be more pronounced in comparison to the wall thickness.

A linear relation was observed between the dielectric constant and the density of syntactic foams at all testing frequencies. An increase in the testing frequency produced a reduced dielectric constant of the syntactic foams. An equivalent sphere approach may be employed to obtain the dielectric constant of the hollow glass microballoons. This closed form expression was employed in coherence with the Maxwell-Garnett and the Jayasundere-Smith (J-S) models to obtain predictions of the dielectric constant of syntactic foams. The J-S model predictions were closer to the experimental values than the Maxwell-Garnett predictions. The J-S model was also validated with previously reported experimental data. The J-S model was then employed to perform a parametric study to further understand the relationship between a syntactic foam dielectric constant and microballoon volume fraction and wall thickness. The investigation shows that several compositions of syntactic foams may be developed to obtain the same dielectric constant. This approach allows the tailoring of the dielectric constant independent of other properties and the density of syntactic foams over a wide range.

Thermal Expansion

Experimental and theoretical studies were conducted to relate the coefficient of thermal expansion (CTE) of syntactic foams with the volume fraction and wall thickness of the GMBs and gain insight into the possibility of designing lightweight materials for thermal applications. GMBs of three different nominal densities (220 kg/m³, 320 kg/m³, and 460 kg/m³) were used in four different volume fractions (30%, 40%, 50%, and 60%) to fabricate twelve types of syntactic foams.

Figure 28:
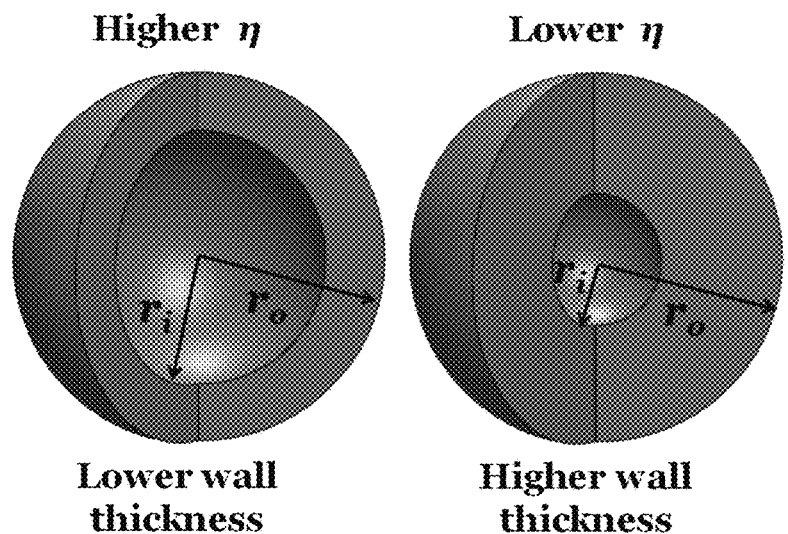
FIG. 28 depicts a schematic representation of hollow microballoons with the same outer diameter and different wall thicknesses.

The mean particle size and wall thickness of the syntactic foams are presented in Table 10. A graphical representation of the relationship of the inner radius and the outer radius of the microballoon is shown in FIG. 28. The calculated values of η for the selected particles are also provided in Table 10. The η values were in a narrow range for the selected particles. With an increasing volume fraction of lighter particles the composite modulus may decrease, whereas the composite modulus may increase with an increasing volume fraction of higher density particles. Therefore, in syntactic foams these particles are defined as thin and thick walled, respectively.

TABLE 10

| Specimen type | Mean particle size (μm) | Particle wall thickness (μm) | Particle radius ratio | Theoretical density (kg/m³) | Experimental density (kg/m³) | Matrix porosity (vol. %) |
|---|---|---|---|---|---|---|
| VE220-30 | 35 | 0.52 | 0.958 | 878 | 857.8 | 2.3 |
| VE220-40 | | | | 784 | 774.4 | 1.2 |
| VE220-50 | | | | 690 | 642.1 | 6.9 |
| VE220-60 | | | | 596 | 566.2 | 5.0 |
| VE320-30 | 40 | 0.88 | 0.948 | 908 | 872.7 | 3.9 |
| VE320-40 | | | | 824 | 752.3 | 8.7 |
| VE320-50 | | | | 740 | 667.3 | 9.8 |
| VE320-60 | | | | 656 | 617.7 | 5.8 |
| VE460-30 | 40 | 1.29 | 0.928 | 950 | 904.0 | 4.8 |
| VE460-40 | | | | 880 | 878.4 | 0.2 |
| VE460-50 | | | | 810 | 768.4 | 5.1 |
| VE460-60 | | | | 740 | 725.5 | 2.0 |

Figure 29A:
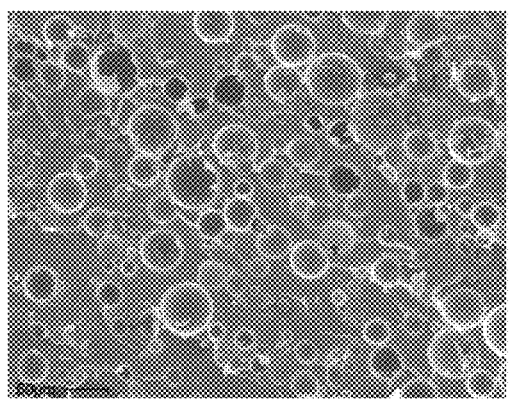
FIGS. 29A and 29B are scanning electron micrographs of a VE220-30 syntactic foam and a VE220-60 syntactic foam, respectively.
Figure 29B:
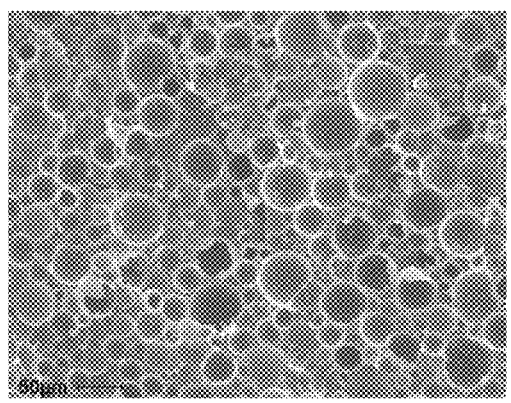

Table 10 provides the theoretical and the experimental densities of the syntactic foam specimens along with the matrix porosity content. The matrix porosity values may be considered an indicator of the quality of the fabricated composites. These values are not related to the CTE of syntactic foam because in the small size specimens used for CTE measurement, the specimens containing voids may generally be detected and avoided by careful surface inspection. In addition, the weight and dimensions of each CTE specimen were measured to calculate their density. The presence of a large matrix porosity produces a low density specimen, and may be easily detected and excluded from the experimental scheme. The representative microstructures of syntactic foams containing 30 vol. % and 60 vol. % GMB of the 220 type are shown in FIGS. 29A and 29B, respectively. A uniform distribution of GMBs may be observed in these figures. A similar microstructure was observed in foams containing the 320 and the 460 type particles.

Specimens of nominal dimensions of 11×5.5×3.5 mm (length×width×height) were prepared for CTE measurement. The specimens were heated in a convection oven for 3 hours at 70° C. to remove any adhered moisture.

Figure 30:
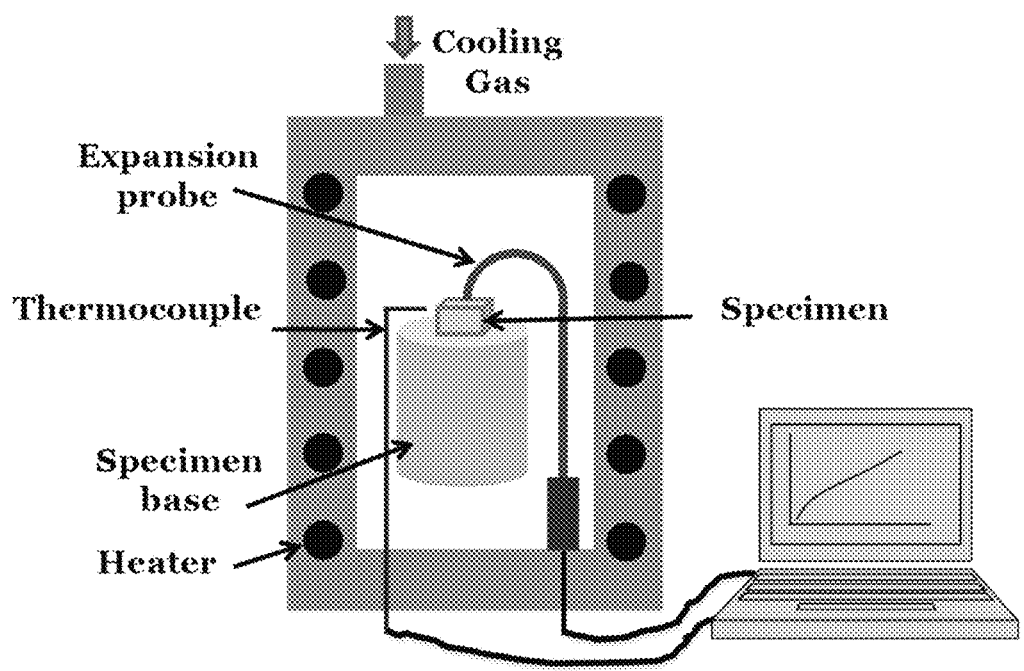
FIG. 30 is a schematic representation of an experimental setup of a thermomechanical analyzer for the measurement of the coefficient of thermal expansion.

The CTE characterization of the specimens was conducted using a Q400 Thermomechanical Analyzer. The schematic of the experimental setup is depicted in FIG. 30. An expansion type probe was used for measuring the temperature dependent dimensional changes. A preload of 0.02 N was applied for all tests. The measurements were conducted from room temperature to 75° C. Time, temperature, and change in specimen height were recorded during the test and used to estimate the CTE. In initial experiments 1° C./min, 3° C./min, and 5° C./min heating rates were employed. Based on the results, a 3° C./min heating rate was found to produce thermal equilibrium in the specimens this heating rate and the results were consistent.

Figure 31A:
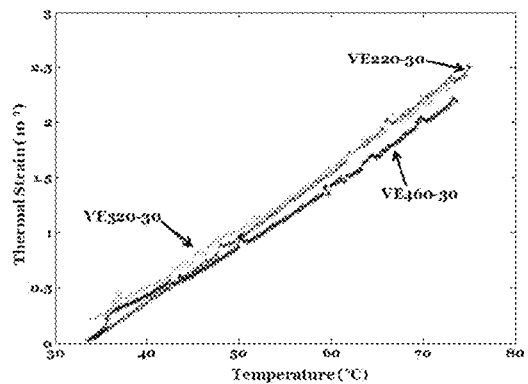
FIGS. 31A, 31B, 31C and 31D depict thermal strain as a function of temperature for syntactic foams containing a particle volume fraction of 30%, a particle volume fraction of 60%, a radius ratio of 0.958, and a radius ratio of 0.928, respectively.
Figure 31B:
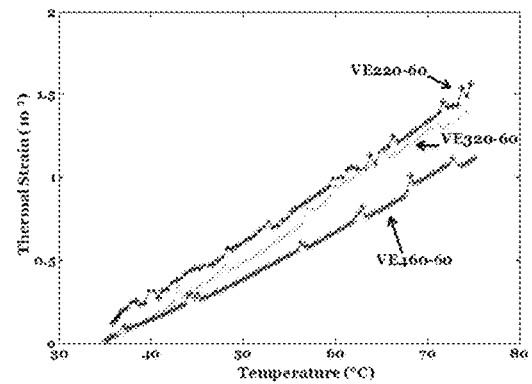
Figure 31C:
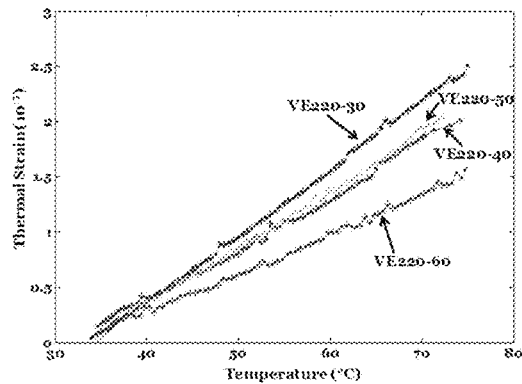
Figure 31D:
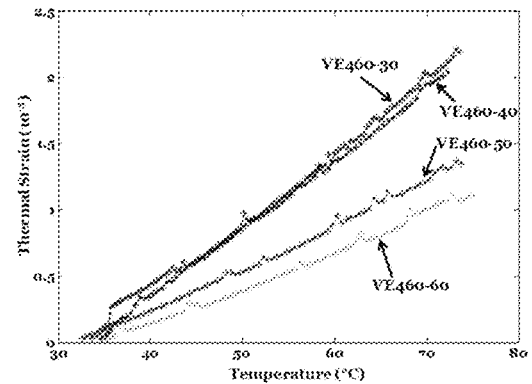

FIGS. 31A and 31B depict representative plots of thermal strains with respect to temperature for syntactic foams having 30 vol. % and 60 vol. % GMB of different η, respectively. Similar trends were observed for other volume fractions as well. It was observed that the dimensional change was the steepest for thin walled particles, indicating that the dimensional stability of the composite increases with an increase in the particle wall thickness. FIGS. 31C and 31D compare a representative set of results for composites containing GMB densities of 220 kg/m³ and 460 kg/m³ in different volume fractions, respectively. The trends observed for other particles are similar. FIGS. 31C and 31D demonstrate that increasing the GMB volume fraction in syntactic foams produces an increase in dimensional stability. The slope of such graphs may be used to calculate the CTE of syntactic foams (α) as given by $$\alpha = \frac{1}{l} \times \frac{dl}{dT} \quad (25)$$

where l is the initial specimen length and dl/dT is the slope of the dimension change-temperature plot.

Figure 32:
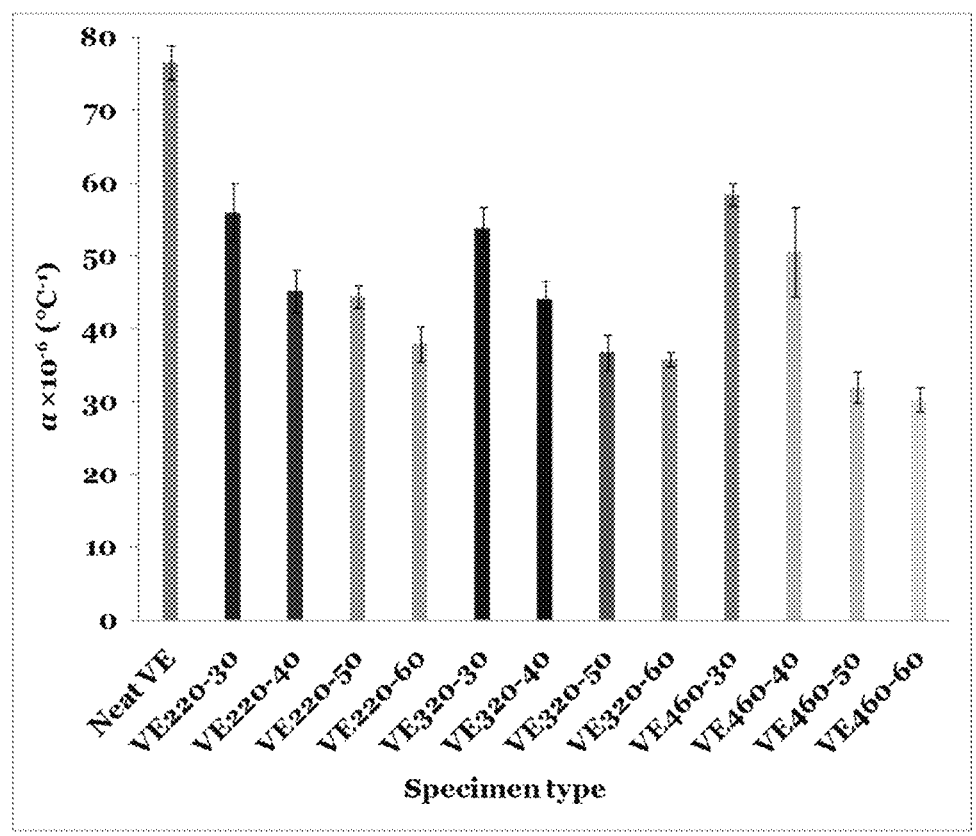
FIG. 32 depicts experimentally measured values of the CTE for a neat resin and various syntactic foams, with error bars representing standard deviations in the experimental measurements.

The experimental measured values of the CTE are plotted in FIG. 32. A trend was observed that an increase in the GMB volume fraction provides improved dimensional stability to the composite. For comparison, the CTE of the neat resin was also plotted in FIG. 32. It was observed that the value of the CTE of the syntactic foams is up to 60.4% less than the CTE of the neat resin. The lowest CTE value was observed for the VE460-60 syntactic foam, which contains GMB of the highest wall thickness in the maximum volume fraction investigated.

The experimental results were analyzed to understand the effect of several parameters on the CTE of the syntactic foams. FIG. 32 shows that increasing the volume fraction and wall thickness of GMBs decreases the CTE of the syntactic foams. It was observed that increasing the volume fraction of the 220 type particles from 30 vol. % to 60 vol. % decreases the CTE of composites by 27-50% compared to the neat resin. Similarly, the 320 and the 460 type GMBs produce a 30-53% and 23-60% decrease in the CTE of the syntactic foams compared to neat vinyl ester resin, respectively. In comparison to the volume fraction, microballoon wall thickness exhibits a milder effect on the CTE of the syntactic foams within the investigated range. At the same GMB volume fractions, the syntactic foam CTE values demonstrate a difference within 10% for most particle types. Only VE220-50 exhibited a deviation from this trend due to the higher CTE value than would be expected from the experimental trends observed for the entire set of compositions. The density of the syntactic foams also follows a qualitatively similar trend with respect to the microballoon volume fraction and wall thickness, as seen in Table 10. Among the present batch of composite specimens, VE460-60 has the highest glass content and the lowest measured CTE value.

Developing a correlation between composite density and the CTE through theoretical models may be useful because common applications of syntactic foams are based on their low density and the ability to tailor the mechanical and thermal properties. Two different models applicable to solid particle reinforced composites were analyzed for the possibility of modifying them for hollow particle reinforced composites and the predictions are validated with experimental results.

The rule of mixtures (ROM) is widely employed to obtain an upper bound of various properties of composite materials. The ROM for the CTE estimation may be written as $$\alpha = \alpha_m \phi_m + \alpha_b \phi_b \quad (26)$$

where $\alpha_m$ and $\alpha_b$ are the CTE of the matrix resin and the GMB, respectively, and $\phi_m$ and $\phi_b$ are the volume fraction of the matrix and the GMB, respectively. ROM is the basis for several theoretical models. Other theoretical models for predicting the CTE values of solid particle reinforced composites are also available. These models are mainly applicable to composites containing solid fillers and do not include particle wall thickness, which is an additional parameter available for variation in syntactic foams. Turner's and Kerner's models have been modified herein to include the effect of wall thickness of hollow particles on the CTE of the composite material. Turner's model may be given by $$\alpha = \frac{\alpha_m \phi_m K_m + \alpha_b \phi_b K_b}{\phi_m K_m + \phi_b K_b} \quad (27)$$

where $K_m$ and $K_b$ are the bulk moduli of the matrix and the microballoon, respectively. The bulk modulus may be estimated from the Young's modulus of the constituents of the composite as $$K = E/(3(1-2v)) \quad (28)$$

where E is the Young's modulus and v the Poisson's ratio of the respective constituents.

The effective modulus of the GMB differs from the modulus of the glass and depends on the wall thickness. To determine the effective GMB modulus, an equivalent sphere with the same properties as the hollow GMB was assumed. The radial displacement at the outer surface of the two systems were compared and the effective modulus (E*) as a function of the microballoon radius ratio may be given by $$E^* = \frac{E_g(1-2v)(1-\eta^3)}{(1-2v) + \left(\frac{1+v}{2}\right)\eta^3} \quad (29)$$

where $E_g$ is the modulus of the microballoon glass material and was assumed to be 60 GPa. The modified Turner's model for the CTE of the hollow particle filled composites may be given by substituting Eq. (28) and (29) in Eq. (27) producing $$\alpha = \frac{\alpha_m \phi_m E_m\left[(1-2v_g) + \left(\frac{1+v_g}{2}\right)\eta^3\right] + }{\phi_m E_m\left[(1-2v_g) + \left(\frac{1+v_g}{2}\right)\eta^3\right] + \phi_b E_g(1-\eta^3)(1-2v_m)} \quad (30)$$

where $v_g$ is the Poisson's ratio of the microballoon material and was assumed to be 0.21, $E_m$ is the modulus of the matrix and was assumed to be 2.82 GPa, and $v_m$ is the Poisson's ratio of the matrix material and was assumed to be 0.35.

The Kerner's model may be given by $$\alpha = \alpha_m \phi_m + \alpha_b \phi_b + \phi_b \phi_m (\alpha_b - \alpha_m) \times \left(\frac{K_b - K_m}{\phi_m K_m + \phi_b K_b + \frac{3K_b K_m}{4G_m}}\right) \quad (31)$$

where $G_m$ is the shear modulus of the matrix material. The Kerner's model (Eq. 31) may be modified to obtain a new version (Eq. 32) for hollow particle filled composites given by $$\alpha = \alpha_m \phi_m + \alpha_b \phi_b + \phi_b \phi_m (\alpha_b - \alpha_m) \times \quad (32)$$

$$\left[\frac{E_g(1-\eta^3)(1-2v_m) - E_m\left[(1-2v_g) + \frac{(1+v_g)}{2}\eta^3\right]}{\phi_m E_m\left[(1-2v_g) + \frac{(1+v_g)}{2}\eta^3\right] + \phi_b E_g(1-\eta^3)(1-2v_m) + \frac{1}{2}E_g(1-\eta^3)(1+v_m)}\right]$$

Figure 33A:
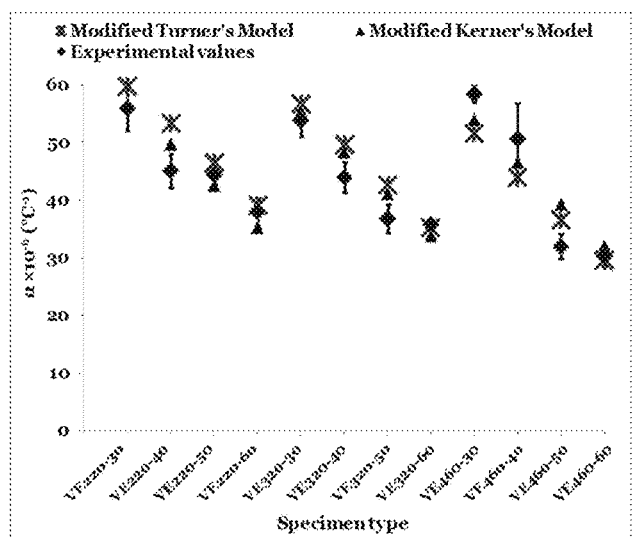
FIGS. 33A, 33B, and 33C depict a comparison of theoretically calculated CTE values using Turner's and Kerner's models and experimentally measured values, a comparison of theoretically calculated CTE values using Turner's and Kerner's models and a first set of previously reported experimental data, and a comparison of theoretically calculated CTE values using Turner's and Kerner's models and a second set of previously reported experimental data, respectively.

Equations (30) and (32) were employed to determine the theoretical estimates of CTEs of various syntactic foams and the results are presented in FIG. 33A. The CTE of the neat resin was determined to be 76.5 µm/m° C. based on the experimental results presented in FIG. 32, and the CTE of the microballoon glass was assumed to be 4 µm/m° C. A comparison demonstrates that the theoretical values presented in FIG. 33A closely match with the experimental values as shown in FIG. 32, and the observed difference was in the range of ±15% for the modified Turner's model and ±18% for the modified Kerner's model. There are several factors such as matrix porosity and use of literature values for Poisson's ratio that may produce some difference in the theoretical and experimental results. In addition, polydispersion in particle size and volume fraction may also produce some variation in the measured properties. Accounting for these parameters may provide more accurate theoretical estimates.

Figure 33B:
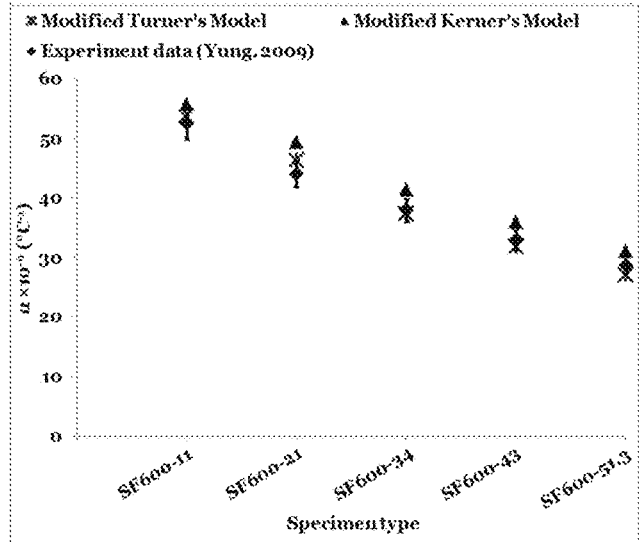
Figure 33C:
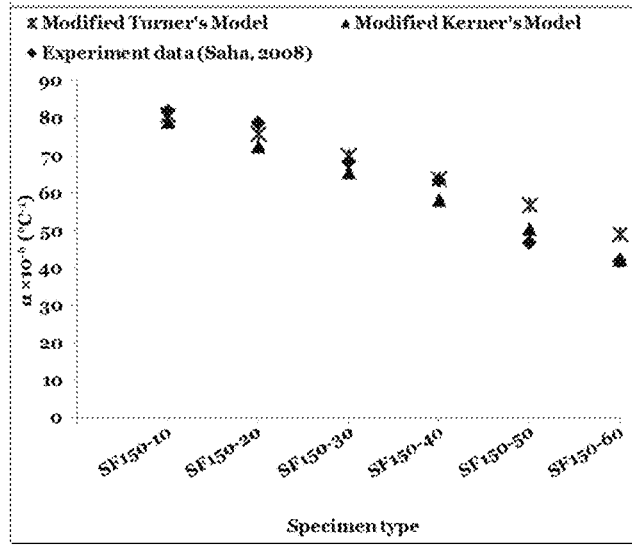

Since both the modified Turner's and Kerner's models demonstrated a close match with the experimental results, they were each also validated with previously reported experimental values of CTE. Syntactic foams with microballoon densities of 600 kg/m³ and 150 kg/m³ were used to analyze the CTE, and the comparison of theoretical and experimental values for these studies is shown in FIGS. 33B and 33C, respectively. Close matching between the theoretical and the experimental results provides further validation of the models utilized to predict the CTE of syntactic foams. Experimental data on syntactic foams containing $\phi_b$<0.3 is not widely available as such high density syntactic foams may be unsuitable for applications in which weight savings through the use of lightweight materials is desired.

Figure 34A:
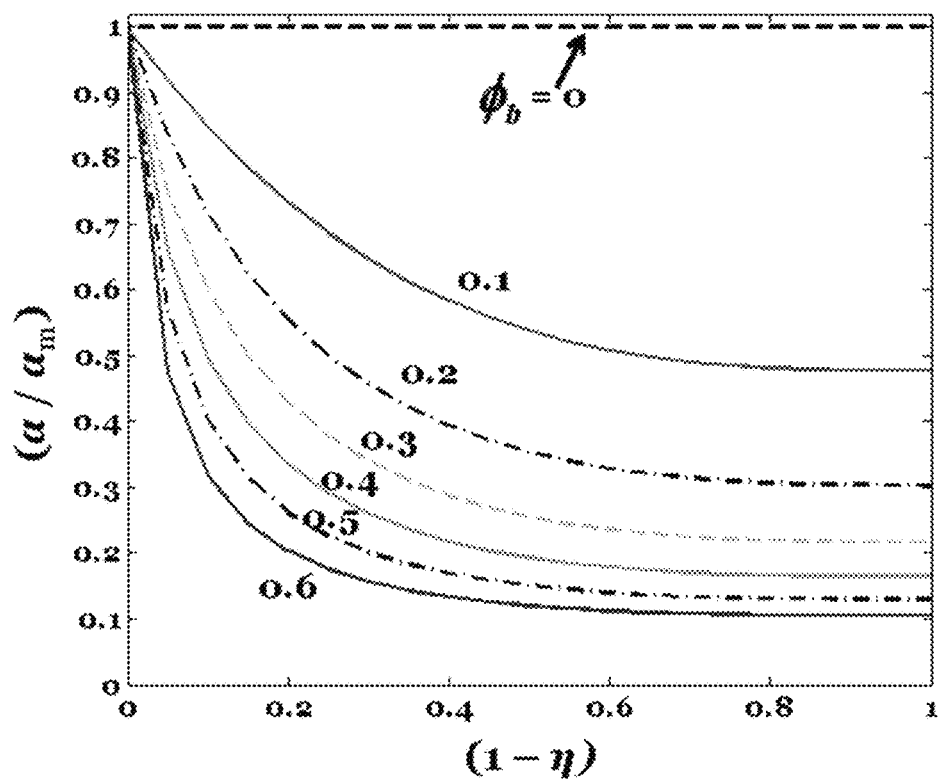
FIGS. 34A and 34B depict the CTE of syntactic foams normalized with the CTE of the matrix resin as a function of wall thickness and particle volume fraction, respectively.
Figure 34B:
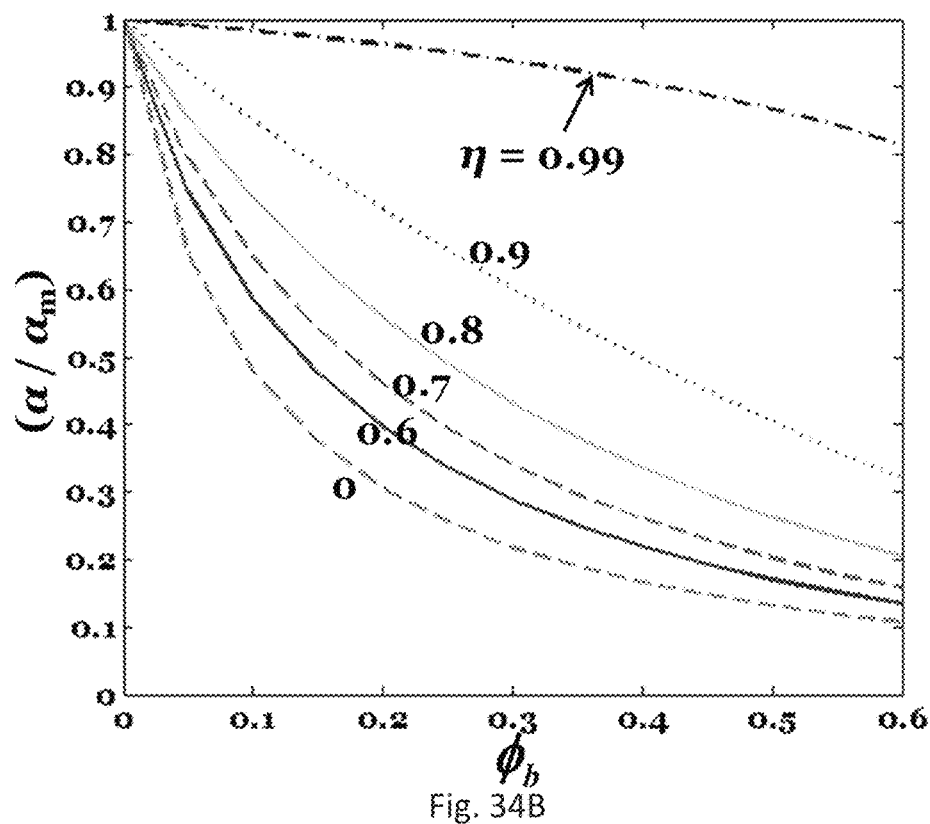

The modified Turner's model was selected to perform a parametric study on the variation of CTE with respect to radius ratio and volume fraction of the GMBs. FIG. 34A plots the normalized CTE as a function of η for various values of $\phi_b$. It was observed that in the case of (1−η)<0.4 (i.e. thin walled particles), which may be important for weight saving materials, there is a steep change in CTE. Many previously reported syntactic foams have employed particles with a (1−η) value in the range of 0 to 0.1, where CTE decreases sharply. However, the rate of CTE change reduces substantially in the region (1−η)>0.4 (i.e. thick walled particles). For (1−η)>0.5 the rate of CTE change was almost negligible. This trend indicates that for a fixed volume fraction of GMB, the use of microballoons of $(1-\eta)>0.5$ produces an increase in the composite density without further improvement of the dimensional stability of the composite. A comparison of trends in FIG. 34B demonstrates that increasing the volume fraction of GMB with a constant wall thickness may produce an over 80% reduction in the CTE of the composite compared to the matrix material. Within the range $0.8<\eta<1$, the CTE behavior of syntactic foams changes rapidly, but the rate of change decreases at $\eta<0.8$. The line for $\eta=0$ in FIG. 34B presents the case of solid particle reinforced composite and is the lower bound of the CTE.

Figure 35A:
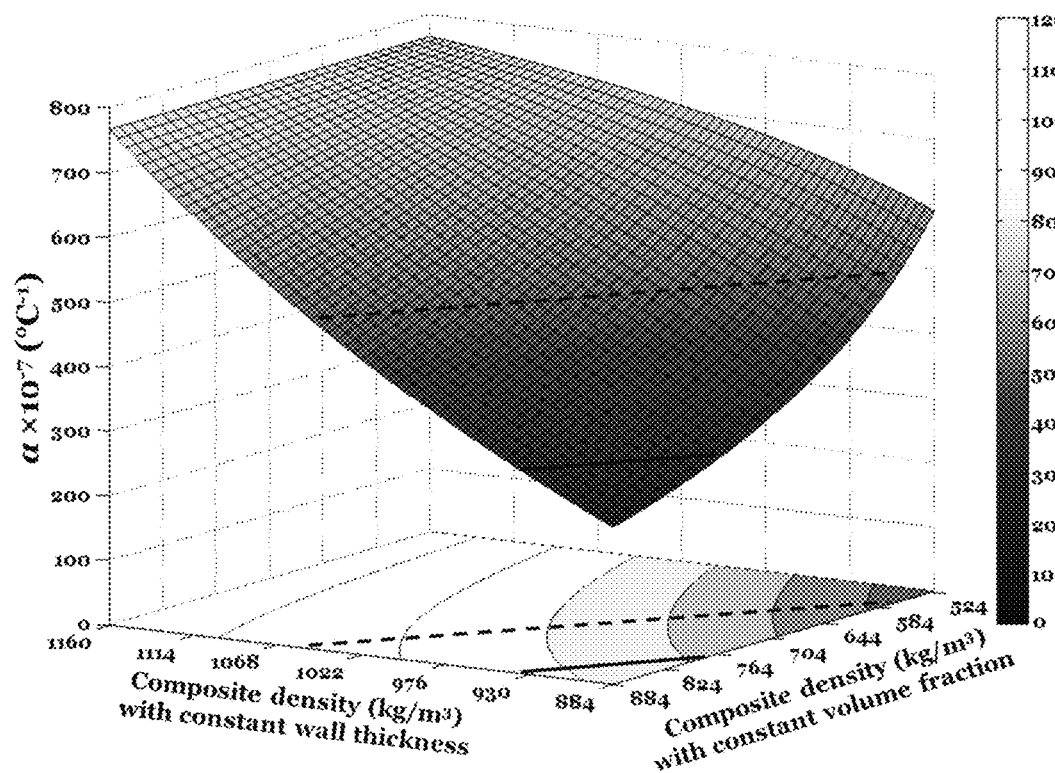
FIGS. 35A and 35B depict a contour plot of the variation of CTE as a function of syntactic foam density, and the syntactic foam density as a function of volume fraction and wall thickness, respectively.
Figure 35B:
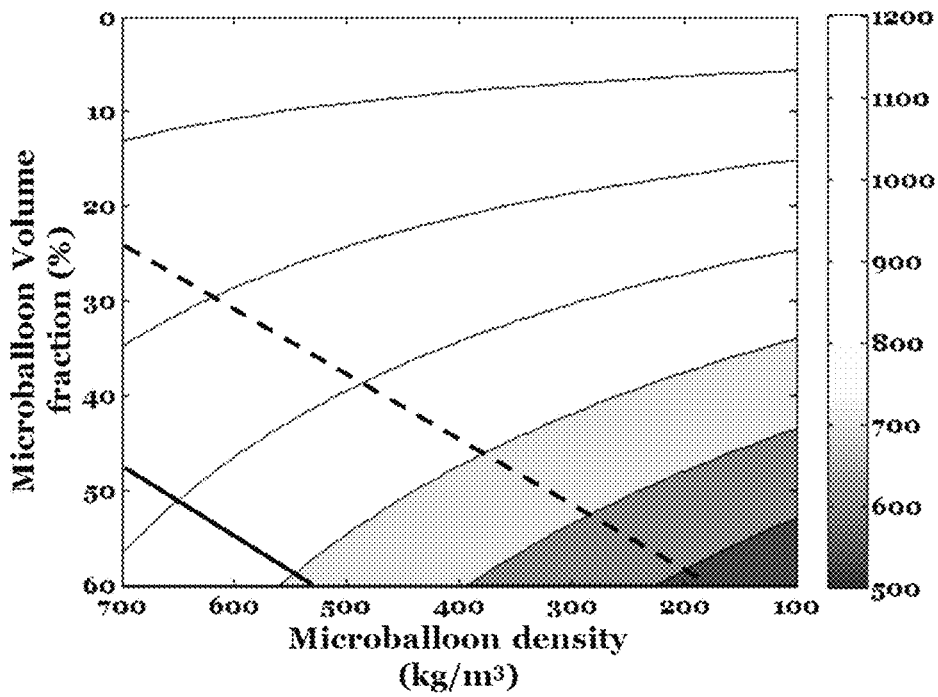

The weight saving potential through the selection of material parameters was explored for GMB/vinyl ester syntactic foams. The 3D contour plot in FIG. 35A shows the CTE variation with respect to the composite density. The composite's density variation as a function of GMB volume fraction and wall thickness (or density) is plotted on the bottom of FIG. 35A as a 2D contour plot. The scale bar in FIG. 35A demonstrates both the CTE variation and the composite density variation in their appropriate units. The relationship between the composite density and the microballoon volume fraction and density is further clarified in FIG. 35B as a 2D contour plot. The syntactic foam density ranges depicted in FIGS. 35A and 35B are the same. Reduction in the composite's CTE was evident with an increase in the GMB volume fraction and wall thickness. A solid and a dotted line are shown in FIGS. 35A and 35B, for two representative constant values of $\alpha=300\times10^{-7\circ}$ C.$^{-1}$ and $\alpha=500\times10^{-7\circ}$ C.$^{-1}$, respectively. It may be observed in FIG. 35A that a variety of GMB/vinyl ester syntactic foam compositions having densities over a large range of 572-1050 kg/m$^3$ may be employed to obtain a CTE of $500\times10^{-7\circ}$ C.$^{-1}$. Correspondingly, FIG. 35B demonstrates that a combination of GMB volume fractions in the range of 24-60% with the GMB densities in the range of 180-700 kg/m$^3$ may provide the same CTE value of $500\times10^{-7\circ}$ C.$^{-1}$. Similar observations may be made for $\alpha=300\times10^{-7\circ}$ C.$^{-1}$, where numerous syntactic foam compositions having densities in the range of 784-935 kg/m$^3$ may be used to obtain the CTE value. Such flexibility may allow the tailoring of the composite properties for thermal applications. The parametric study results for the CTE observed in FIGS. 35A and 35B may be combined with the existing understanding of mechanical properties of syntactic foams. Such combination of mechanical and thermal properties may allow the selection of the best possible parameters in designing syntactic foams for a given application.

The CTE of polymer matrix syntactic foams was studied with respect to the hollow particle wall thickness and volume fraction. The CTE of the syntactic foams was found to decrease with an increasing microballoon wall thickness and volume fraction. The CTE of the composites was found to be up to 60.4% lower than the CTE of the neat resin for the composites characterized herein. Within the range of parameters studied herein, the microballoon volume fraction was found to be effective in modulating the CTE of syntactic foams. Turner's and Kerner's models were modified to include the effect of particle wall thickness and develop predictive models for syntactic foams. The modified Turner's model provided predictions within ±15% of the experimental results. The parametric study demonstrates that a combination of the microballoon wall thickness and the volume fraction may be effectively employed to produce composites with a desired CTE. In addition, the wide range of choices available for the microballoon volume fraction and wall thickness for obtaining syntactic foams with the same CTE value may facilitate the tailoring of the density and mechanical properties at the same time.

Figure 36A:
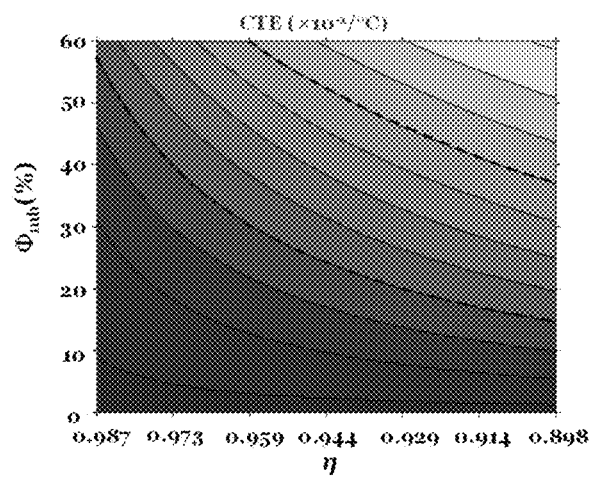
FIGS. 36A, 36B, and 36C depict the variation of the CTE, density, and modulus, respectively, of syntactic foams as a function of particle density and volume fraction.
Figure 36B:
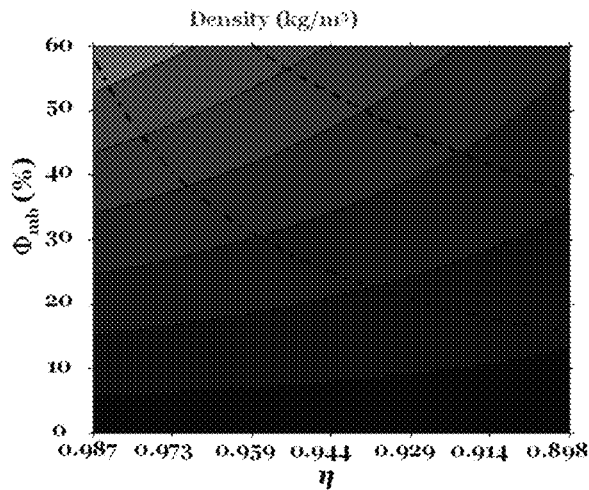
Figure 36C:
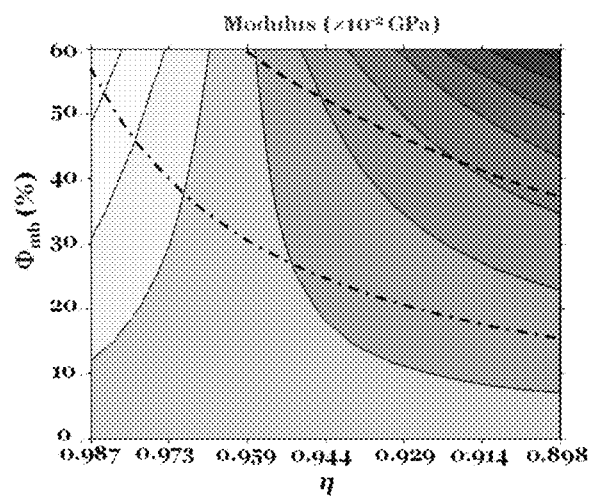

As shown in FIG. 36A, various compositions of syntactic foams may be produced that have a CTE of $40\times10^{-6}$/° C., indicated by the dashed line. Similarly, the dashed-dotted line in FIG. 36A marks the compositions that have a CTE of $60\times10^{-6}$/° C. A theoretical model was used to obtain the syntactic foam modulus in the same range of volume fraction and wall thickness, as shown in FIG. 36B. Further, a density map of the syntactic foams having the same range of volume fraction and wall thickness was developed using rule of mixtures and is plotted in FIG. 36C. Since the variation of the CTE, modulus and the density 2D-maps are based on the same rage of $\eta$ and $\Phi_{mb}$, these 2D plots may be superimposed on each other to find the range of modulus and densities for the same values of CTE and the corresponding $\eta$ and $\Phi_{mb}$ may be determined. Tables 11 and 12 provide the compositions, densities, and modulus of syntactic foams corresponding to the CTE values of $40\times10^{-6}$/° C. and $60\times10^{-6}$/° C., respectively.

Table 11 shows that the syntactic foams having densities in the range 644-990 kg/m$^3$ may provide a CTE of $40\times10^{-6}$/° C. In this composition range, the modulus of syntactic foams may vary in the range 2.8-4.1 GPa by changing the $\Phi_{mb}$ in the range 0.37-0.6 and correspondingly selecting appropriate $\eta$ that ranges between 0.898 and 0.959. The second representative example for syntactic foams having a CTE of $60\times10^{-6}$/° C. is presented in Table 12, where the density may vary in the range 556-1091 kg/m$^3$ and the modulus may vary in the range 1.226-3.231 GPa by tailoring the combination of $\eta$ and $\Phi_{mb}$. Depending on the requirements of an application, either syntactic foams of lowest density or desired modulus may be selected from this available composition range. This possibility of obtaining multifunctionality in the syntactic foam properties provides greater flexibility than solid reinforcement filled composites.

Figure 37:
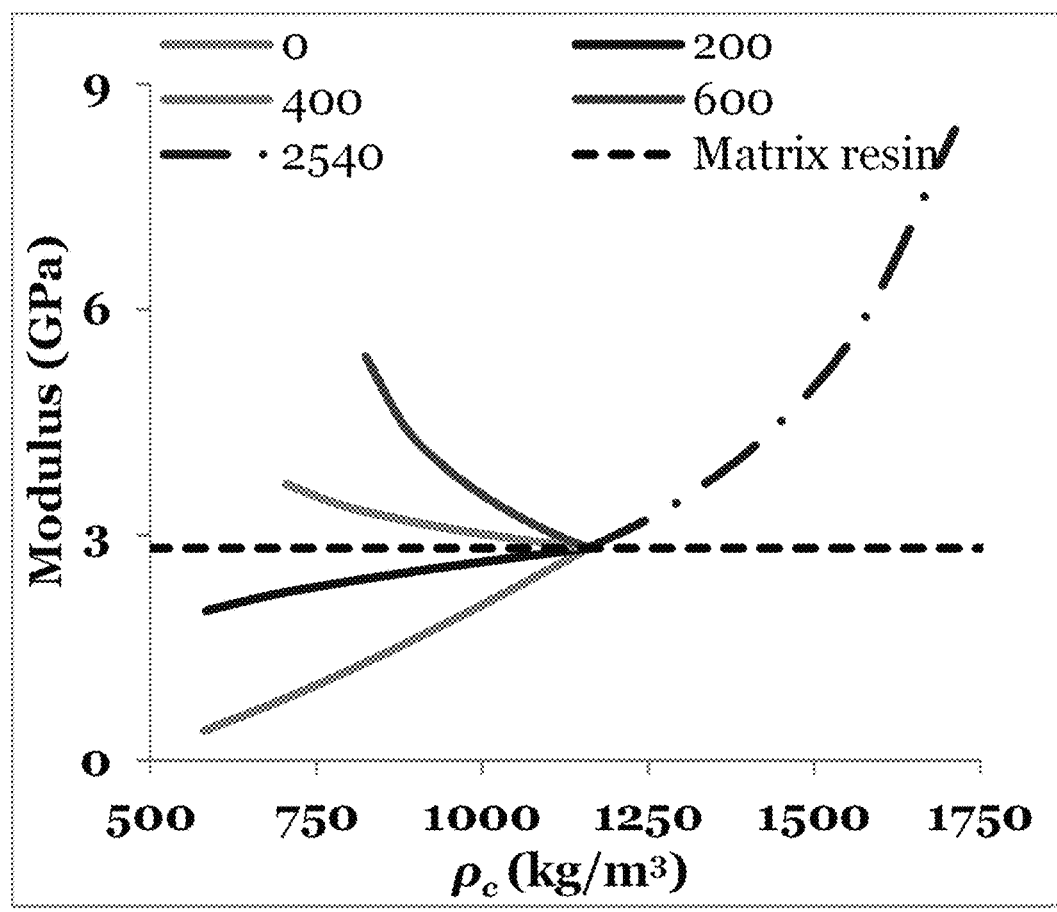
FIG. 37 depicts the variation of the modulus as a function of density for syntactic foams for various reinforcing fillers, with 0 representing air pores; 200, 400 and 600 representing true particle densities of hollow glass microballoons; and 2540 representing solid glass particles.

The advantage of utilizing syntactic foams in comparison to the neat resin, closed-cell air filled foams and solid particulate reinforced composites may be observed in FIG. 37. This figure includes results obtained from the same theoretical model and input parameters that are used for FIG. 36C. The addition of solid particles may produce higher modulus values in comparison to the matrix resin, at the cost of increasing the composite density. The addition of air pores, which creates closed-cell foams containing gas porosity, reduces the density while also decreasing both modulus and specific modulus. In contrast, the addition of hollow particle fillers may decrease the composite density while tuning the modulus over a wide range based on the wall thickness and the amount of microballoon added to the composite. It may be observed in FIG. 37 that the modulus of syntactic foams may be significantly higher than closed-cell foams at the same density level, and the use of syntactic foams may produce significant weight savings in structural applications. The combination of increased specific mechanical properties and decreased density may allow for a reduction of the weight of a component while retaining the desired behavior. As shown, the modulus of closed-cell foam is significantly lower than that of the matrix material, which is why their structural applications are scarce. A large number of compositions have a higher modulus than that of the matrix resin. Such compositions may be useful in load bearing structural applications.

TABLE 11

| $\Phi_{mb}$ (%) | $\eta$ | $\rho_{mb}$ (kg/m³) | $\rho_c$ (kg/m³) | $E_c$ (GPa) |
|---|---|---|---|---|
| 60 | 0.959 | 300 | 644 | 2.8 |
| 53 | 0.944 | 400 | 757 | 3.5 |
| 47 | 0.929 | 500 | 850 | 3.9 |
| 41 | 0.914 | 600 | 930 | 4.0 |
| 37 | 0.898 | 700 | 990 | 4.1 |

TABLE 12

| $\Phi_{mb}$ (%) | $\eta$ | $\rho_{mb}$ (kg/m³) | $\rho_c$ (kg/m³) | $E_c$ (GPa) |
|---|---|---|---|---|
| 57 | 0.987 | 100 | 556 | 1.2 |
| 40 | 0.973 | 200 | 776 | 2.3 |
| 30 | 0.959 | 300 | 902 | 2.8 |
| 24 | 0.944 | 400 | 978 | 3.0 |
| 20 | 0.929 | 500 | 1028 | 3.1 |
| 17 | 0.914 | 600 | 1065 | 3.2 |
| 15 | 0.898 | 700 | 1091 | 3.2 |

Syntactic Foams with SiC Particles

Hollow silicon carbide sphere (SiC$_{HS}$) reinforced vinyl ester matrix resin syntactic foams were characterized for thermal and mechanical properties. The porous nature of the walls of these hollow particles may pose a challenge in the estimation of the effective properties of the SiC$_{HS}$. Such analysis may allow the exploration of the potential for these particles for use in syntactic foam applications.

SiC$_{HS}$ may be prepared by mixing template spheres with silicon powder and heating to 1300° C. The hollow core may be formed by calcining the particles, thereby removing excess carbon. A molten salt synthesis comprising a salt bath, a carbon black template and silicon may also be utilized to obtain SiC$_{HS}$. Herein, a polyethylene core material was employed as a template, on which SiC was deposited by a chemical vapor deposition technique. SiC$_{HS}$ and a vinyl ester resin was employed to fabricate syntactic foam slabs. Methyl ethyl ketone peroxide was used as the catalyst for the resin. Syntactic foams were prepared with 60% of SiC$_{HS}$ by volume by a mechanical mixing method. The cast syntactic foam slabs were cured at room temperature for 24 hours, and then post cured at 70° C. for 3 hours in a convection oven.

Figure 38A:
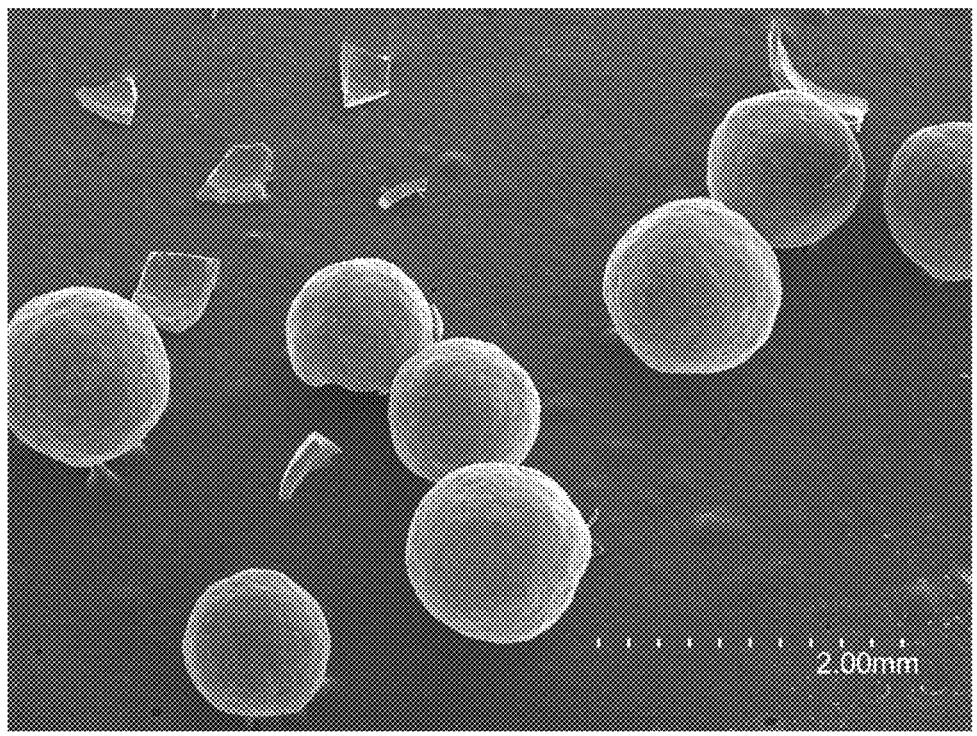
FIGS. 38A and 38B are scanning electron micrographs of SiC$_{HS}$ and the wall thickness of a broken SiC$_{HS}$, respectively.
Figure 38B:
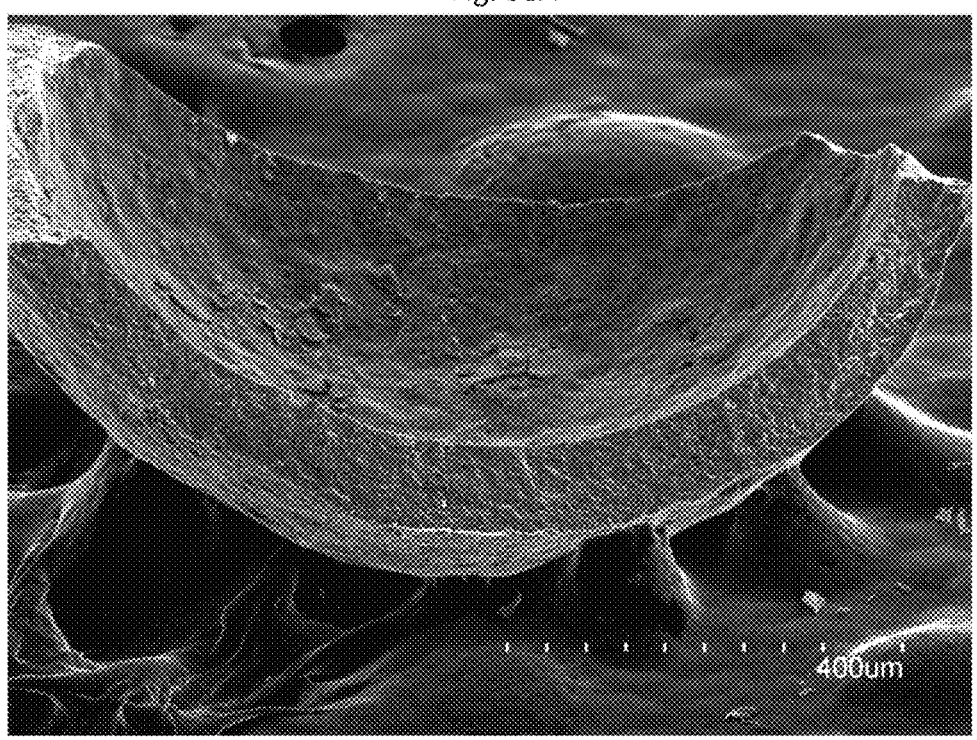

Two types of SiC$_{HS}$ were employed herein. The density of the tapped bed of these particles was measured as 440 kg/m³ and 790 kg/m³. Due to the porosity open to the surface in the walls of these particles, the direct measurement of a true particle density using equipment such as a pycnometer is not possible. FIG. 38A shows exemplary SiC$_{HS}$ employed in fabricating syntactic foams. FIG. 38B shows the wall thickness of a broken SiC$_{HS}$. The average wall thickness and the outer diameter of the SiC$_{HS}$ were evaluated as an average of 25 measurements taken on micrographs of several particles, and the results are shown in Table 13. The average radii of the two types of particles, designated as S1 and S2, were measured as 400 μm and 510 μm, respectively. The average wall thickness was measured as 36.1 μm and 81.6 μm, respectively, for these particles. The density of SiC was assumed to be 3200 kg/m³ to evaluate the ideal true particle density, which is the density of hollow particles considering these measured diameters and wall thickness and fully dense walls, using $$\rho_{HS} = \rho_{SiC}(1-\eta^3) \quad (33)$$

Figure 39:
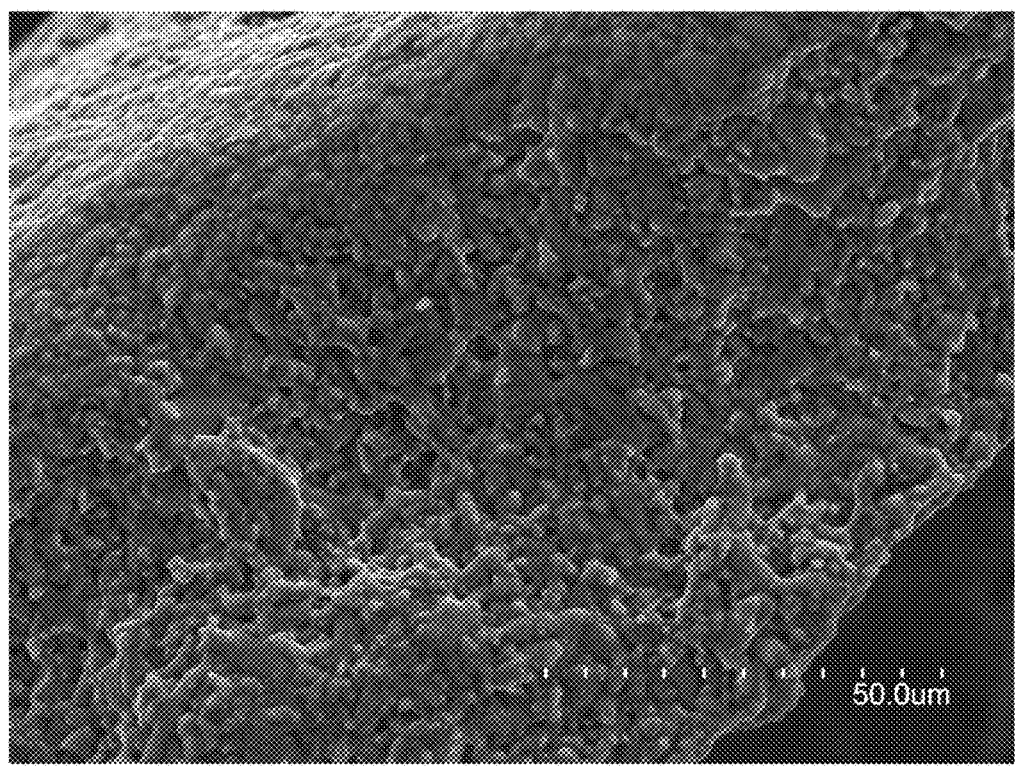
FIG. 39 is a scanning electron micrograph of SiC$_{HS}$ showing microporous voids present in the wall of the SiC$_{HS}$ sphere.

The ideal true particle density was evaluated using equation (33) and was found to be 787 kg/m³ and 1293 kg/m³ for the S1 and S2 particles, respectively, as shown in Table 13. However, the true particle density of the particles may be lower due to the porosity present in the particle walls. FIG. 39 shows the microporous voids present in the wall of the SiC$_{HS}$. The experimental density of the fabricated syntactic foams containing 60 vol. % SiC$_{HS}$ was measured to be 858±33 kg/m³ and 1048±44 kg/m³ for SF1 and SF2 type syntactic foams containing the S1 and S2 particles, respectively.

TABLE 13

| Particle type | Tap density of particle bed (kg/m³) | Average outer radius (μm) | Average wall thickness (μm) | Radius ratio $\eta$ | Ideal true particle density (kg/m³) |
|---|---|---|---|---|---|
| S1 | 440 | 400 ± 30 | 36.1 ± 4.4 | 0.91 | 787 |
| S2 | 790 | 510 ± 40 | 81.6 ± 6.8 | 0.84 | 1293 |

The quasi-static compression testing was performed on cylindrical specimens with nominal dimensions of 6.5 mm diameter and 8.5 mm thickness at a constant loading rate of 1 mm/min using an electromechanical universal test system. The CTE study was performed on a thermomechanical analyzer using cylindrical specimens with nominal dimensions of 7 mm diameter and 5 mm thickness from room temperature to 80° C. at a constant heating rate of 3° C./min.

Figure 40:
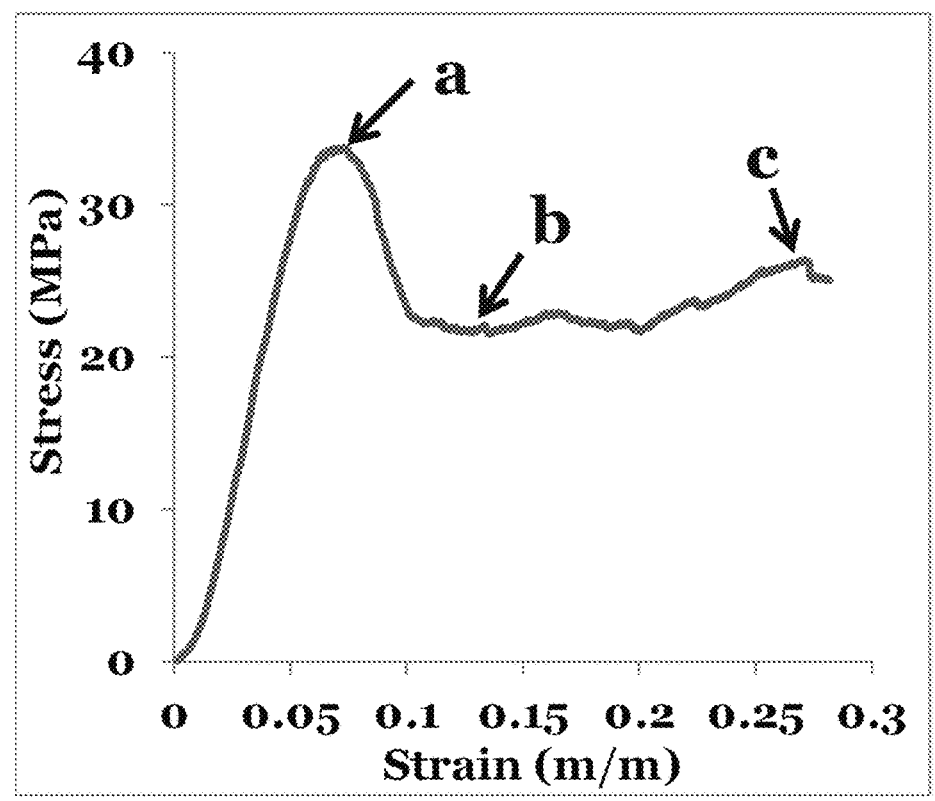
FIG. 40 depicts a quasi-static compressive stress-strain curve for the SF1 type SiC$_{HS}$/VE syntactic foam.

A representative compressive stress-strain curve of the SF1 syntactic foam is presented in FIG. 40. Similar behavior has been observed for GMB/vinyl ester and GMB/epoxy syntactic foams in previously reported experiments. The deformation features of the specimen corresponding to points a, b and c marked in FIG. 40 are shown in FIGS. 41A, 41B, and 41C, respectively. The SiC$_{HS}$ are largely intact in FIG. 41A, which corresponds to the end of the elastic deformation region. Point a in FIG. 40 indicates the onset of particle failure, where some weak particles begin to exhibit cracking. The weak particles may include thin walled or defective particles. The particle fracture corresponds to the drop in stress shown in FIG. 40. Upon further compression, crushing and compaction of the particles corresponding to the plateau region marked by point b in FIG. 40 occurs. Fracture of the particles transfers the load to the surrounding matrix material. The failure of the matrix is evidenced by the shear bands in the specimen in FIG. 41B, and crushed and compacted particles along the shear band are also observed. At specimen failure, the cracks propagate through the entire thickness of the specimen and constitute final failure, as observed in FIG. 41C. The trends of the stress-strain graph and the failure features are found to be similar for the SF1 and the SF2 syntactic foams.

The stress-strain graphs may be used to calculate the modulus, peak strength, and plateau strength of the syntactic foams, as presented in Table 14. The higher density particles provided higher peak strength but lower plateau strength and modulus. Studies on GMB filled syntactic foams have consistently shown higher strength and modulus for syntactic foams containing higher density particles. However, a similar trend is not present in this case because the particle walls are porous and some of the pores present in the walls may be larger than the critical size to initiate failure at a low stress level. The standard deviation in the plateau stress and compressive modulus is within ±11%. The specific compressive strength (normalized with respect to the corresponding syntactic foam density) of the SF1 and the SF2 syntactic foams were 33.4 kPa/kg/m³ and 38.8 kPa/kg/m³, respectively. The specific compressive modulus of the SF1 and the SF2 syntactic foams were 0.8 MPa/kg/m³ and 0.6 MPa/kg/m³, respectively. These values of the SiC$_{HS}$/VE syntactic foams are lower in comparison to previously reported GMB/VE syntactic foams. These lower compressive properties may be ascribed to the microporous voids in the walls of the particles, as shown in FIG. 39, which may produce undesirably low effective mechanical properties and early failure of some particles.

TABLE 14

| Specimen type | Peak strength (MPa) | Plateau strength (MPa) | Compressive modulus (MPa) |
|---|---|---|---|
| SF1 | 29.6 ± 4.2 | 20.8 ± 2.2 | 725.0 ± 76.0 |
| SF2 | 42.0 ± 4.7 | 18.5 ± 1.1 | 692.0 ± 47.0 |

Figure 42:
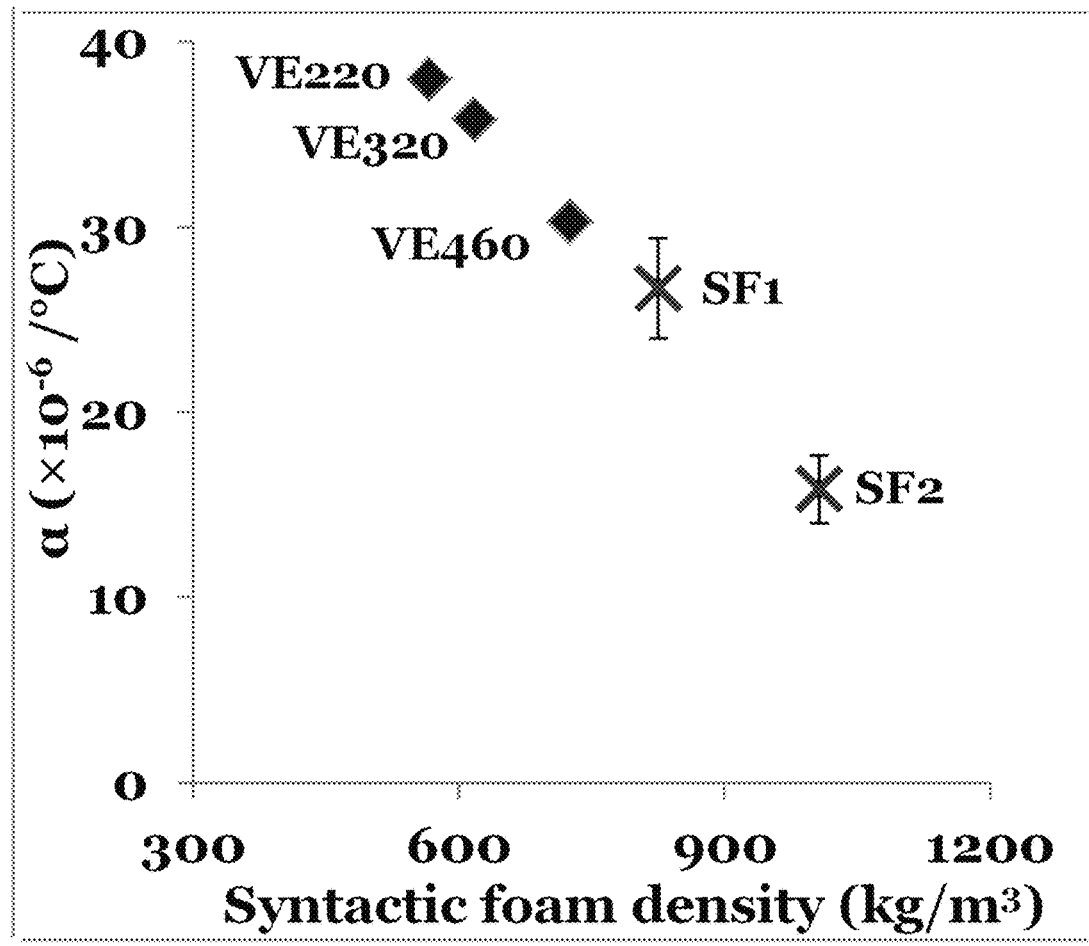
FIG. 42 depicts the variation of the CTE of syntactic foams containing 60 vol. % of various hollow spheres as a function of syntactic foam density.

Thermal strain-temperature graphs were used to calculate the CTE of the produced syntactic foams. The measured CTE of the SF1 and the SF2 syntactic foams were found to be 26.7±2.7 and 15.9±1.8×10⁻⁶/° C., respectively. The thicker walled SiC$_{HS}$ produced syntactic foams with a lower CTE than the thinner walled SiC$_{HS}$. The CTE values of SiC$_{HS}$/VE were compared with those previously reported for GMB/VE syntactic foams FIG. 42. The GMB/VE syntactic foams contain 60 vol. % of three different types of GMBs having true particle densities of 220 kg/m³, 320 kg/m³ and 460 kg/m³. The CTE values are plotted with respect to the syntactic foam density in FIG. 42. It was observed that the CTE of SiC$_{HS}$/VE is lower than the CTE values obtained for GMB/VE syntactic foams. In the case of GMB/VE syntactic foam a maximum decrease of 60.4% in CTE was observed in comparison to the CTE of the neat resin. By contrast, for the SiC$_{HS}$/VE syntactic foams a CTE decrease of 65.1% and 79.3% was observed for the SF1 and the SF2 syntactic foams in comparison to the CTE of the neat resin, respectively. It is expected that syntactic foams including SiC hollow spheres with non-porous walls will exhibit property trends based on the volume fraction and wall thickness similar to those observed for glass microballoon containing syntactic foams.

To evaluate the porosity in the wall of the S1 and the S2 SiC$_{HS}$, the density of the hollow particles was calculated from the experimentally measured density of the syntactic foams using the rule of mixture. It was assumed that there was no additional porosity present in the matrix. The true particle densities evaluated by this method are 656 kg/m³ and 973 kg/m³, for S1 and S2 SiC$_{HS}$, respectively. Using these true particle density values in Equation (33), the density of the porous SiC material was obtained as 2668 kg/m³ and 2408 kg/m³ for S1 and S2 particles, respectively, which is lower than the density of a solid SiC material (3200 kg/m³). The density difference demonstrates that the S1 and the S2 SiC$_{HS}$ contain 16.6% and 24.8% porosity, respectively.

Theoretical models have been previously reported for the purposes of estimating the CTE of syntactic foams with respect to the volume fraction (Φ) and radius ratio (η) of the hollow particles. The CTE experimentally measured herein was used in these models to estimate the properties of the porous SiC material of SiC$_{HS}$. The variation of CTE (α) of the syntactic foams based on Φ and η of the filler material is given by the Turner's model modified for application to syntactic foams $$\alpha = \frac{\alpha_m \Phi_m E_m \left[(1-2v_{SiC}) + \left(\frac{1+v_{SiC}}{2}\right)\eta^3\right] +}{\Phi_m E_m \left[(1-2v_{SiC}) + \left(\frac{1+v_{SiC}}{2}\right)\eta^3\right] +} \quad (34)$$
$$\frac{\alpha_{SiC} \Phi_b E_{SiC}(1-\eta^3)(1-2v_m)}{\Phi_b E_{SiC}(1-\eta^3)(1-2v_m)}$$

where the subscript m and b represent the matrix and the hollow filler material, respectively. The matrix modulus and Poisson ratio are assumed to be 2.82 GPa and 0.35, respectively. The Poisson ratio of SiC was assumed to be 0.14. The CTE of SiC material was assumed to be 4×10⁻⁶/° C. Using Equation (34), the modulus of the hollow sphere material (porous SiC) was estimated to be 18 GPa and 20 GPa for the S1 and the S2 particles, respectively. These values are significantly lower than the modulus of SiC, which is around 420 GPa, due to the porosity present in the walls of the hollow particles. This porosity may adversely affect the mechanical properties of the particles, but may allow the achievement of syntactic foams with a low CTE.

SiC$_{HS}$/VE syntactic foams were studied for compressive properties and coefficient of thermal expansion (CTE). Two types of SiC$_{HS}$ were used in 60 vol. % quantities to fabricate two types of syntactic foams. Direct measurement of the properties of SiC$_{HS}$ may be difficult due to their porous walls. Hence, the measured CTE and density values of syntactic foams were used to estimate the properties of SiC$_{HS}$. The ratios of the inner to the outer radius of the two types of particles, S1 and S2, were measured to be 0.91 and 0.84, respectively. The compressive modulus of the two syntactic foams, SF1 and SF2, was measured to be 725 MPa and 692 MPa, respectively. The higher density syntactic foams exhibited a lower modulus because of the porous nature of the particles. The specific compressive strength and modulus of SiC$_{HS}$/VE syntactic foams was observed to be lower in comparison to GMB/VE syntactic foams. The CTE of SiC$_{HS}$-VE was observed to be lower than compositions of GMB/VE, indicating better thermal stability for the SiC$_{HS}$ syntactic foams at high temperatures than for GMB/VE. A decrease of 65.1% and 79.3% in the CTE was observed for the two types of syntactic foams, in comparison to the CTE of the neat resin. The modulus of the hollow sphere material predicted using the modified Turner's model was observed to be significantly lower than the Young's modulus of bulk SiC, due to the presence of porosity in the particle walls. The estimated porosities in the walls of the two types of SiC$_{HS}$ were 16.6% and 24.8% for S1 and S2, respectively.

Tuning CTE and Dielectric Constant

A combination of wall thickness and volume fraction was used to simultaneously tailor the dielectric constant and CTE of a syntactic foam. The CTE may be varied between 30×10⁻⁶ ° C. and 70×10⁻⁶ ° C. for syntactic foams having a dielectric constant of 3 in vinyl ester matrix glass microballoon filled syntactic foams. To obtain these CTE values, the hollow particle volume fraction and density may be varied. Similar calculations may be conducted for other desired values of dielectric constant and CTE.

Glass hollow particles were employed in a vinyl ester matrix to fabricate syntactic foams. However, the method is generic and may be applied to any combination of hollow particles and matrix material. The produced syntactic foams may be suitable for electronic packaging applications.

A syntactic foam composite material was developed that may be simultaneously tailored for a desired dielectric constant and coefficient of thermal expansion (CTE). A range of compositions may be developed for syntactic foams that have the same dielectric constant but have different CTE values and vice versa. The selection of an appropriate material composition based on the proposed approach may provide syntactic foams with both the desired dielectric constant and the desired CTE.

Figure 43A:
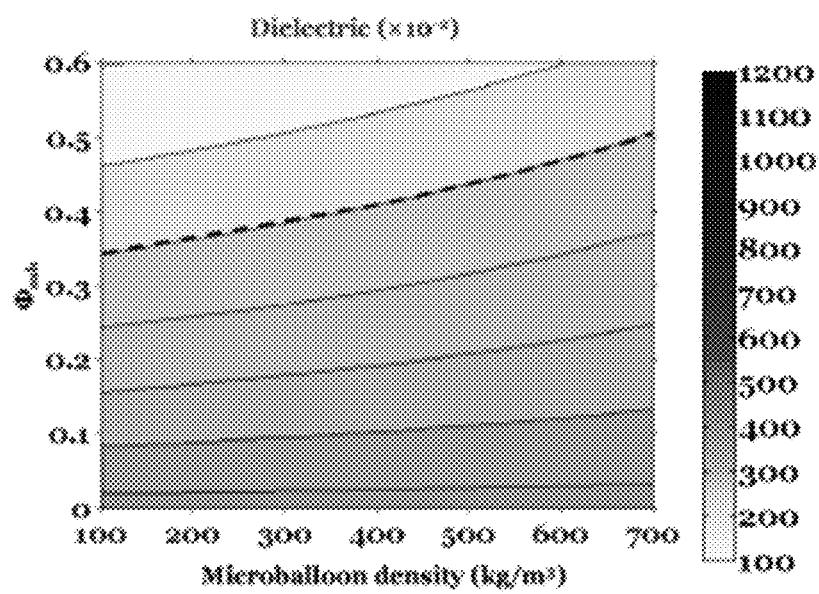
FIGS. 43A and 43B depict the dielectric constant and CTE, respectively, of a syntactic foam as a function of microballoon density and volume fraction.
Figure 43B:
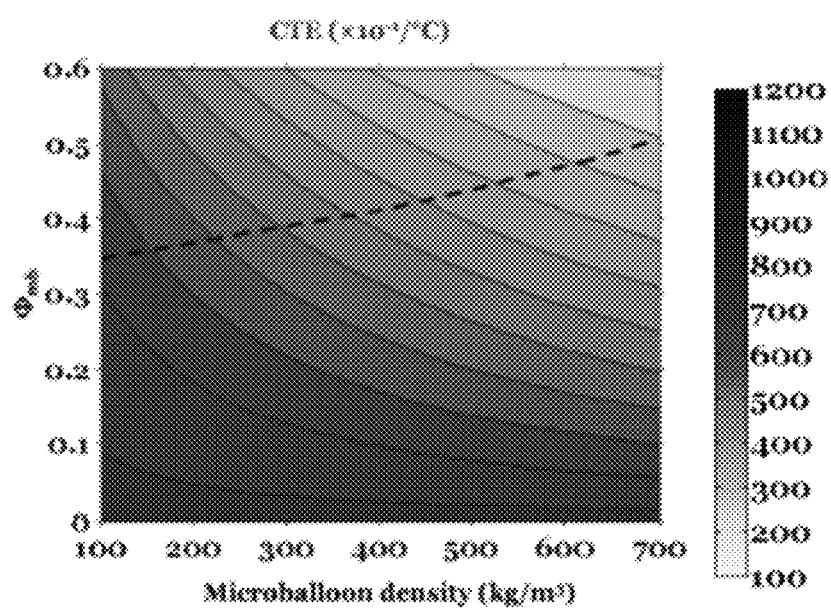
Figure 44:
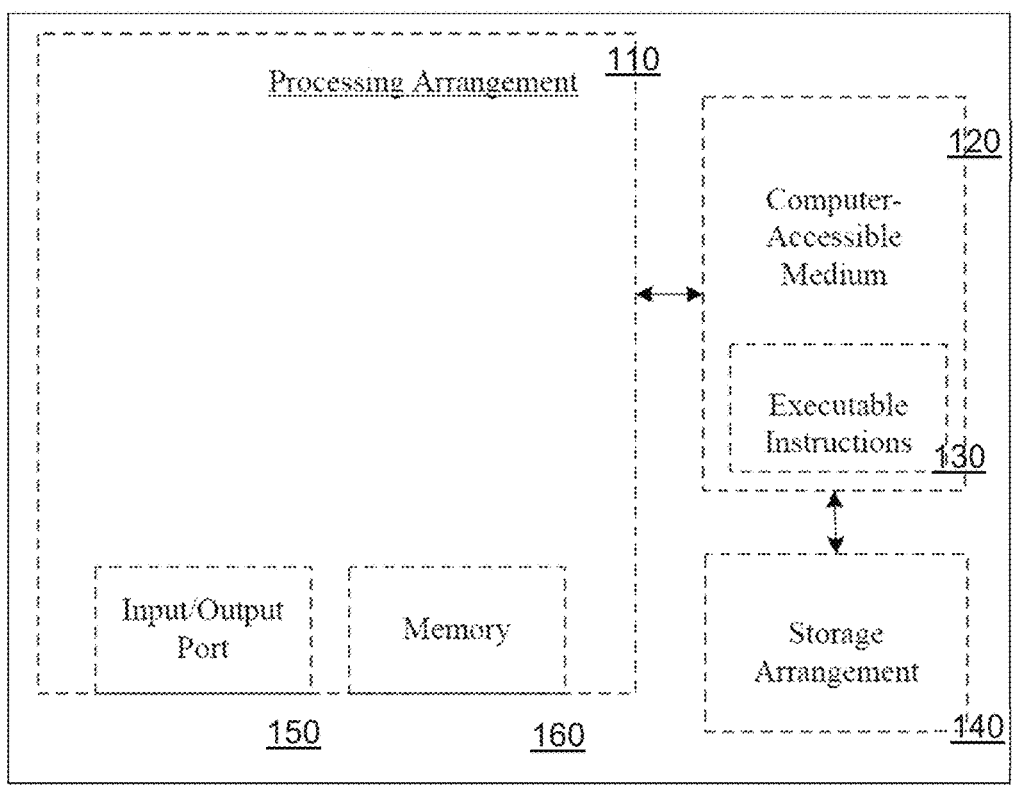
FIG. 44 illustrates a computer system for use with certain implementations.

A combination of wall thickness and volume fraction may be employed to simultaneously tailor the dielectric constant and the CTE. FIGS. 43A and 43B depict a scheme for the selection of an appropriate hollow particle volume fraction and wall thickness for obtaining the desired properties in a syntactic foam. A line is marked in FIG. 43A representing the syntactic foam compositions that have a dielectric constant of 3. The same line indicating a dielectric constant of 3 is projected on FIG. 43B, to indicate the CTE values of the syntactic foam compositions. It was found that the CTE may be varied between $30 \times 10^{-6}$° C. and $7010$° C. for syntactic foams having a dielectric constant of 3. To obtain these CTE values, the hollow particle volume fraction and density may be varied, as provided in Table 15 for compositions with a dielectric constant of 3. Similar calculations may be conducted for other desired values of dielectric constant and CTE.

TABLE 15

| Composition # | $\rho_{mb}$ (kg/m³) | $\Phi_{mb}$ (%) | η | $\rho_c$ (kg/m³) | α ($10^{-6}$/° C.) |
|---|---|---|---|---|---|
| 1 | 100 | 34 | 0.987 | 800 | 69.2 |
| 2 | 200 | 36 | 0.973 | 914 | 62.1 |
| 3 | 300 | 38 | 0.959 | 833 | 55.2 |
| 4 | 400 | 41 | 0.944 | 848 | 48.2 |
| 5 | 500 | 44 | 0.929 | 870 | 41.6 |
| 6 | 600 | 47 | 0.914 | 897 | 35.8 |
| 7 | 700 | 51 | 0.898 | 925 | 29.9 |

As used herein, $\rho_{mb}$ is the density of hollow particle, $\Phi_{mb}$ is the hollow particle volume fraction, η is the radius of internal to outer radius of hollow particle, $\rho_c$ is the syntactic foam density, and α is the CTE of syntactic foam.

The dielectric constant of syntactic foams (a) decreases with increasing $\Phi_{mb}$ of GMBs, (b) decreases with increasing test frequency, and (c) increases with increasing temperature. Impedance exhibits behavior similar to that of the dielectric constant with respect to $\Phi_{mb}$ and frequency.

Additional Notes

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." Any ranges cited herein are inclusive.

The terms "substantially" and "about" used throughout this Specification are used to describe and account for small fluctuations. For example, they may refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As shown in FIG. 4, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:
1. A method comprising:
calculating, utilizing at least one computer, a range of potential values for a first material property of a syntactic foam, the syntactic foam including a matrix material and hollow particles, on the basis of a wall thickness and a volume fraction of the hollow particles;
selecting a first material property value from the range of potential values for the first material property;
calculating, utilizing at least one computer, a range of potential values for a second material property of the syntactic foam on the basis of the wall thickness and the volume fraction of the hollow particles while maintaining the selected first material property value;
selecting a second material property value from the range of potential values for the second material property;
calculating, utilizing at least one computer, the wall thickness and the volume fraction of the hollow particles that will produce a syntactic foam with the selected first material property value and the selected second material property value; and
producing a syntactic foam with the wall thickness and the volume fraction of the hollow particles that will produce a syntactic foam with the selected first material property value and the selected second material property value;
wherein the first material property and the second material property are selected from the dielectric constant, coefficient of thermal expansion (CTE), damping capacity, elastic modulus, storage modulus, loss modulus, and density; and the first material property is different than the second material property.

2. The method of claim 1, wherein the first material property is the dielectric constant and the second material property is the CTE.

3. The method of claim 1, wherein the matrix material comprises a vinyl ester resin.

4. The method of claim 1, wherein the matrix material comprises aluminum.

5. The method of claim 1, wherein the hollow particles comprise glass microballoons.

6. The method of claim 1, wherein the hollow particles comprise hollow silicon carbide spheres.

7. The method of claim 1, further comprising limiting the calculated range of potential values for the first material property and the calculated range of potential values for the second material property are further limited on the basis of the available raw materials.

8. A method comprising:
calculating, utilizing at least one computer, a range of potential values for a first material property of a syntactic foam, the syntactic foam including a polymer matrix material and hollow glass particles, on the basis of a wall thickness and a volume fraction of the hollow glass particles;
selecting a first material property value from the range of potential values for the first material property;
calculating, utilizing at least one computer, a range of potential values for a second material property of the syntactic foam on the basis of the wall thickness and the volume fraction of the hollow glass particles while maintaining the selected first material property value;
selecting a second material property value from the range of potential values for the second material property;
calculating, utilizing at least one computer, the wall thickness and the volume fraction of the hollow glass particles that will produce a syntactic foam with the selected first material property value and the selected second material property value; and
further comprising producing a syntactic foam with the wall thickness and the volume fraction of the hollow particles that will produce a syntactic foam with the selected first material property value and the selected second material property value;
wherein the first material property and the second material property are selected from the dielectric constant and the coefficient of thermal expansion (CTE); and the first material property is different than the second material property.

9. The method of claim 8, wherein the matrix material is a vinyl ester resin.

10. The method of claim 8, wherein the hollow glass particles are hollow glass spheres.

11. The method of claim 8, wherein the volume fraction of the hollow glass particles that will produce a syntactic foam with the selected first material property value and the selected second material property value is of about 0.35 to about 0.5.

12. A syntactic foam with a coefficient of thermal expansion of about $30\times10^{-6}/°$ C. to about $70\times10^{-6}/°$ C. and a dielectric constant of about 2.6 to about 4.9, wherein the syntactic foam comprises a matrix material and hollow particles.

13. The syntactic foam of claim 12, wherein the dielectric constant is about 3.

14. The syntactic foam of claim 12, wherein the syntactic foam has a density of about 570 kg/m$^3$ to about 937 kg/m$^3$.

15. The syntactic foam of claim 12, wherein the volume fraction of the hollow particles in the syntactic foam is about 0.35 to about 0.5.

16. The syntactic foam of claim 12, wherein the hollow particles have a radius ratio of about 0.898 to about 0.987.

17. The syntactic foam of claim 12, further comprising a matrix porosity of about 1.2 vol. % to about 4.5 vol. %.

18. The syntactic foam of claim 12, wherein the syntactic foam is an electrical device component.

* * * * *